US009567370B2

(12) United States Patent
Karim et al.

(10) Patent No.: US 9,567,370 B2
(45) Date of Patent: *Feb. 14, 2017

(54) THERAPEUTIC AGENTS FOR REDUCING PARATHYROID HORMONE LEVELS

(71) Applicant: KAI Pharmaceuticals, Inc., South San Francisco, CA (US)

(72) Inventors: Felix Karim, Walnut Creek, CA (US); Amos Baruch, San Francisco, CA (US); Derek Maclean, Los Altos, CA (US); Kanad Das, San Francisco, CA (US); Qun Yin, Palo Alto, CA (US)

(73) Assignee: KAI PHARMACEUTICALS, INC., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/639,020

(22) Filed: Mar. 4, 2015

(65) Prior Publication Data
US 2015/0175664 A1 Jun. 25, 2015

Related U.S. Application Data

(63) Continuation of application No. 12/846,724, filed on Jul. 29, 2010, now Pat. No. 8,999,932.

(60) Provisional application No. 61/313,635, filed on Mar. 12, 2010, provisional application No. 61/255,816, filed on Oct. 28, 2009, provisional application No. 61/229,695, filed on Jul. 29, 2009.

(51) Int. Cl.
C07K 7/08 (2006.01)
C07K 7/06 (2006.01)
A61K 47/48 (2006.01)
C07K 5/103 (2006.01)
A61K 38/00 (2006.01)

(52) U.S. Cl.
CPC ............ C07K 7/08 (2013.01); A61K 47/48215 (2013.01); C07K 5/1013 (2013.01); C07K 7/06 (2013.01); A61K 38/00 (2013.01)

(58) Field of Classification Search
None
See application file for complete search history.

(56) References Cited

U.S. PATENT DOCUMENTS

| 5,246,925 A | 9/1993 | DeLuca et al. |
| 5,587,497 A | 12/1996 | DeLuca et al. |
| 5,602,116 A | 2/1997 | Knutson et al. |
| 5,688,489 A | 11/1997 | Peers et al. |
| 5,837,218 A | 11/1998 | Peers et al. |
| 5,861,386 A | 1/1999 | Knutson et al. |
| 5,869,473 A | 2/1999 | Knutson et al. |
| 6,031,003 A | 2/2000 | Nemeth et al. |
| 6,051,567 A | 4/2000 | Abrahamson et al. |
| 6,165,977 A | 12/2000 | Mochly-Rosen |
| 6,265,392 B1 | 7/2001 | Abrahamson et al. |
| 6,274,169 B1 | 8/2001 | Abrahamson et al. |
| 6,290,665 B1 | 9/2001 | Utterberg |
| 6,855,693 B2 | 2/2005 | Mochly-Rosen et al. |
| 6,903,083 B2 | 6/2005 | Knutson et al. |
| 7,081,444 B2 | 7/2006 | Mochly-Rosen |
| 7,265,092 B2 | 9/2007 | Li |
| 8,377,880 B2 | 2/2013 | Karim et al. |
| 8,969,299 B2 | 3/2015 | Karim et al. |
| 8,987,200 B2 | 3/2015 | Bell et al. |
| 8,999,932 B2 | 4/2015 | Karim et al. |
| 2002/0068342 A1 | 6/2002 | Khosravi et al. |
| 2003/0036627 A1 | 2/2003 | Montalero et al. |
| 2004/0018976 A1 | 1/2004 | Feder et al. |
| 2005/0187156 A1 | 8/2005 | Mochly-Rosen |
| 2006/0111274 A1 | 5/2006 | Rothbard et al. |
| 2006/0153867 A1 | 7/2006 | Li |
| 2007/0066514 A1 | 3/2007 | Haberberger et al. |
| 2008/0249016 A1 | 10/2008 | Henriksen et al. |
| 2009/0023652 A1 | 1/2009 | Bell et al. |
| 2009/0214550 A1 | 8/2009 | Sahin et al. |
| 2011/0028394 A1 | 2/2011 | Karim et al. |
| 2012/0178988 A1 | 7/2012 | Karim et al. |
| 2013/0150297 A1 | 6/2013 | Karim et al. |
| 2013/0150301 A1 | 6/2013 | Karim et al. |
| 2014/0315809 A1 | 10/2014 | Walter et al. |
| 2015/0175664 A1 | 6/2015 | Karim et al. |

FOREIGN PATENT DOCUMENTS

| CA | 2145214 A1 | 8/1996 |
| JP | 2000-336099 A | 12/2000 |

(Continued)

OTHER PUBLICATIONS

Arenas et al., "Implementation of K/DOQI clinical practice guideline for bone metabolism and disease in chronic kidney disease after the introduction cinacalcet in a population of patients on chronic haemodialysis", Nephrology Dialysis Transplantation, vol. 22, No. 6, pp. 1639-1644 (2007).

(Continued)

Primary Examiner — Robert A Wax
Assistant Examiner — William Craigo
(74) Attorney, Agent, or Firm — McDermott Will & Emery LLP

(57) ABSTRACT

Compounds having activity for lowering parathyroid hormone levels are described. In one embodiment, the compounds are comprised of a contiguous sequence of subunits, $X_1$-$X_2$-$X_3$-$X_4$-$X_5$-$X_6$-$X_7$, wherein the $X_1$ subunit comprises a thiol-containing moiety and the distribution of charge on the $X_2$-$X_7$ subunits provides the desired activity. Methods of using the compounds for treating hyperparathyroidism, bone disease and/or hypercalcemic disorders are also described, and in particular, methods for lowering plasma PTH and serum calcium are provided. The compounds can be used to treat subjects having, for example: primary, secondary or tertiary hyperparathyroidism; hypercalcemia of malignancy; metastatic bone disease; or osteoporosis.

28 Claims, 9 Drawing Sheets

(56) References Cited

FOREIGN PATENT DOCUMENTS

| | | |
|---|---|---|
| JP | 2013-099331 A2 | 5/2013 |
| WO | WO 92/08476 A1 | 5/1992 |
| WO | WO 95/11988 A1 | 5/1995 |
| WO | WO 98/33812 A1 | 8/1998 |
| WO | WO 98/51324 | 11/1998 |
| WO | WO 99/47173 A2 | 9/1999 |
| WO | WO 02/16424 A2 | 2/2002 |
| WO | WO 02/062396 A2 | 8/2002 |
| WO | WO 02/070547 A1 | 9/2002 |
| WO | WO 03/014078 A2 | 2/2003 |
| WO | WO 03/082923 A1 | 10/2003 |
| WO | WO 2005/049647 A2 | 6/2005 |
| WO | WO 2005/059124 A2 | 6/2005 |
| WO | WO 2005/072340 A2 | 8/2005 |
| WO | WO 2008/067199 A2 | 6/2008 |
| WO | WO 2008/089491 A2 | 7/2008 |
| WO | WO 2009/046220 A2 | 4/2009 |
| WO | WO 2009/075773 A2 | 6/2009 |
| WO | WO 2011/014707 A2 | 3/2011 |
| WO | WO 2013/071262 A1 | 5/2013 |

OTHER PUBLICATIONS

Goodman "Calcimimetic agents for the treatment of secondary hyperparathyroidism", Semin Nephrol., vol. 24, No. 5, pp. 460-463 (2004).
Harris et al., "Pharmacokinetics, pharmacodynamics, and safety of cinacalcet hydrochloride in hemodialysis patients at doses up to 200 mg once daily", Am. J. Kidney Dis., vol. 44, No. 6, pp. 1070-1076 (2004).
Padhi and Harris, "Clinical pharmacokinetic and pharmacodynamic profile of cinacalcet hydrochloride", Clin. Pharmacokinetics, vol. 48, No. 5, pp. 303-311 (2009).
Platt et al., "Middle-term use of cinacalcet in paediatric dialysis patients", Pediatr. Nephrol., vol. 25, No. 1, pp. 143-148 (2009).
Schaefer et al., "Efficacy of cinacalcet administered with the first meal after dialysis: the SENSOR study", Clinical Nephrology, vol. 70, No. 2, 126-143 (2008).
Stoelting et al., "Haemodynamic changes and circulating histamine concentrations following protamine administration to patients and dogs", Can. Anaesth. Soc. J., vol. 31, No. 5, pp. 534-540 (1984).
Aizawa et al., "Protein kinase C-epsilon primes the cardiac sarcolemmal adenosine triphosphate-sensitive potassium channel to modulation by isoflurane", Anesthesiology, vol. 101, No. 2, pp. 381-389 (2004).
Aladren, "Cinacalcet reduces vascular and soft tissue calcification in secondary hyperparathyroidism (SHPT) in hemodialysis patients", Clin. Nephrol., vol. 71, No. 2, pp. 207-213. (2009).
Alessandri-Haber et al., "A transient receptor potential vanilloid 4-dependent mechanism of hyperalgesia is engaged by concerted action of inflammatory mediators", J. Neurosci., vol. 26, No. 14, pp. 3864-3874 (2006).
Aley et al., "Chronic hypersensitivity for inflammatory nociceptor sensitization mediated by the epsilon isozyme of protein kinase C", J. Neurosci., vol. 20, No. 12, p. 4680-4685 (2000).
Aley and Levine, "Contribution of 5- and 12-lipoxygenase products to mechanical hyperalgesia induced by prostaglandin E(2) and epinephrine in the rat", Exp. Brain Res., vol. 148, No. 4, pp. 482-487 (2003).
Almirall et al., "Effects of cinacalcet on vascular calcification in haemodialysis patients", Nephrol. Dial. Transplant, vol. 25 No. 8, pp. 2800 (2010).
Anderson et al., "The effect of protamine derivatives on calcium metabolism in patients with malignancy", Br. J. Cancer, vol. 21, No. 1, pp. 48-55 (1967).
Antonsen et al., "A calcimimetic agent acutely suppresses parathyroid hormone levels in patients with chronic renal failure", Rapid communication, Kidney Int., vol. 53, No. 1, pp. 223-227 (1998).

Apple et al., "Differential effects of protein kinase C isoform activation in endothelin-mediated myocyte contractile dysfunction with cardioplegic arrest and reperfusion", Ann. Thorac. Surg., vol. 82, No. 2, pp. 664-671 (2006).
Arey et al., "A novel calcium-sensing receptor antagonist transiently stimulates parathyroid hormone secretion in vivo", Endocrinology, vol. 146, No. 4, pp. 2015-2022 (2005).
Aridor et al., "Exocytosis in mast cells by basic secretagogues: evidence for direct activation of GTP-binding proteins", J. Cell Biol., vol. 111, pp. 909-917 (1990).
Bakker et al., "8R-lisuride is a potent stereospecific histamine H1-receptor partial agonist", Mol. Pharmacol., vol. 65, No. 3, pp. 538-549 (2004).
Banci et al., "Molecular dynamics of characterization of the C2 domain of protein kinase Cbeta", J. Biol. Chem., vol. 277, No. 15, p. 12988-12997 (2002).
Baruch et al., "KAI-4169, a novel Peptide Agonist of the Calcium Sensing Receptor for the Treatment of Secondary Hyperparathyroidism" Endocrine Society 93rd Annual Meeting (ENDO 2011), Boston Jun. 4-8, 2011 (Endocr Rev 32: P2-98) (2011).
Begley et al., "Biodistribution of intracellularly acting peptides conjugated reversibly to tat", Biochem. Biophys. Res. Commun., vol. 318, No. 4, p. 949-954 (2004).
Bell et al., "Calcimimetic KAI-4169 Reduces Parathyroid Hormone (PTH) Dose-dependently", (Posters#:SA23) ISN World Congress of Nephrology. Vancouver, Apr. 8-12, 2011.
Besena et al., "Activation of protein kinase C epsilon inhibits the two-pore domain K+ channel, TASK-1, inducing repolarization abnormalities in cardiac ventricular myocytes", J. Biol. Chem., vol. 279, No. 32, pp. 33154-33160 (2004).
Block et al., "The impact of calcimimetics on mineral metabolism and secondary hyperparathyroidism in end-stage renal disease", Kidney Int. Suppl., vol. 87, pp. S131-S136 (2003).
Block et al., "Results of a Phase 2 study evaluating the safety and efficacy of KAI-4169, a novel peptide for the treatment of chronic kidney disease-mineral and bone disorder in hemodialysis subjects", (Poster: LBCT-P03147) American Society of Nephrology, Philadelphia, Nov. 2011.
Block et al., "Cinacalcet for secondary hyperparathyroidism in patients receiving hemodialysis", N. Engl. J. Med., vol. 350, No. 15, pp. 1516-1525 (2004).
Braun and Mochly-Rosen, "Opposing effects of delta- and zeta-protein kinase C isozymes on cardiac fibroblast proliferation: Use of isozyme-selective inhibitors", J. Mol. Cell Cardiol., vol. 35, No. 8, p. 895-903 (2003).
Breitwieser, "Calcium sensing receptors and calcium oscillations: calcium as a first messenger", Curr. Top. Dev. Biol., vol. 73, pp. 85-114 (2006).
Brennan and Conigrave, "Regulation of cellular signal transduction pathways by the extracellular calcium-sensing receptor", Curr. Pharm. Biotechnol., vol. 10, No. 3, pp. 270-281 (2009).
Bright et al., "Protein kinase C delta mediates cerebral reperfusion injury in vivo", J. Neuroscience, vol. 24, No. 31, p. 6880-6888 (2004).
Bright and Mochly-Rosen, "The role of protein kinase C in cerebral ischemic snd reperfusion in injury", Stroke, vol. 36, No. 12, p. 2781-2790 (2005).
Brown et al., "Decreased calcium-sensing receptor expression in hyperplastic parathyroid glands of uremic rats: role of dietary phosphate", Kidney Int., vol. 55, 4pp. 1284-1292 (1999).
Brown, "Clinical utility of calcimimetics targeting the extacellular calcium-sensing receptor (CaSR)", Biochem. Pharmacol., vol. 80, No. 3, pp. 297-307 (2010).
Brown et al., "Cloning and characterization of an extracellular Ca(2+)-sensing receptor from bovine parathyroid", Nature, vol. 366 No. 6455, pp. 575-580 (1993).
Brown et al., "Ouabain and low extracellular potassium inhibit PTH secretion from bovine parathyroid cells by a mechanism that does not involve increases in the cytosolic calcium concentration", Metabolism, vol. 36, No. 1, pp. 36-42 (1987).

(56) References Cited

OTHER PUBLICATIONS

Brown et al., "Neomycin mimics the effects of high extracellular calcium concentrations on parathyroid function in dispersed bovine parathyroid cells", Endocrinology, vol. 128, No. 6, pp. 3047-3054 (1991).
Brown and MacLeod, "Extracellular calcium sensing and extracellular calcium signaling", Physiol. Rev., vol. 81, No. 1, pp. 239-297 (2001).
Brown et al., "Polyarginine, polylysine, and protamine mimic the effects of high extracellular calcium concentrations on dispersed bovine parathyroid cells", J. Bone Miner. Res., vol. 6, pp. 1217-1225 (1991).
Brzoska et al., "The product of the ataxia-telangiectasia group D complementing gene, ATDC, interacts with a protein kinase C substrate and inhibitor", PNAS, vol. 92, No. 17, p. 7824-7828 (1995).
Buhagiar et al., "Protein kinase C epsilon contributes to regulation of the sarcolemmal Na(+)-K(+) pump", Am. J. Physiol. Cell Physiol., vol. 281, No. 3, pp. c1059-c1063 (2001).
Busque et al., "L-type amino acids stimulate gastric acid secretion by activation of the calcium-sensing receptor in parietal cells", Am. J. Physiol. Gastrointest. Liver Physiol., vol. 289 No. 4, pp. G664-G669. (2005).
Cardone et al., "Phorbol myristate acetate-mediated stimulation of trancytosis and apical recycling in MDCK cells", J. Cell. Biol., vol. 124, No. 5, p. 717-727 (1994).
Cardone et al., "Signal transduction by the polymeric immunoglobulin receptor suggests a role in regulation of receptor transcytosis", J. Cell. Biol., vol. 133, No. 5, p. 997-1005 (1996).
Caudrillier et al., "Calcium-sensing receptor as a potential modulator of vascular calcification in chronic kidney disease", J. Nephrol., vol. 23, No. 1, pp. 17-22 (2010).
Chang and Tepperman, "Effects of selective PKC isoform activation and inhibition on TNF-α-induced injury and apoptosis in human intestinal epithelial cells", British Journal of Pharmacology, vol. 140, p. 41-52 (2003).
Chattopadhyay et al., "Regulation of secretion of PTHrP by Ca(2+)-sensing receptor in human astrocytes, astrocytomas, and meningiomas", Am. J. Physiol. Cell Physiol., vol. 279(3): C691-C699 (2000).
Chaudary et al., "The adenosine transporter, mENT1, is a target for adenosine receptor signaling and protein kinase C epsilon in hypoxic and pharmacological preconditioning in the mouse cardiomyocyte cell line, HL-1", J. Pharmacol. Exp. Ther., vol. 310, No. 3, pp. 1190-1198 (2004).
Chen and Goodman, "Role of the calcium-sensing receptor in parathyroid gland physiology", Am. J. Physiol. Renal Physiol., vol 286, No. pp. F1005-F1011 (2004).
Chen et al., "Cardioprotection from ischemia by a brief exposure to physiological levels of ethanol: Role of epsilon protein kinase C", PNAS, vol. 96, No. 22, p. 12784-12789 (1999).
Chen et al., "Molecular transporters for peptides: delivery of a cardioprotective εPKC agonist peptide into cells and intact ischemic heart using a transport system, R", Chem. Biol., vol. 8, pp. 1123-1129 (2001).
Chen et al., "Opposing cardioprotective actions and parallel hypertrophic effects of delta PKC and epsilon PKC", PNAS, vol. 98, No. 20, p. 11114-11119 (2001).
Cho et al., "Covalent attachment of TAT peptides and thiolated alkyl molecules on GaAs surfaces", J. Phys. Chem. B, vol. 109, No. 26, pp. 12731-12737 (2005).
Church et al., "Characterization of histamine secretion from mechanically dispersed human lung mast cells; effects of anti-IgE, calcium ionophore A23187, compound 48/80, and basic polypeptides", J. Immunol., vol. 129, No. 5, pp. 2116-2121 (1982).
Churchill et al., "Reperfusion-induced translocation of deltaPKC to cardiac mitochondria prevents pyruvate dehydrogenase reactivation", Circ. Res., vol. 97, No. 1, pp. 79-85 (2005).
Colloton et al., "Cinacalcet HCl attenuates parathyroid hyperplasia in a rat model of secondary hyperparathyroidism", Kidney Int., vol. 67, No. 2, pp. 467-476 (2005).
Conigrave and Brown, "Taste receptors in the gastrointestinal tract II. L-amino acid sensing by calcium-sensing receptors: implications for GI physiology", Am. J. Physiol. Gastrointest Liver Physiol., vol. 291, No. 5, pp. G753-G761 (2006).
Conigrave et al., "Dietary protein and bone health: roles of amino acid-sensing receptors in the control of calcium metabolism and bone homeostasis", Annu. Rev. Nutr., vol. 28, pp. 131-155 (2008).
Conigrave et al., "L-amino acid sensing by the calcium-sensing receptor: a general mechanism for coupling protein and calcium metabolism?", Eur. J. Clin. Nutr., vol. 56, No. 11, pp. 1072-1080 (2002).
Conigrave et al., "Physiological significance of L-amino acid sensing by extracellular Ca(2+)-sensing receptors", Biochem. Soc. Trans., vol. 35, Pt. 5, pp. 1195-1198 (2007).
Conigrave et al., "L-amino acids regulate parathyroid hormone secretion", J. Biol. Chem., vol. 279, No. 37, pp. 38151-38159 (2004).
Conigrave et al., "Aromatic L-amino acids activate the calcium-sensing receptor", J. Nutr., vol. 137, No. 6 Suppl. 1, pp. 1524S-1527S, discussion 1548S (2007).
Conigrave et al. "L-amino acid sensing by the extracellular Ca2+-sensing receptor", Proc. Natl. Acad. Sci. USA, vol. 97, No. 9, pp. 4814-4819 (2000).
Conigrave et al., "Cooperative multi-modal sensing and therapeutic implications of the extracellular Ca(2+) sensing receptor", Trends Pharmacol. Sci., vol. 10, pp. 401-407 (2000).
Csukai et al., "The coatomer protein beta-COP, a selective binding protein (RACK) for protein kinase C epsilon", J. Biol. Chem., vol. 272, No. 46, p. 29200-29206 (1997) Csukai, et al., "The coatomer protein beta-COP, a selective binding protein (RACK) for protein kinase C epsilon", J. Biol. Chem., vol. 272, No. 46, p. 29200-29206 (1997).
Csukai and Mochly-Rosen, "Molecular genetic approaches. II. Expression-interaction cloning," Methods Mol. Biol., vol. 88, p. 133-139 (1998).
Csukai and Mochly-Rosen, "Pharmacologic modulation of protein kinase C isozymes: The role of RACKs and subcellular localization", Pharmacological Research, vol. 39, No. 4, p. 253-259 (1999).
Dehgani et al., "Subcellular localization of protein kinase C delta and epsilon affects transcriptional and post-transcriptional processes in four-cell mouse embryos", Reproduction, vol. 130, No. 4, pp. 453-465 (2005).
Delaney, "Managing bone mineral disorders in CKD: an overview of current therapies", J. Ren. Care, vol. 35, Suppl 1, pp. 107-110 (2009).
Dell et al., "The betagamma subunit of heterotrimeric G proteins interacts with RACK 1 and two other WD repeat proteins", J. Biol. Chem., vol. 277, No. 51, p. 49888-49895 (2002).
Dempsey et al., "Protein kinase C isozymes and the regulation of divers cell responses", Am. J. Physiol. Lung Cell Mol. Physiol., vol. 279, No. 3, p. L429-L438 (2000).
Diamond et al., "The role of adenosine and adenosine transport in ethanol-induced cellular tolerance and dependence. possible biologic and genetic markers of alcholism", Ann. N.Y. Acad. Sci., vol. 625, p. 473-487 (1991).
Dina et al., "Primary afferent second messenger cascades interact with specific integrin subunits in producing inflammatory hyperalgesia", Pain, vol. 115, No. 1-2, pp. 191-203 (2005).
Disatnik et al., "Distinct responses of protein kinase C Isozymes to c-erbB-2 activation in SKBR-3 human breast carcinoma cells", Cell Growth Differ., vol. 5, No. 8, p. 873-880 (1994).
Disatnik et al., "Localization of protein kinase C isozymes in cardiac myocytes", Exp. Cell. Res., vol. 210, No. 2, p. 287-297 (1994).
Disatnik et al., "Phospholipase C-gamma 1 binding to intracellular receptors for activated protein kinase C", PNAS, vol. 91, No. 2, p. 559-563 (1994).
Disatnik et al., "Stimulus-dependent subcellular localizaton of activated protein kinase C, a study with acidic fibroblast growth factor

(56) References Cited

OTHER PUBLICATIONS and transforming growth factor-beta 1 in cardiac myocytes", J. Mol. Cell. Cardiol., vol. 27, No. 11, p. 2473-2481 (1995).
Disatnik et al., "Sequential activation of individual PKC isozymes in integrin-mediated muscle cell spreading: A role of MARCKS in an integrin signaling pathway", J. Cell Science, vol. 115, p. 2151-2163 (2002).
Dorn et al., "Sustained in vivo cardiac protection by a rationally designed peptide that causes epsilon protein kinase C translocation", PNAS, vol. 96, No. 22, p. 12798-12803 (1999).
Dorn and Mochly-Rosen, "Intracellular transport mechanisms of signal transducers", Annu. Rev. Physiol., vol. 64, p. 407-429 (2002).
Endemann et al., "Cytotoxicity of pEGFP vector is due to residues encoded by multiple cloning site", Anal. Biochem., vol. 313, No. 2, p. 345-347 (2003).
Endemann and Mochly-Rosen, "Methods for detecting binding proteins: An introduction", Methods Mol. Biol., vol. 233, p. 307-325 (2003).
Fan et al., "Mutational analysis of the cysteines in the extracellular domain of the human Ca2+ receptor: effects on cell surface expression, dimerization and signal transduction", FEBS Lett., vol. 436, No. 3, pp. 353-356 (1998).
Fasciotto et al., "Pancreastatin, a presumed product of chromogranin-A (secretory protein-I) processing. inhibits secretion from porcine parathyroid cells in culture", Endocrinology, vol. 125, No. 3, pp. 1617-1622 (1989).
Final Office Action Mailed Nov. 18, 2011 with respect to U.S. Appl. No. 11/941,857.
Fiorino et al., "A new cell-permeable calpain inhibitor", J. Peptide Sci., vol. 13, No. 1, pp. 70-73 (2007).
Foreman and Lichtenstein, "Induction of histamine secretion by polycations", Biochim. Biophys. Acta, vol. 629, No. 3, pp. 587-603 (1980).
Garcia-Navarro et al., "Developmental expression of protein kinase C subspecies in rat brain-pituitary axis", Mol. Cell Endochrinol., vol. 103, No. 1, p. 133-138 (1994).
Geibel et al., "Calcium-sensing receptor abrogates secretagogue-induced increases in intestinal net fluid secretion by enhancing cyclic nucleotide destruction", Proc. Natl. Acad. Sci. USA, vol. 103, No. 25, pp. 9390-9397 (2006).
GenBank: AAB24522.1, "CD8 beta chain isoform m betal (alternately spliced), partial [Homo sapiens]", May 8, 1993, 1 page.
GenBank: BAG64610.1, "Unnamed protein product [Homo sapiens]", Jul. 31, 2008 1 page.
Gogusev et al., "Depressed expression of calcium receptor in parathyroid gland tissue of patients with hyperparathyroidism", Kidney Int., vol. 51, No. 1, pp. 328-336 (1997).
Goodman, "Recent developments in the management of secondary hyperparathyroidism", Kidney Int., vol. 59, No. 3, pp. 1187-1201 (2001).
Goodman et al., "The calcimimetic agent AMG 073 lowers plasma parathyroid hormone levels in hemodialysis patients with secondary hyperparathyroidism", J. Am. Soc. Nephrol., vol. 13, No. 4, pp. 1017-1024 (2002).
Goto et al., "Heparin, protamine, and ionized calcium in vitro and in vivo", Anesth. Analg., vol. 64, No. 11, pp. 1081-1084 (1985).
Gray et al., "A selective epsilon-protein kinase C antagonist inhibits protection of cardiac myocytes from hypoxia-induced cell death", J. Biological Chemistry, vol. 272, No. 49, p. 30945-30951 (1997).
Gray et al., "Preservation of base-line hemodynamic function and loss of inducible cardioprotection in adult mice lacking protein kinase C epsilon", J. Biol. Chem., vol. 279, No. 5, p. 3596-3604 (2004).
Gregory et al., "Increased particulate partitioning of PKC epsilon reverses susceptibility of phospholamban knockout hearts to ischemic injury", J. Mol. Cell Cardiol., vol. 36, No. 2, pp. 313-318 (2004).
Gunn and Gaffney, "Clinical and laboratory features of calcium-sensing receptor disorders: a systematic review", Ann. Clin. Biochem., vol. 41, Pt. 6, pp. 441-458 (2004).
Gustafsson et al., "Discovery of a class of calcium sensing receptor positive allosteric modulators; 1-(benzothiazol-2-yl)-1-phenylethanols", Bioorg Med Chem Lett., vol. 20, No. 19, 5918-5921 (2010).
Handlogten et al., "Ca(2+)-sensing receptor is a promiscuous divalent cation sensor that responds to lead", Am. J. Physiol. Renal. Physiol., vol. 279, No. 6, pp. F1083-F1091 (2000).
Hauache et al., "Effects of a calcimimetic compound and naturally activating mutations on the human Ca2+ receptor and on Ca2+ receptor/metabotropic glutamate chimeric receptors", Endocrinology, vol. 141, No. 11, pp. 4156-4163 (2000).
Hebert, "Therapeutic use of calcimimetics", Annu. Rev. Med., vol. 57 pp. 349-364 (2006).
Helman et al., "Molecular cloning and primary structure of human chromogranin A (secretory protein I) cDNA", J. Biol. Chem., vol. 263, No. 23, pp. 11559-11563 (1988).
Hendy et al., "Chapter 3 calcium-sensing receptor and associated diseases", Prog. Mol. Biol. Transl. Sci., vol. 89, pp. 31-95 (2009).
Henley et al., "The calcimimetic AMG 641 abrogates parathyroid hyperplasia, bone and vascular calcification abnormalities in uremic rats", Eur. J. Pharmacol., vol. 616, No. 1-3, pp. 306-313 (2009).
Hofer, "Review series on the extracellular Ca(2+)-sensing receptor", J. Cell. Mol. Med., vol. 11, No. 5, pp. 906-907 (2007).
Hofer and Brown, "Extracellular calcium sensing and signalling", Nat. Rev. Mol. Cell Biol., vol. 4, No. 7, pp. 530-538 (2003).
Hong et al., "Effect of D-amino acid substitution on the stability, the secondary structure, and the activity of membrane-active peptide", Biochem. Pharmacol., vol. 58, No. 11, pp. 1775-1780 (1999).
Hool, "Protein kinase C isozyme selective peptides—A current view of what they tell us about location and function of isozymes in the heart", Current Pharmaceutical Design, vol. 11, p. 549-559 (2005).
Hrabak, "Common ligands of G-protein-coupled receptors and arginine-utilizing enzymes", Br. J. Pharmacol., vol. 147, No. 8, pp. 835-837 (2006).
Hu, "Allosteric modulators of the human calcium-sensing receptor: structures, sites of action, and therapeutic potentials", Endocr. Metab. Immune Disord. Drug Targets, vol. 8, No. 3, pp. 192-197.
Hu et al., "Indentification of acidic residues in the extracellular loops of the seven-transmembrane domain of the human Ca2+ receptor critical for response to Ca2+ and a positive allosteric modulator", J. Biol. Chem., vol. 277, 48, pp. 46622-46631 (2002).
Hu and Spiegel, "Structure and function of the human calcium-sensing receptor: insights from natural and engineered mutations and allosteric modulators", J. Cell Mol. Med., vol. 11, 5, pp. 908-922 (2007).
Hu et al., "Evidence for functional role of epsilonPKC isozyme in the regulation of cardiac CA(2+) channels", Am. J. Physiol. Heart Circ. Physiol., vol. 279, No. 6, p. H2658-H2664 (2000).
Huang et al., "Multiple Ca(2+)-binding sites in the extracellular domain of the Ca(2+)-sensing receptor corresponding to cooperative Ca(2+) response", Biochemistry., vol. 48, No. 2, pp. 388-398 (2009).
Hudecz et al., "Medium-sized peptides as built in carriers for biologically active compounds", Med. Res. Rev., vol. 25, No. 6, pp. 679-736 (2005).
Hundle et al., "An inhibitory fragment derived from protein kinase Cepsilon prevents enhancement of nerve growth factor responses by ethanol and phorbol esters", J. Biol. Chem., vol. 272, No. 23, p. 15028-15035 (1997).
Ikari et al., "Activation of a polyvalent cation-sensing receptor decreases magnesium transport via claudin-16", Biochim. Biophys. Acta, vol. 1778, No. 1, pp. 283-290 (2008).
Ikeno et al., "Impaired perfusion after myocardial infarction is due to reperfusion-induced deltaPKC-mediated myocardial damage", Cardiovasc. Res., vol. 73, No. 4, pp. 699-709 (2007).
Inagaki et al., "Tissue angiotensin during progression of ventricular hypertrophy to heart failure in hypertensive rats: differential effects on PKCε and PKCβ", J. Mol. Cell Cardiol., pp. 1-9 (2002).
Inagaki et al., "Additive protection of the ischemic heart ex vivo by combined treatment with delta-protein kinase C inhibitor and epsilon-protein kinase C activator", Circulation, vol. 108, p. 869-875 (2003).

(56) References Cited

OTHER PUBLICATIONS

Inagaki et al., "Inhibition of delta-protein kinase C protects against reperfusion injury of the ischemic heart in vivo", Circulation vol. 108, No. 19, p. 2304-2307 (2003).
Inagaki et al., "Cardioprotection by epsilon-protein kinase C activation from ischemia: Continuous delivery and antiarrythmic effect of an epsilon-protein kinase C-activating peptide", Circulation, vol. 111, No. 1, p. 44-50 (2005).
Inagaki and Mochly-Rosen, "DeltaPKC-mediated activation of epsilonPKC in ethanol-induced cardiac protection from ischemia", J. Mol. Cell Cardiol., vol. 39, No. 2, pp. 203-211 (2005).
Inagaki et al., "Epsilon protein kinase C as a potential therapeutic target for the ischemic heart", Cardiovasc. Res., vol. 70, No. 2, pp. 222-230 (2006).
International Search Report for PCT Patent Application No. PCT/US2008/051706 mailed Sep. 24, 2008, application now published as International Patent Publication No. WO2008/089491 A2 on Jul. 24, 2008.
International Search Report from related PCT Patent Application No. PCT/US2010/043792 mailed Apr. 26, 2011, application now published as International patent Publication No. WO2011/014707 on Feb. 3, 2011.
International Search Report from PCT Patent Application No. PCT/US2012/064717 mailed Mar. 7, 2013, application now published as International patent Publication No. WO2013/071262 on May 16, 2013.
Jaburek et al., "Mitochondrial PKC epsilon and mitochondrial ATP-sensitive K+ channel copurify and coreconstitute to form a functioning signaling module in proteoliposomes", Circ Res., vol. 99, pp. 878-883 (2006).
Jin et al., "Cardioprotection mediated by sphingosine-1-phosphate and ganglioside GM-1 in wild-type and PKC epsilon knockout mouse hearts", Am. J. Physiol. Heart Circ Physiol., vol. 282, No. 6, p. H1970-1977 (2002).
Johnson and Mochly-Rosen, "Inhibition of the spontaneous rate of contraction of neonatal cardiac myocyes by protein kinase C isozymes. A putative role for the epsilon isozyme", Circ. Res., vol. 76, No. 4, p. 654-663 (1995).
Johnson et al., "Prolonged phorbol ester treatment down-regulates protein kinase C isozymes and increases contraction rate in neonatal cardiac myocytes", Life Sci., vol. 57, No. 11, p. 1027-1038 (1995).
Johnson et al., "An improved permeabilization protocol for the introduction of peptides into cardiac myocytes. Application to protein kinase C research", Circ. Res., vol. 79, p. 1086-1099 (1996).
Johnson et al., "A protein kinase C translocation inhibitor as an isozyme-selective antagonist of cardiac function", J. Biol. Chem., vol. 271, No. 40, p. 24962-24966 (1996).
Johnston et al., "Protamine-induced hypocalcemia", Endocrinology, vol. 87, No. 6, pp. 1211-1217 (1970).
Joseph et al., "Hyperalgesic priming in the rat demonstrates marked sexual dimorphism", Pain, vol. 105, No. 1-2, pp. 143-150 (2003).
Kheifets et al., "Protein kinase C delta (deltaPKC)-annexin V interaction: a required step in deltaPKC translocation and function", J. Biol. Chem., vol. 281, No. 32, pp. 23218-23226 (2006).
Knauf et al., "Involvement of protein kinase Cepsilon (PKCepsilon) in thyroid cell death. A truncated chimeric PKCepsilon cloned from a thyroid cancer cell line protects thyroid cells from apoptosis", J. Biol. Chem., vol. 274, No. 33, p. 23414-23425 (1999).
Knauf et al., "Isozyme-specific abnormalities of PKC in thyroid cancer: Evidence for post-transciptional changes in PKC epsilon", J. Clin. Endocrinol. Metab., vol. 85, No. 5, p. 2150-2159 (2002).
Koponen et al., "Prevention of NMDA-Induced death of cortical neurons by inhibition of protein kinase Czeta", J. Neurochem., vol. 86, No. 2, p. 442-450 (2003).
Lagunoff et al., "Agents that release histamine from mast cells", Ann. Rev. Pharmacol. Toxicol., vol. 23, pp. 331-351 (1983).
Lange-Asschenfeldt et al., "Epsilon protein kinase C mediated ischemic tolerance requires activation of the extracellular regulated kinase pathway in the organotypic hippocampal slice", J. Cereb. Blood Flow Metab., vol. 24, No. 6, pp. 636-645 (2004).

Laudanna et al., "Evidence of zeta protein kinase C involvement in a polymorphic neutrophil integrin-dependent adhesion and chemotaxis", J. Biol. Chem., vol. 273, No. 46, p. 30306-30315 (1998).
Lee et al., "Allosteric activation of the extracellular Ca2+-sensing receptor by L-amino acids enhances ERK1/2 phosphorylation", Biochem. J., vol. 404, No. 1, pp. 141-149 (2007).
Li et al., "Protein kinase Cgamma mediates ethanol withdrawal hyper-responsiveness of NMDA receptor currents in spinal cord motor neurons", Br. J. Pharmacol., vol. 144, No. 3, pp. 301-307 (2005).
Lien et al., "Effects of cinacalcet on bone mineral density in patients with secondary hyperparathyroidism", Nephrol. Dial. Transplant, vol. 20, No. 6, pp. 1232-1237 (2005).
Liu et al., "Protein kinase C-epsilon is responsible for the protection of the preconditioning in rabbit cardiomyocytes", J. Mol. Cell Cardiol., vol. 31, No. 10, p. 1937-1948 (1999).
Luthman et al., "The hypocalcemic response to protamine as a measure of bone resorption", Acta Vet. Scand., vol. 14, No. 3, pp. 428-435 (1973).
Luthman and Korpe, "Vitamin D status and hyocalcemic response to protamine in exercised and non-exercised dairy cows", Acta Vet. Scand., vol. 34, No. 1, pp. 53-57 (1993).
Ma et al., "Characterization of highly efficacious allosteric agonists of the human calcium-sensing receptor", J. Pharmacol Exp. Ther., vol. 337, No. 1, pp. 275-284 (2011).
MacKay and Mochly-Rosen, "An inhibitor of p38 mitogen-activated protein kinase neonatal cardiac myocytes from ischemia", J. Biol. Chem., vol. 274, No. 10, p. 6272-6279 (1999).
MacKay and Mochly-Rosen, "Involvement of a p38 mitogen-activated protein kinase phosphatase in protecting neonatal rat cardiac myocytes from ischemia", J. Mol. Cell Cardiol., vol. 32, No. 8, p. 1585-1588 (2000).
MacKay and Mochly-Rosen, "Arachidonic acid protects neonatal rat cardiac myocytes from ischemic injury through epsilon protein kinaseC", Cardiovasc. Res., vol. 50, No. 1, p. 65-74 (2001).
MacKay and Mochly-Rosen, "Localization, anchoring, and function of protein kinase C isozymes in the heart", J. Mo. Cell. Cardiol., vol. 33, No. 7, p. 1301-1307 (2001).
MacLean, "KAI-4169: A Novel Calcium Sensing Receptor (CaSR) Agonist for the Treatment of CKD-MBD", TIDES Meeting Boston May 2011.
Magno et al., "The calcium-sensing receptor: a molecular perspective", Endocr. Rev., vol. 32, No. 1, pp. 3-30 (2011).
Malhotra et al., "PKC-(epsilon)-dependent survival signals in diabetic hearts", Am. J. Physiol. Heart Circ. Physiol., vol. 289, No. 4, pp. h1343-h1350 (2005).
Marie, "The calcium-sensing receptor in bone cells: a potential therapeutic target in osteoporosis", Bone, vol. 46, No. 3, pp. 571-576 (2010).
Marinovic et al., "Preconditioning by isoflurane induces lasting sensitization of the cardiac sarcolemmal adenosine triphosphate-sensitive potassium channel by a protein kinase C-delta-mediated mechanism", Anesthesiology, vol. 103, No. 3, pp. 540-547 (2005).
Martin et al., "KAI-4169, a Novel Peptide for the Treatment of Chronic Kidney Disease—Mineral and Bone Disorder, in a Phase I Study in Healthy Males", (Poster: FR-PO1238) American Society of Nephrology, Philadelphia, Nov. 2011.
Martin et al., "Characterization of KAI-169, A Novel Peptide for the Treatment of Chronic Kidney Disease Mineral and Bone Disorder, in a Single-dose Study in Hemodialysis Subjects", (Poster: FR-PO1256) American Society of Nephrology, Philadelphia, Nov. 2011.
Martin et al., "The Effect of KAI-4169, a Novel Treatment for Chronic Kidney Disease-Mineral and Bone Disorder, on Serum Phosphorus Kinetics Post-Hemodialysis", (Poster: FR-PO1232) American Society of Nephrology, Philadelphia, Nov. 2011.
McLarnon et al., "Aminoglycoside antibiotics induce pH-sensitive activation of the calcium-sensing receptor", Biochem. Biophys. Res. Commun., vol. 297, No. 1, pp. 71-77 (2002).

(56) References Cited

OTHER PUBLICATIONS

Mendoza et al., "Direct upregulation of parathyroid calcium-sensing receptor and vitamin D receptor by calcimimetics in uremic rats", Am. J. Physiol. Renal. Physiol., vol. 296, No. 3, pp. F605-F613 (2009).
Miller et al., "RACK1 regulates Src-mediated Sam68 and p190RhoGAP signaling", Oncogene, vol. 23, pp. 5682-5686 (2004).
Miyamae et al., "Activation of epsilon protein kinase C correlates with a cardioprotective effect of regular ethanol consumption", PNAS, vol. 95, No. 14, p. 8262-8267 (1998).
Mizobuchi et al., "Calcimimetic compound upregulates decreased calcium-sensing receptor expression level in parathyroid glands of rats with chronic renal insufficiency", J. Am. Soc. Nephrol., vol. 15, No. 10, pp. 2579-2587 (2004).
Mochly-Rosen et al., "A protein kinase C isozyme is translocated to cytoskeletal elements on activaion", Cell Regul., vol. 1, No. 9, p. 693-706 (1990).
Mochly-Rosen et al., "Intracellular receptors for activated protein kinase C: Identification of a binding site for the enzyme", J. Biol. Chem., vol. 266, No. 23, p. 14866-14868 (1991).
Mochly-Rosen et al., "Identification of intracellular receptor proteins for activated protein kinase C", PNAS, vol. 88, p. 3997-4000 (1991).
Mochly-Rosen et al., "p65 fragments homologous to the C2 region of protein kinase C, bind to the intracellular receptors for protein kinase C", Biochemistry, vol. 31, No. 35, p. 8120-8124 (1992).
Mochly-Rosen, "Localization of protein kinases by anchoring proteins: A theme in signal transduction", Science, vol. 268, p. 247-251 (1995).
Mochly-Rosen et al., "Intraction of protein kinase C with RACK1, a receptor for activated C-kinase: A role in beta protein kinase C mediated signal transduction", Biochem. Soc. Trans., vol. 23, No. 3, p. 596-600 (1995).
Mochly-Rosen and Gordon, "Anchoring proteins for protein kinase C: A means for isozyme selectivity", Faseb J., vol. 12, No. 1, p. 35-42 (1998).
Mochly-Rosen and Kauvar, "Modulating protein kinase C signal transduction", Adv. Pharmacol., vol. 44, p. 91-145 (1998).
Mochly-Rosen et al., "Cardiotrophic effects of protein kinase C epsilon: analysis by in vivo modulation of PKCepsilon translocation", Circ. Res., vol. 86, No. 11, p. 1173-1179 (2000).
Mochly-Rosen and Kauvar, "Pharmacological regulation of network kinetics by protein kinase C localization", Semin. Immunol., vol. 12, No. 1, p. 55-61 (2000).
Mochly-Rosen et al., "Spontaneous occurrence of an inhibitor of protein kinase C localization in a thyroid cancer cell line: role in thyroid tumorigenesis", Adv. Enzyme Regul., vol. 41, p. 87-97 (2001).
Moe et al., "R-568 reduces ectopic calcificaton in a rat model of chronic kidney disease-mineral bone disorder (CKD-MBD)", Nephrol. Dial. Transplant, vol. 24, No. 8, pp. 2371-2377 (2009).
Mukherjee et al., "Protein kinase C isoform activation and endothelin-1 mediated defects in myocyte contractility after cardioplegic arrest and reperfusion", vol. 114, Suppl. 1, pp. 1308-1313 (2006).
Mun et al., "A double mutation in the extracellular Ca2+-sensing receptor's venus flytrap domain that selectively disables L-amino acid sensing", J. Biol. Chem., vol. 280, No. 32, pp. 29067-29072 (2005).
Mun et al., "The Venus Fly Trap domain of the extracellular Ca2+-sensing receptor is required for L-amino acid sensing", J. Biol. Chem., vol. 279, No. 50, pp. 51739-51744 (2004).
Murriel and Mochly-Rosen, "Opposing roles of delta and epsilonPKC in cardiac ischemia and reperfusion: Targeting the apoptic machinery", Arch. Biochem. Biophys., vol. 420, No. 2, p. 246-254 (2003).
Murriel et al., "Protein kinase Cdelta activation induces apoptosis in response to cardiac ischemia and reperfusion damage: A mechanism involving BAD and the mitochondria", J. Biol. Chem., vol. 279, No. 46, p. 47985-47991 (2004).
Nagano and Nemeth, "Functional proteins involved in regulation of intracellular Ca(2+) for drug development: the extracellular calcium receptor and an innovative medical approach to control secondary hyperparathyroidism by calcimimetics", J. Pharmacol. Sci. vol. 97, pp. 355-360 (2005).
Nagano, "Pharmacological and clinical properties of calcimimetics: calcium receptor activators that afford an innovative approach to controlling hyperparathyroidism", Pharmacol. Ther., vol. 109, No. 3, pp. 339-365 (2006).
Navarro et al., "Toxicological and pharmacological effects of D-arginine", Basic Clin, Pharmacol. Toxicol., vol. 97, No. 3, pp. 149-154 (2005).
Nemeth et al., "Calcimimetics with potent and selective activity on the parathyroid calcium receptor", PNAS, vol. 95 pp. 4040-4045 (1998).
Nemeth and Fox, "Calcimimetic Compounds: a Direct Approach to Controlling Plasma Levels of Parathyroid Hormone in Hyperparathyroidism", Trends Endocrinol. Metab., vol. 10, No. 2, pp. 66-71 (1999).
Nemeth, "Pharmacodynamics of the type II calcimimetic compound cinacalcet HCl", J. Pharm. Exp. Ther., vol. 38, pp. 627-635 (2004).
Office Action Mailed Mar. 9, 2011 with respect to U.S. Appl. No. 11/941,857.
Parada et al., "Transient attenuation of protein kinase Cepsilon can terminate a chronic hyperalgesic state in the rat", Neuroscience, vol. 120, No. 1, pp. 219-226 (2003).
Pace et al., "Dimerization of the calcium-sensing receptor occurs within the extracellular domain and is eliminated by Cys → Ser mutations at Cys101 and Cys236", J. Biol. Chem., vol. 274, vol. 17, pp. 11629-11934 (1999).
Parada et al., "Chronic hyperalgesic priming in the rat involves a novel interaction between cAMP and PKCepsilon second messenger pathways", Pain, vol. 113, No. 1-2, pp. 185-190 (2005).
Pastori et al., "Delivery of proteins and peptides into live cells by means of protein transduction domains: potential application to organ and cell transplantation", Transplantation, vol. 77, No. 11, p. 1627-1631 (2004).
Pickthorn et al., "PK/PD Modeling of Transdermal Delivery of a Novel Peptide. KAI-4169, for the Treatment of Chronic Kidney Disease-Bone and Mineral Disorder (CKD-MBD)", (Poster: FR-PO1245) American Society of Nephrology, Philadelphia, Nov. 2011.
Pitchford et al., "Nicotinic acetylcholine receptor desensitization is regulated by activation-induced extracellular adenosine accumulation", J. Neurosci, vol. 12, No. 11, p. 4540-4544 (1992).
Pologe et al., "Primary structure and subcellular localization of the knob-associated histidine-rich protein of Plasmodium falciparum", PNAS USA, vol. 84, pp. 7139-7143 (1987).
Potts et al., "*Protamine: a powerful in vivo inhibitor of bone resorption*", Calcif. Tissue Int., vol. 36, vol. 2, pp. 189-193 (1984).
Price et al., "Artery calcification in uremic rats is increased by a low protein diet and prevented by treatment with ibandronate", Kidney Int., vol. 70, No. 9, pp. 1577-1583 (2006).
Quinn et al., "Ca2+-sensing receptor: a target for polyamines", Am. J. Physiol., vol. 273, No. 4, Pt. 1, pp. C1315-C1323 (1997).
Ramanathan et al., "Targeted PEG-based bioconjugates enhance the cellular uptake and transport of a HIV-1 TAT nonapeptide", J. Contr. Rel., Vo. 77, No. 3, pp. 199-212 (2001).
Raval et al., "Epsilon PKC is required for the induction of tolerance by ischemic and NMDA-mediated preconditioning in the organotypic hippocampal slice", J. Neirosci., vol. 23, No. 2, p. 384-391 (2003).
Raval et al., "Protein kinase C delta cleavage initiates an aberrant signal transduction pathway after cardiac arrest and oxygen glucose deprivation", J. Cereb. Blood Flow Metab., vol. 25, No. 6, pp. 730-741 (2005).
Ray et al., "Elucidation of the role of peptide linker in calcium-sensing receptor activation process", J. Biol. Chem., vol. 282, No. 8, pp. 5310-5317 (2007).
Ray et al., "The role of cysteines and charged amino acids in extracellular loops of the human Ca(2+) receptor in cell surface expression and receptor activation processes", Endocrinology, vol. 145, No. 8, pp. 3892-3903 (2004).

(56) References Cited

OTHER PUBLICATIONS

Ray et al., "Identification of the cysteine residues in the amino-terminal extracellular domain of the human Ca(2+) receptor critical for dimerization. Implications for function of monomeric Ca(2+) receptor", J. Biol. Chem., vol. 274, No. 39, pp. 27642-27650 (1999).
Ray and Northup, "Evidence for distinct cation and calcimimetic compound (NPS 568) recognition domains in the transmembrane region of the human Ca2+ receptor", J. Biol. Chem., vol. 277, No. 21, pp. 18908-18913 (2002).
Rey et al., "Amino acid-stimulated Ca2+ oscillations produced by the Ca2+ sensing receptor are mediated by a phospholipase C/inositol 1,4,5-trisphosphate-independent pathway that requires G12, Rho, filamin-A, and the actin cytoskeleton", J. Biol. Chem., vol. 280, No. 24, pp. 22875-22882 (2005).
Riccardi et al., "Novel regulatory aspects of the extracellular Ca2+-sensing receptor, CaR", Pflugers Arch., vol. 458, No. 6, pp. 1007-1022 (2009).
Riccardi and Gamba, "The many roles of the calcium-sensing receptor in health and disease", Arch. Med. Res., vol. 30, No. 6, pp. 436-448 (1999).
Ridge et al., "Dopamine-induced exocytosis of Na,K-ATPase is dependent on activation of protein kinase C-epsilon and -delta", Mol. Biol. Cell., vol. 13, No. 4, p. 1381-1389 (2002).
Robia et al., "Novel determinant of PKC-epsilon anchoring at cardiac Z-lines", Am. J. Physiol. Heart Circ. Physiol., vol. 289, No. 5, pp. h1941-h1950 (2005).
Rodriguez et al., "Characterization of the binding and phosphorylation of cardiac calsequestrin by epsilon protein kinase C", FEBS Lett., vol. 454, No. 3, p. 240-246 (1999).
Rodriguez et al., "RACK1, a protein kinase C anchoring protein, coordinates the binding of activated protein kinase C and select pleckstrin homology domains in vitro", Biochemistry, vol. 38, No. 42, p. 13787-13794 (1999).
Rodriguez et al., "The calcium-sensing receptor: a key factor in the pathogenesis of secondary hyperparathyroidism", Am. J. Physiol. Renal Physiol., vol. 288, No. 2, pp. F253-F264 (2005).
Ron and Mochly-Rosen, "Agonists and antagonists of protein kinase C function, derived from its binding proteins", J. Biol. Chem., vol. 269, No. 34, p. 21395-21398 (1994).
Ron and Mochly-Rosen, "An autoregulatory region in protein kinase C: The psuedoanchoring site", PNAS, vol. 92, No. 2, p. 492-496 (1995).
Ron et al., "Cloning of an intracellular receptor for protein kinase C: A homolog of the beta subunit of G proteins", PNAS, vol. 91, No. 3, p. 839-843 (1994).
Ron et al., "C2 region-derived peptides inhibit translocation and function of beta protein kinase C in vivo", J. Biol. Chem., vol. 270, No. 41, p. 24180-24187 (1995).
Saidak et al., "Agonists and allosteric modulators of the calcium-sensing receptor and their therapeutic applications", Mol. Pharmacol., vol. 76, No. 6, pp. 1131-1144. (2009).
Sajid-Crockett et al., "Cinacalcet for the treatment of primary hyperparathyroidism", Metabolism, vol. 57, No. 4, pp. 517-521 (2008).
Satoh et al., "PKC-delta and -epsilon regulate NF-kappaB activation induced by cholecystokinin and TNF-alpha in pancreatic acinar cells", Am. J. Physiol. Gastrointest. Liver Physiol., vol. 287, No. 3, p. G582-G591 (2004).
Satoh et al., "Ethanol sensitizes NF-κB activation inpancreatic acinar cells through effects on protein kinase C epsilon", Articles in press, Am. J. Physiol. Gastrointest. Liver Physiol., doi:10.1152/ajpgi.00579 Apr. 6, 2006.
Schechtman et al., "Adaptor proteins in protein kinase C-mediated signal transduction", Oncogene, vol. 20, No. 44 p. 6339-6347 (2001).
Schechtman and Mochly Rosen, "Isozyme-specific inhibitors and activators of protein kinase C", Methods Enxymol., vol. 35, pp. 470-489 (2002).
Schechtman et al., "Overlay method for detecting protein-protein interactions", Methods Mol. Biol., vol. 223, p. 351-357 (2003).
Schechtman et al., "Glutathione S-transferase pull-down assay", Methods Mol. Biol., vol. 233, No. 345-350 (2003).
Shannon et al., "Novel cyclic peptide inhibits intercellular adhesion molecule-1-mediated cell aggregation", J. Peptide Res., vol. 58, No. 2, pp. 140-150 (2001).
Schechtman et al., "A critical intramolecular interaction for protein kinase Cepsilon translocation", J. Biol. Chem., vol. 279, No. 16, p. 15831-15840 (2004).
Shen et al., "The PK/PD Relationship of a Novel Peptide, KAI-4169 Following Single-Dose Administration to Healthy Young Males ", Endocrine Society 93rd Annual Meeting (ENDO 2011), Boston Jun. 4-8, 2011 (Endocr Rev 32: P1-23) (2011).
Shimoni and Liu, "Role of PKC in autocrine regulation of rat ventricular K+ currents by angiotensin and endothelin", Am. J. Physiol. Heart Circ. Physiol., vol. 284, No. 4, pp. h1168-h1181 (2003).
Shoback et al., "The calcimimetic cinacalcet normalizes serum calcium in subjects with primary hyperparathyroidism", J. Clin. Endocrinol. Metab., vol. 88, No. 12, pp. 5644-5649 (2003).
Shoback et al., "Relationship between parathyroid hormone secretion and cytosolic calcium concentration in dispersed bovine parathyroid cells", Proc. Natl. Acad. Sci. USA., vol. 81, No. 10, pp. 3113-3117 (1984).
Shumilla et al., "Ethanol withdrawal-associated allodynia and hyperalgesia: age-dependent regulation by protein kinase C epsilon and gamma isoenzymes", J. Pain, vol. 6, No. 8, pp. 535-549 (2005).
Simon et al., "Characterization of PKC2 a gene encoding a second protein kinase C isotype of *Saccharomyces cerevisiae*", Curr. Biol., vol. 3, No. 12, p. 813-821 (1993).
Simon et al., "The identification and purification of a mammalian-like protein kinase C in the yeast *Saccharomyces cerevisiae*", Proc. R. Soc. Lond., vol. 243, No. 1307, p. 165-171 (1991).
Smith and Mochly-Rosen, "Inhibition of protein kinase C function by injection of intracellular receptors for the enzyme", Biochem. Biophys. Res. Commun., vol. 188, No. 3, p. 1235-1240 (1992).
Smith et al., "The HIV nef protein associates with protein kinase C theta", J. Biol. Chem., vol. 271, No. 28, p. 16753-16757 (1996).
Souqiyyeh and Shaheen, "Survey of altitudes of physicians toward the current evaluation and treatment of chronic kidney disease-mineral and bone disorder (CKD-MBD)", Saudi J. Kidney Dis. Transpl., vol. 21, No. 1, pp. 93-101 (2010).
Souroujon and Mochly-Rosen, "Peptide modulators of protein-protein interactions in intracellular signaling", Nat Biotechnol., vol. 16, No. 10, p. 919-924 (1998).
Souroujon et al., "State-specific monoclonal antibodies identify an intermediate state in epsilon protein kinase C activation", J. Biol. Chem., vol. 279, No. 17, p. 17617-17624 (2004).
Spormann et al., "Carboxypeptidase yscS: gtene structure and function of the vacular enzyme", Eur. J. Biochem., vol. 197, pp. 399-405 (1991).
Stebbins and Mochly-Rosen, "Binding specificity for RACK1 resides in the V5 region of beta II kinase C", J. Biol. Chem., vol. 276, No. 32, p. 29644-29650 (2001).
Svara, "Chronic kidney disease-mineral and bone disorder (ckd-mbd): a new term for a complex approach", J. Ren. Care, vol. 35, Suppl. 1, pp. 3-6 (2009).
Sweitzer et al., "Exaggerated Nociceptive responses on morphine withdrawal: Roles of protein kinase C epsilon and gamma", Pain, No. 110, No. 1-2, p. 281-289 (2004).
Sweitzer et al., "Protein kinase C epsilon and gamma: Involvement in formalin-induced nociception in neonatal rats", J. Pharmacol. Exp. Ther., vol. 309, No. 2, p. 616-625 (2004).
Szabo et al., "RSA 2004: combined basic research satellite symposium—session three: alcohol and mitochondrial metabolism: at the crossroads of life and death", Alcohol Clin. Exp. Res., vol. 29, No. 9, pp. 1749-1752 (2005).
Tanaka et al., "Suppression of graft coronary artery disease by a brief treatment with a selective epsilonPKC activator and a deltaPKC inhibitor in murine cardiac allografts", Circulation, vol. 110, No. 11, Suppl. 1, p. ii194-199 (2004).

(56) References Cited

OTHER PUBLICATIONS

Tanaka et al., "Inhibition of heart transplant injury and graft coronary artery disease after prolonged organ ischemia by selective protein kinase C regulators", J. Thorac. Cardiovasc. Surg., vol. 129, No. 5, pp. 1160-1167 (2005).
Trivedi et al., "Recent updates on the calcium-sensing receptor as a drug target", Curr. Med. Chem., vol. 15, No. 2, pp. 178-186 (2008).
Urenãand Frazão, "Calcimimetic agents: Review and perspectives", Kidney International, vol. 63, Supplement 85, pp. S91-S96 (2003).
Vallentin and Mochly-Rosen, "RBCK1, a protein kinase Cbetal (PKCbetal)-interacting protein, regulates PKCbeta-dependent function", J. Biol. Chem., vol. 282, No. 3, pp. 1650-1657 (2007).
Van Baal et al., "Translocation of diacylglycerol kinase theta from cytosol to plasma membrane in response to activation of G protein-coupled receptors and protein kinase C", vol. 280, No. 11, pp. 9870-9878 (2005).
Wada et al., "Calcimimetic NPS R-568 prevents parathyroid hyperplasia in rats with severe secondary hyperparathyroidism", Kidney Int., vol. 57, No. 1, pp. 50-58 (2000).
Walter et al., "Preclinical PK and PD relationship for KAI-4169, a novel peptide agonist of the calcium sensing receptor", Endocirine Society, 93$^{rd}$ Annual Meeting, Boston Jun. 4-8, 2011, Endocr. Rev., vol. 32, pp. P1-P198 (2011).
Walter et al., "KAI-4169, a Novel Peptide Agonist of the Calcium Sensing Receptor, Suppresses Parathyroid Hormone, Parathyroid Gland Hyperplasia and Ectopic Calcification in a Rodent Model of Chronic Renal Dysfunction", (Poster: FR-PO1222) American Society of Nephrology, Philadelphia, Nov. 2011.
Wang et al., "Cell-specific role for epsilon- and beta-protein kinase C isozymes in protecting cortical neurons and astrocytes from ischemia-like injury", Neuropharmacology, p. 47, No. 1, p. 136-145 (2004).
Ward et al., "Disulfide bonds in the extracellular calcium-polyvalent cation-sensing receptor correlate with dimer formation and its response to divalent cations in vitro", J. Biol. Chem., vol. 273, No. 23, pp. 14476-14483 (1998).
Ward et al., "Aminoglycosides induce acute cell signaling and chronic cell death in renal cells that express the calcium-sensing receptor", J. Am. Soc. Nephrol., vol. 16, No. 5, pp. 1236-1244 (2005).
Way et al., "Identification of PKC-isophorm-specific biological actions using pharmacological approaches", TIPS, vol. 21, No. 5, p. 181-187 (2000).
Wesseling-Perry and Salusky, "Phosphate binders, vitamin D and calcimimetics in the management of chronic kidney disease-mineral bone disorders (CKD-MBD) in children", Pediatr. Nephrol., vol. 28, No. 4, pp. 617-625 (2013).
Wu et al., "Epsilon protein kinase C in pathological myocardial hypertrophy. Analysis by combined transgenic expression of translocation modifiers and Galphaq", J. Biol. Chem., vol. 275, No. 39, pp. 29927-29930 (2000).
Xiao et al., "PKC isozyme selective regulation of cloned human cardiac delayed slow rectifier K current", Biochem. Biophys. Res. Commun., vol. 306, No. 4, p. 1019-1025 (2003).
Xiao et al., "Evidence for functional role of epsilonPKC isozyme in the regulation of cardiac Na(+) channels", Am. J. Physiol. Cell. Physiol., vol. 281, No. 5, p. C1477-1486 (2001).
Yang et al., "Discovery and structure-activity relationships of trisubstituted pyrimidines/pyridines as novel calcium-sensing receptor antagonists", J. Med. Chem., vol. 52, No. 4, pp. 1204-1208 (2009).
Ye et al., "Amyloid-beta proteins activate Ca(2+)-permeable channels through calcium-sensing receptors", J. Neurosci. Res., vol. 47, No. 5, pp. 547-554 (1997).
Yedovitzky et al., "Translocation inhibitors define specificity of protein kinase C isoenzymes in pancreatic beta-cells", J. Biol. Chem., vol. 272, No. 3, p. 1417-1420 (1997).
Young and Rozengurt, "Amino acids and Ca2+ stimulae different patterns of Ca2+ oscillations through the Ca2+-sensing receptor", Am. J. Physiol. Cell Physiol., vol. 282, No. 6, pp. C1414-c1422 (2002).
Yu et al., "Two-dimensional NMR studies and secondary structure of cobrotoxin in aqueous solution", Eur. J. Biochem., vol. 193, pp. 789-799 (1990).
Zhang et al., "C2 region-derived peptides of beta-protein kinase C regulates cardiac Ca2+ channels", Circ. Res., vol. 80, No. 5, p. 720-729 (1997).
Zhang et al., "L-phenylalanine and NPS R-467 synergistically potentiate the function of the extracellular calcium-sensing receptor through distinct sites", J. Biol. Chem., vol. 277, No. 37, pp. 33736-33741 (2002).
Zhang et al., Three adjacent serines in the extracellular domains of the CaR are required for L-amino acid-mediated potentiation of receptor function, J. Biol. Chem., vol. 277, No. 37, pp. 33727-33735 (2002).
Zhang et al., "The extracellular calcium-sensing receptor dimerizes through multiple types of intermolecular interactions", J. Biol. Chem., vol. 276, No. 7, pp. 5316-5322 (2001).
Zhou et al., "Deifferential activation of protein kinase C isozymes by phorbol ester and collagen in human skin microvascular endothelial cells", J. Invest. Dermatol., vol. 107, No. 2, p. 248-252 (1996).
Zhang et al., "Quantitative assessment of the cell penetrating properties of RI-Tat-9: Evidence for a celltype-specific barrier at the plasma membrane of epithelial cells", Molecular Pharmaceutics, vol. 1, No. 2,pp. 145-155 (2004).
Disanto et al., "Transcriptional diversity at the duplicated human CD8 beta loci", Eur. J. Immunol., vol. 23, No. 2, pp. 320-326 (1993).

THERAPEUTIC AGENTS FOR REDUCING PARATHYROID HORMONE LEVELS

CROSS-REFERENCE TO RELATED APPLICATIONS

This application is a continuation of U.S. application Ser. No. 12/846,724, filed Jul. 29, 2010, now allowed, which claims the benefit of U.S. Provisional Application No. 61/229,695, filed Jul. 29, 2009, and of U.S. Provisional Application No. 61/255,816, filed Oct. 28, 2009, and of U.S. Provisional Application No. 61/313,635, filed Mar. 12, 2010. Each of these applications is incorporated herein by reference in its entirety.

REFERENCE TO SEQUENCE LISTING, TABLE OR COMPUTER PROGRAM

A Sequence Listing is being submitted electronically via EFS in the form of a text file, created Mar. 4, 2015, and named "09150802558017US05.txt" (87,919 bytes), the contents of which are incorporated herein by reference in their entirety.

TECHNICAL FIELD

The current subject matter relates to compounds with activity to decrease parathyroid hormone (PTH) levels, to pharmaceutical compositions comprising the compounds, and to the use of such compounds and compositions in methods of treatment, including but not limited to treating hypercalcemia or hyperparathyroidism or modulating in vivo PTH levels.

BACKGROUND

Calcium homeostasis is the mechanism by which the body maintains adequate calcium levels. The process is highly regulated, and involves a complex interplay between calcium absorption, transport, storage in bones, deposition in other tissues, and excretion. PTH is a regulator of circulating calcium levels, and functions to increase the concentration of calcium in the blood by enhancing the release of calcium from bone through the process of bone resorption; increasing reabsorption of calcium from the renal tubules; and enhancing calcium absorption in the intestine by increasing the production of 1,25-$(OH)_2$ vitamin D, the active form of vitamin D. PTH also stimulates phosphorus excretion from the kidney, and increases release from bone.

PTH secretion is regulated by the calcium sensing receptor (CaSR), a G-protein coupled receptor expressed by several cell types on the surface of parathyroid cells, which detects small fluctuations in the concentration of extracellular calcium ion ($Ca^{2+}$) and responds by altering the secretion of PTH. Activation of the CaSR by $Ca^{2+}$ inhibits PTH secretion within seconds to minutes through inhibition of vesicular transport, and this process may be modulated by protein kinase C (PKC) phosphorylation of the receptor. The CaSR is also expressed on osteoblasts and in the kidney, where it regulates renal $Ca^{2+}$ excretion.

In addition, PTH regulates phosphorus homeostasis. PTH stimulates the parathyroid hormone receptor 1 (PTHR1) on both apical (brush border membrane) and basolateral membranes of cells in the GI tract. PTHR1 stimulation leads to an increase in urinary excretion of phosphate (Pi) as a consequence of reduction by internalization of the renal $Na^+$/phosphate (NaPi-IIa) co-transporter on the brush border membrane.

PTH is also involved in the regulation of osteoblasts and osteoclasts in bone. PTH increases circulating $Ca^{2+}$ by increasing bone resorption and renal reabsorption of calcium. PTH stimulates osteoblasts to produce RANK ligand (RANKL), which binds to the RANK receptor and activates the osteoclasts, leading to an increase in bone resorption and an increase in serum $Ca^{2+}$. Osteoprotegerin (OPG) is a decoy receptor for RANKL which blocks bone resorption. Osteoporosis is caused by an imbalance between the processes of bone resorption by osteoclasts and bone formation by osteoblasts.

The human body contains approximately 1 kg of calcium, 99% of which resides in bone. Under normal conditions, circulating calcium ion ($Ca^{2+}$) is tightly maintained at a level of about 9 to 10 mg/dL (i.e., 2.25-2.5 mmol/L; ~600 mg). Approximately 1 g of elemental calcium ($Ca^{2+}$) is ingested daily. Of this amount, approximately 200 mg/day is absorbed, and 800 mg/day is excreted. In addition, approximately 500 mg/day is released by bone resorption or is deposited into bone. About 10 g of $Ca^{2+}$ is filtered through the kidney per day, with about 200 mg appearing in the urine, and the remainder being reabsorbed.

Hypercalcemia is an elevated calcium level in the blood. Acute hypercalcemia can result in gastrointestinal (anorexia, nausea, vomiting); renal (polyuria, polydipsia), neuro-muscular (depression, confusion, stupor, coma) and cardiac (bradycardia, first degree atrio-ventricular) symptoms. Chronic hypercalcemia is also associated with gastrointestinal (dyspepsia, constipation, pancreatitis); renal (nephrolithiasis, nephrocalcinosis), neuro-muscular (weakness) and cardiac (hypertension block, digitalis sensitivity) symptoms. Abnormal heart rhythms can result, and EKG findings of a short QT interval and a widened T wave suggest hypercalcemia. Hypercalcemia may be asymptomatic, with symptoms more commonly occurring at high calcium levels (12.0 mg/dL or 3 mmol/l). Severe hypercalcemia (above 15-16 mg/dL or 3.75-4 mmol/l) is considered a medical emergency: at these levels, coma and cardiac arrest can result.

Hypercalcemia is frequently caused by hyperparathyroidism, leading to excess bone resorption and elevated levels of serum calcium. In primary sporadic hyperparathyroidism, PTH is overproduced by a single parathyroid adenoma; less commonly, multiple adenomas or diffuse parathyroid gland hyperplasia may be causative. Increased PTH secretion leads to a net increase in bone resorption, with release of $Ca^{2+}$ and phosphate (Pi). PTH also enhances renal reabsorption of $Ca^{2+}$ and inhibits reabsorption of phosphate (Pi), resulting in a net increase in serum calcium and a decrease in phosphate.

Secondary hyperparathyroidism occurs when a decrease in circulating levels of $Ca^{2+}$ level stimulates PTH secretion. One cause of secondary hyperparathyroidism is chronic renal insufficiency (also referred to as chronic kidney disease or CKD), such as that in renal polycystic disease or chronic pyelonephritis, or chronic renal failure, such as that in hemodialysis patients (also referred to as end stage renal disease or ESRD). Excess PTH may be produced in response to hypocalcemia resulting from low calcium intake, GI disorders, renal insufficiency, vitamin D deficiency, and renal hypercalciuria. Tertiary hyperparathyroidism may occur after a long period of secondary hyperparathyroidism and hypercalcemia.

Malignancy is a common cause of non-PTH mediated hypercalcemia. Hypercalcemia of malignancy, is an uncommon but severe complication of cancer, affecting between 10% and 20% of cancer patients, and may occur with both solid tumors and leukemia. The condition has an abrupt onset and has a very poor prognosis, with a median survival of only six weeks. Growth factors (GF) regulate the production of parathyroid hormone-related protein (PTHrP) in tumor cells. Tumor cells may be stimulated by autocrine GF to increase production of PTHrP, leading to enhanced bone resorption. Tumor cells metastatic to bone may also secrete PTHrP, which can resorb bone and release additional GF which in turn act in a paracrine manner to further enhance PTHrP production.

Accordingly, compounds with activity to, for example, modulate PTH levels and/or calcium levels in vivo are desired.

BRIEF SUMMARY

In one aspect, a compound, comprising the formula $$X_1-X_2-X_3-X_4-X_5-X_6-X_7$$

is provided, wherein $X_1$ is a subunit comprising a thiol-containing group; $X_5$ is a cationic subunit; $X_6$ is a non-cationic subunit; $X_7$ is a cationic subunit; and at least one, preferably two, of $X_2$, $X_3$ and $X_4$ is/are independently a cationic subunit; and wherein the compound has activity to decrease parathyroid hormone concentration. In one embodiment, the decrease in parathyroid hormone concentration is a decrease in blood or plasma parathyroid hormone concentration in a subject treated with the compound relative to the blood or plasma parathyroid hormone concentration in the subject prior to treatment. In another embodiment, the decrease in parathyroid hormone concentration is achieved in the absence of a histamine response.

In another embodiment $X_3$ and $X_4$ are non-cationic while $X_1$, $X_5$, $X_6$ and $X_7$ are cationic.

In one embodiment, the $X_1$ subunit is a thiol-containing amino acid residue. In another embodiment, the thiol group of the $X_1$ subunit is an organic thiol-containing moiety.

In another embodiment, when the $X_1$ subunit is a thiol-containing amino acid residue, it is selected from the group consisting of L-cysteine, D-cysteine, glutathione, n-acetylated cysteine, homocysteine and pegylated cysteine.

In yet another embodiment, the organic thiol-containing moiety is selected from thiol-alkyl, or thioacyl moieties such as 3-mercaptopropyl or 3-mercaptopropionyl, mercaptopropionic acid, mercaptoacetic acid, thiobenzyl, or thiopropyl. In still another embodiment, the organic-thiol-containing moiety is mercaptopropionic acid.

In still another embodiment, the $X_1$ subunit is modified chemically to comprise an acetyl group, a benzoyl group, a butyl group, or another amino acid such as acetylated-beta-alanine.

In yet another embodiment, when the $X_1$ subunit comprises a thiol moiety, the $X_1$ subunit is joined by a covalent linkage to a second thiol moiety.

In another embodiment, the formula $X_1$-$X_2$-$X_3$-$X_4$-$X_5$-$X_6$-$X_7$ is comprised of a contiguous sequence of amino acid residues (designated herein as $(X_{aa1})$-$(X_{aa2})$-$(X_{aa3})$-$(X_{aa4})$-$(X_{aa5})$-$(X_{aa6})$-$(X_{aa7})$ SEQ ID NO:1) or a sequence of organic compound subunits (non-amino acid residues).

In another embodiment, the contiguous sequence of amino acid residues is a contiguous sequence of L-amino acid residues, a contiguous sequence of D-amino acid residues, a contiguous sequence of a mixture of L-amino acid residues and D-amino acid residues, or a mixture of amino acid residues and non-natural amino acid residues.

In another embodiment, the contiguous sequence of amino acid residues is linked to a compound to facilitate transport across a cell membrane. In another embodiment, the contiguous sequence of amino acid residues is linked to a compound that enhances delivery of the sequence into or across one or more layers of tissue.

In another embodiment, the contiguous sequence of amino acid residues is contained within a sequence of amino acid residues from 8-50 amino acid residues, 8-40 amino acid residues, 8-30 amino acid residues or 8-20 amino acid residues in length. In yet another embodiment, the contiguous sequence of amino acid residues is contained within a sequence of amino acid residues from 8-19 amino acid residues, 8-18 amino acid residues, 8-17 amino acid residues, 8-16 amino acid residues, 8-15 amino acid residues, 8-14 amino acid residues, 8-13 amino acid residues, 8-12 amino acid residues, 8-11 amino acid residues, 8-10 amino acid residues, or 8-9 amino acid residues in length.

In another embodiment, the $X_3$ subunit is a cationic amino acid residue.

In another embodiment, the $X_2$ subunit is a non-cationic amino acid residue, and in another embodiment, the $X_4$ subunit is a non-cationic amino acid residue. In one embodiment, the non-cationic amino acid residue is a D-amino acid.

In another embodiment, $X_3$ and $X_4$ are cationic D-amino acid residues.

In another embodiment, the $X_5$ subunit is a D-amino acid residue.

In another aspect, the contiguous sequence in any of the described compounds is covalently attached via the thiol-containing group in the $X_1$ subunit to a second contiguous sequence. For example, the second contiguous sequence can be identical to the contiguous sequence (to form a dimer), or can be non-identical, as would be the case when attached to a moiety that facilitates transfer of the contiguous sequence across a cell membrane.

In another aspect, a conjugate comprised of the peptide carrrar (SEQ ID NO:2) is provided, where the peptide is conjugated at its N-terminal residue to a Cys residue.

In one embodiment, the peptide is chemically modified at the N-terminus, the C-terminus, or both.

In another embodiment, the N-terminus of the peptide is chemically modified by acetylation and the C-terminus is chemically modified by amidation.

In another embodiment, the conjugate is Ac-c(C)arrrar-NH$_2$ (SEQ ID NO:3).

In another aspect, a method of treating secondary hyperparathyroidism (SHPT) in a subject is contemplated, wherein a compound as described herein is provided to the subject. In various embodiments, the subject can be suffering from chronic kidney disease or other condition.

In another aspect, a method of decreasing parathyroid hormone in a subject is contemplated, wherein a compound as described herein is provided to the subject.

In another aspect, a treatment regimen is provided, the regimen comprising providing a compound according to any of those described herein, in combination with a second agent.

In one embodiment, the second therapeutic agent is vitamin D, a vitamin D analog or cinacalcet hydrochloride.

In any of the aspects or embodiments described herein, any one or more of the sequences is contemplated to be individually excepted or removed from the scope of the claims. In certain embodiments, the peptides identified by any one or more of SEQ ID NOs: 162-182, individually or in any combination, are excluded from the claimed compounds, compositions and methods.

Figure 1:
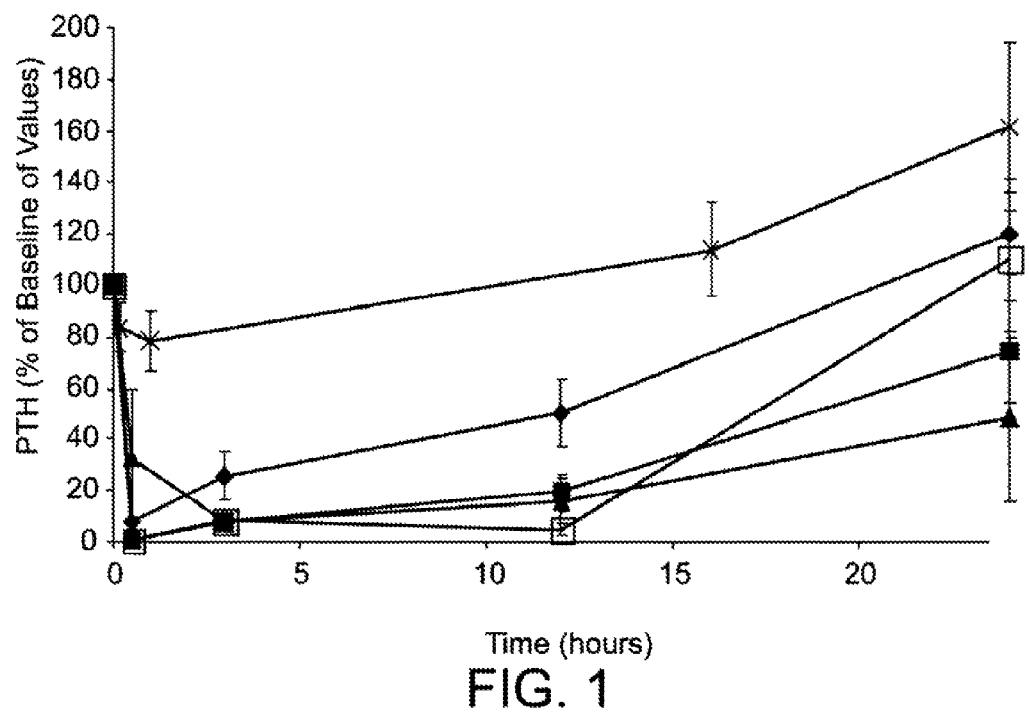
FIG. 1 is a graph of parathyroid hormone level, as percent of the baseline pre-dose value, as a function of time, in hours, in rats with acute renal insufficiency (1K1C model), where the rats were dosed with Ac-crrrr-NH$_2$ (SEQ ID NO:4, diamonds), Ac-crrrrr-NH$_2$ (SEQ ID NO:5, closed squares), Ac-crrrrrr-NH$_2$ (SEQ ID NO:6, triangles), Ac-crrrrrrr-NH$_2$ (SEQ ID NO:7, open squares), or saline control (x symbols)

The present subject matter may be understood more readily by reference to the following detailed description of the preferred embodiments and the examples included herein.

DETAILED DESCRIPTION

I. Definitions

Within this application, unless otherwise stated, definitions of the terms and illustration of the techniques of this application may be found in any of several well-known references such as: Sambrook, J., et al., Molecular Cloning:

A Laboratory Manual, Cold Spring Harbor Laboratory Press (1989); Goeddel, D., ed., Gene Expression Technology, Methods in Enzymology, 185, Academic Press, San Diego, Calif. (1991); "Guide to Protein Purification" in Deutshcer, M. P., ed., Methods in Enzymology, Academic Press, San Diego, Calif. (1989); Innis, et al., PCR Protocols: A Guide to Methods and Applications, Academic Press, San Diego, Calif. (1990); Freshney, R. I., Culture of Animal Cells: A Manual of Basic Technique, 2nd Ed., Alan Liss, Inc. New York, N. Y. (1987); Murray, E. J., ed., Gene Transfer and Expression Protocols, pp. 109-128, The Humana Press Inc., Clifton, N.J. and Lewin, B., Genes VI, Oxford University Press, New York (1997).

As used herein, the singular form "a", "an", and "the" include plural references unless indicated otherwise. For example, "a" modulator peptide includes one of more modulator peptides.

As used herein a compound has "activity to decrease parathyroid hormone level" or "PTH-lowering activity" when the compound, upon administration to a subject, lowers plasma parathyroid hormone (PTH) relative to the plasma PTH concentration prior to administration of the compound. In one embodiment, the decrease in PTH level is at least 20%, 30%, 40%, 50%, 60%, 70%, 80%, 90% or 95% lower one hour after compound administration that the PTH level prior to administration of the compound.

As used herein, "absence of a histamine response" or "lack of a histamine response" intends a dose of a compound that produces a less than 15-fold, 14-fold, 13-fold, 12-fold, 11-fold, 10-fold, 9-fold, 8-fold, 7-fold, 6-fold, 5-fold, 4-fold, or 3-fold increase in histamine, measured in vitro in an assay as described herein, where the fold change is determined based on histamine levels before incubation with the compound and after 15 minutes incubation with compound.

As used herein, "amino acid" refers to natural and non-natural amino acids. The twenty naturally occurring amino acids (L-isomers) are designated by the three letter code with the prefix "L-" (except for glycine which is achiral) or by the one letter code in upper-case: alanine ("L-Ala" or "A"), arginine ("L-Arg" or "R"), asparagine ("L-Asn" or "N"), aspartic acid ("L-Asp" or "D"), cysteine ("L-Cys" or "C"), glutamine ("L-Gln" or "Q"), glutamic acid ("L-Glu" or "E"), glycine ("Gly" or "G"), histidine ("L-His" or "H"), isoleucine ("L-Ile" or "I"), leucine ("L-Leu" or "L"), lysine ("L-Lys" or "K"), methionine ("L-Met" or "M"), phenylalanine ("L-Phe" or "F"), proline ("L-Pro" or "P"), serine ("L-Ser" or "S"), threonine ("L-Thr" or "T"), tryptophan ("L-Trp" or "W"), tyrosine ("L-Tyr" or "Y") and valine ("L-Val" or "V"). L-norleucine and L-norvaline may be represented as (NLeu) and (NVal), respectively. The nineteen naturally occurring amino acids that are chiral have a corresponding D-isomer which is designated by the three letter code with the prefix "D-" or by the lower-case one letter code: alanine ("D-Ala" or "a"), arginine ("D-Arg" or "r"), asparagine ("D-Asn" or "a"), aspartic acid ("D-Asp" or "d"), cysteine ("D-Cys" or "c"), glutamine ("D-Gln" or "q"), glutamic acid ("D-Glu" or "e"), histidine ("D-His" or "h"), isoleucine ("D-Ile" or "i"), leucine ("D-Leu" or "l"), lysine ("D-Lys" or "k"), methionine ("D-Met" or "m"), phenylalanine ("D-Phe" or "f"), proline ("D-Pro" or "p"), serine ("D-Ser" or "s"), threonine ("D-Thr" or "t"), tryptophan ("D-Trp" or "w"), tyrosine ("D-Tyr" or "y") and valine ("D-Val" or "v"). D-norleucine and D-norvaline may be represented as (dNLeu) and (dNVal), respectively. Although "amino acid residue" is often used in reference to a monomeric subunit of a peptide, polypeptide or protein, and "amino acid" is often used in reference to a free molecule, usage of these terms in the art overlaps and varies. The term "amino acid" and "amino acid residue" are used interchangeably and may refer to a free molecule or a monomeric subunit of a peptide, polypeptide or protein, depending on context.

To determine the percent "homology" or percent "identity" of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. As used herein amino acid or nucleic acid "homology" is equivalent to amino acid or nucleic acid "identity". Accordingly, the percent sequence identity between the two sequences is a function of the number of identical positions shared by the sequences (i.e., percent sequence identity=numbers of identical positions/total numbers of positions ×100). Percent sequence identity between two polypeptide sequences can be determined using the Vector NTI software package (Invitrogen Corporation, 5791 Van Allen Way, Carlsbad, Calif. 92008). A gap opening penalty of 10 and a gap extension penalty of 0.1 are used for determining the percent identity of two polypeptides. All other parameters are set at the default settings.

A "cationic amino acid" intends an amino acid residue that has a net positive charge at physiologic pH (7.4), as is the case, for example, in the amino acid residues where the side chain, or "R group", contains an amine functional group or other functional group that can accept a proton to become positively charged at physiologic pH, such as a guanidine or imidazole moiety. Cationic amino acid residues include arginine, lysine, histidine, 2,3-diaminopropionic acid (Dap), 2,4-diaminobutyric acid (Dab), ornithine, and homoarginine.

A "cationic subunit" intends a subunit that has a net positive charge at physiologic pH (7.4).

As used herein, "conservative amino acid substitutions" are substitutions which do not result in a significant change in the activity or tertiary structure of a selected polypeptide or protein. Such substitutions typically involve replacing a selected amino acid residue with a different amino acid residue having similar physico-chemical properties. Groupings of amino acids and amino acid residues by physico-chemical properties are known to those of skill in the art. For example, among the naturally-occurring amino acids, families of amino acid residues having similar side chains have been defined in the art, and include basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "chemical cross-linking" refers to covalent bonding of two or more molecules.

A peptide or peptide fragment is "derived from" a parent peptide or polypeptide if it has an amino acid sequence that is identical or homologous to at least a contiguous sequence of five amino acid residues, more preferably eight amino acid residues, of the parent peptide or polypeptide.

As used herein, the term "hyperparathyroidism" refers to primary, secondary and tertiary hyperparathyroidism, unless otherwise indicated.

The term "intradermal" intends that in the methods of treatment described herein a therapeutically effective amount of a calcimimetic compound is applied to skin to deliver the compound to layers of skin beneath the stratum corneum, and thus achieve a desired therapeutic effect.

As used herein, an "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of polypeptides in which the polypeptide is separated from some of the cellular components of the cells in which it is naturally or recombinantly produced. When the polypeptide or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of polypeptides in which the polypeptide is separated from chemical precursors or other chemicals that are involved in the synthesis of the polypeptide. In one embodiment, the language "substantially free of chemical precursors or other chemicals" includes preparations of a polypeptide having less than about 30% (by dry weight) of chemical precursors or other chemicals, preferably less than about 20% chemical precursors or other chemicals, more preferably less than about 15% chemical precursors or other chemicals, still more preferably less than about 10% chemical precursors or other chemicals, and most preferably less than about 5% chemical precursors or other chemicals. In preferred embodiments, isolated polypeptides, or biologically active portions thereof, lack contaminating polypeptides from the same organism from which the domain polypeptide is derived.

As used herein, "macromolecule" refers to a molecule, such as a peptide, polypeptide, protein or nucleic acid, that typically has a molecular weight greater than about 900 Daltons.

A "non-cationic amino acid" intends an amino acid residue that has no charge or a net negative charge at physiologic pH (7.4), as is the case, for example, in the amino acid residues where the side chain, or "R group", is neutral (neutral polar and neutral non-polar) and acidic. Non-cationic amino acids include those residues with an R group that is a hydrocarbon alkyl or aromatic moiety (e.g., valine, alanine, leucine, isoleucine, phenylalanine); a neutral, polar R group (asparagine, cysteine, glutamine, serine, threonine, tryptophan, tyrosine); or a neutral, non-polar R group (glycine, methionine, proline, valine, isoleucine). Non-cationic amino acids with an acidic R group include asparatic acid and glutamic acid.

A "polymer" refers to a linear chain of two or more identical or non-identical subunits joined by covalent bonds.

As used herein, "peptide" and "polypeptide" refer to any polymer made up of a chain of amino acid residues linked by peptide bonds, regardless of its size. Although "protein" is often used in reference to relatively large polypeptides, and "peptide" is often used in reference to small polypeptides, usage of these terms in the art overlaps and varies. Thus, for simplicity, the term "peptide" will be used herein, although in some cases the art may refer to the same polymer as a "polypeptide." Unless otherwise indicated, the sequence for a peptide is given in the order from the amino terminus to the carboxyl terminus.

A "thiol-containing group" or "thiol-containing moiety" as used herein intends a functional group comprising a sulfur-hydrogen bond (—SH), and that is capable of reacting with another thiol under physiologic conditions to form a disulfide bond. A thiol that is capable of forming a disulfide bond with another thiol is referred to herein as a "reactive thiol." In a preferred embodiment the thiol-containing group is less than 6 atoms away from the backbone of the compound. In a more preferred embodiment, the thiol-containing group has the structure (—SH—$CH_2$—$CH_2$—C(O)—O—)—.

As used herein, "small molecule" refers to a molecule other than a macromolecule, such as an organic molecule, and typically has a molecular weight of less than 1000 daltons.

As used herein, "subject" refers to a human subject or an animal subject.

A "subunit" intends a monomeric unit that is joined to more than one other monomeric unit to form a polymeric compound, where a subunit is the shortest repeating pattern of elements in the polymeric compound. Exemplary subunits are amino acids, which when linked form a polymer compound such as those referred to in the art as a peptide, a polypeptide or a protein.

As used herein, a "therapeutically effective amount" is an amount required to produce a desired therapeutic effect. For example, in methods for reducing serum calcium in hypercalcemic subjects, a therapeutically effective amount is the amount required to reduce serum calcium levels by at least 1%, 2%, 3%, 4%, 5%, 6%, 7%, 8%, 9%, 10%, 11%, 12%, 13%, 14%, 15%, 16%, 17%, 18%, 19%, 20% or 25%. Calcium may be measured as total calcium or as ionized calcium. By way of another example, in methods for lowering in vivo PTH, a therapeutically effective amount is the amount required to reduce PTH levels by at least 1%, 2%, 3%, 4%, 5%, 6%, 7%, 8%, 9%, 10%, 11%, 12%, 13%, 14%, 15%, 16%, 17%, 18%, 19%, 20% or 25%.

As used herein, the term "transdermal" means that in the methods of treatment described herein a therapeutically effective amount of a calcimimetic agent is applied to skin to deliver the compound to systemic circulation and thus achieve a desired therapeutic effect.

Unless otherwise specified, all documents referred to herein are incorporated by reference in their entirety.

II. Compounds

In one aspect, a compound comprising the sequence of subunits $X_1$-$X_2$-$X_3$-$X_4$-$X_5$-$X_6$-$X_7$ is provided, where $X_1$ is a subunit comprising a thiol group; $X_5$ is a cationic subunit; $X_6$ is a non-cationic subunit; $X_7$ is a cationic a subunit; and at least two of $X_2$, $X_3$ and $X_4$ are independently a cationic subunit. The compounds have activity to decrease parathyroid hormone (PTH) levels and/or decrease calcium levels in a subject's blood. A decrease in parathyroid hormone levels, as will be illustrated below, intends a lowering of plasma or blood PTH concentration in a subject relative to the plasma or blood PTH concentration prior to treatment with the compound. In one embodiment, the compound achieves a reduction in plasma PTH concentration by at least 50% within one hour after dosing, relative to the plasma PTH prior to dosing. The compounds are exemplified by peptides, although a skilled artisan will appreciate that non-peptidic compounds that have the desired activity can be designed based on the structure-activity relationship studies described herein.

As used herein parathyroid hormone or PTH is an 84 amino acid peptide produced by the parathyroid gland and its breakdown products. Besides full length PTH (which consists of residues 1-84 and is sometimes referred to as "intact" of "bioactive" PTH) various PTH fragments generated by proteolysis and other routes of metabolism are present in blood. The amino-terminal 1-34 region of the intact PTH molecule is biologically active. This region of the molecule contains the amino acid sequence that enables PTH to bind to the parathyroid hormone receptors in target tissues. The middle and carboxy-terminal 35-84 region of the intact PTH molecule is believed to be biologically inert but possesses immunological reactivity. PTH 7-84 is thought to exert effects that are opposite to those of 1-84 PTH. Various assays have been developed to measure PTH levels including various breakdown products and are reviewed by Souberbielle et. al., *Kidney International*, 77:93-100 (2010), which is incorporated herein by reference. In one embodiment, a compound having activity to decrease PTH level as defined herein is ascertained using a validated PTH quantification method that detects the intact bioactive form of PTH(1-84), and commercially available kits are known in the art (e.g., see Example 3 herein).

In a first study, compounds containing 4 to 7 cationic (e.g., arginine) subunits were generated and tested for their ability to lower PTH as compared with baseline PTH values and saline-treated animals. Specifically, a 1K1C model of acute renal insufficiency was established for use in characterizing the PTH-lowering activity in a renal dysfunction environment. The 1K1C model is described in Example 1A, and the compounds synthesized for testing included (i) Ac-crrrr-NH$_2$ (SEQ ID NO:4), (ii) Ac-crrrrr-NH$_2$ (SEQ ID NO:5), (iii) Ac-crrrrrr-NH$_2$ (SEQ ID NO:6), (iv) Ac-crrrrrrr-NH$_2$ (SEQ ID NO:7) and (v) saline control.

As described in Example 1B, the compounds identified as SEQ ID NO:4, SEQ ID NO:5, SEQ ID NO:6 and SEQ ID NO:7 were each administered by a 30-minute IV infusion to 1K1C model animals. FIG. 1 shows the reduction in plasma PTH levels as a percent of the pre-dosing (baseline) level. All four compounds dosed at 3 mg/kg produced a significant drop in plasma PTH, but differences in the potency and duration of PTH reduction suggest a relationship between the net positive charge and PTH-lowering activity. For example, the compound Ac-crrrrrr-NH$_2$ (SEQ ID NO:6; triangles) with six cationic (arginine) subunits had increased efficacy as well as the duration of action compared to the compounds Ac-crrrr-NH$_2$ (SEQ ID NO:4; diamonds) and Ac-crrrrr-NH$_2$ (SEQ ID NO:5; squares), containing four and five cationic (arginine) subunits, respectively. Surprisingly, the compound Ac-crrrrrr-NH$_2$ (SEQ ID NO:6; triangles) with six cationic (arginine) subunits had increased duration of action compared to the compound Ac-crrrrrrr-NH$_2$ (SEQ ID NO:7, open squares) with seven cationic (arginine) residues, suggesting that activity or potency of the compounds does not correlate merely with increasing cationic charge of the compound. That is, the compound Ac-crrrrrrr-NH$_2$ (SEQ ID NO:7) with seven cationic subunits (arginine residues) produced a similar initial drop in PTH as the compounds with fewer cationic residues, but over the 24 hours following dosing was less efficacious than Ac-crrrrrr-NH$_2$ (SEQ ID NO:6) and Ac-crrrrr-NH$_2$ (SEQ ID NO:5). These latter two compounds produced a mean PTH reduction of ~40% and 60% at the 24 hour time point, respectively. Both the extent of PTH reduction and duration of PTH are important criteria for obtaining optimal therapeutic benefit for patients in need of treatment. It should be noted that the compounds in this study were administered at the same mg/kg dose but, due to differences in molecular weight, a different number of moles of each compound was actually dosed. Therefore, Ac-crrrrrr-NH$_2$ (SEQ ID NO:6) was significantly more potent than Ac-crrrr-NH$_2$ (SEQ ID NO:4) and Ac-crrrrr-NH$_2$ (SEQ ID NO:5) on a per mole basis.

Further studies were done to explore the structure-activity relationship of the compounds. The compound Ac-crrrrrr-NH$_2$ (SEQ ID NO:6) was modified by sequential replacement of an arginine residue with an alanine residue at each of the subunit positions $X_2$-$X_7$. The compounds were characterized in an in vitro human calcium-sensing receptor (CaSR) assay, described in Example 2, wherein HEK 293 cells that express the human calcium-sensing receptor were used to measure activity of exemplary compounds. Without wishing to be bound by theory, it is thought that the mechanism by which the described compounds lower PTH in vivo is through the activation of the CaSR, which is expressed in the parathyroid gland and controls PTH secretion. Activation of the CaSR leads to an increase in intracellular calcium and inositol-3-phosphate (IP3) and the subsequent accumulation of inositol-phosphate-1 (IP$_1$). Accordingly, in this in vitro assay, the half maximal effective concentration of compound to reduce IP$_1$ generation by 50% was determined (EC$_{50}$). The same compounds were also tested in vivo to determine their PTH-lowering activity, as described in Example 3. Results are shown in Table 1. The numbers in the column titled "% PTH AUC (1-4 hrs) of saline control" of Table 1 define activity as reduction in Area Under the Curve (AUC) of PTH over 4 hours as a percent of PTH AUC derived from saline-treated control rats. For example, an AUC (compound treated)/AUC (saline control)*100 that is equal to 0 would be indicative of a highly active PTH-lowering compound that completely suppresses PTH (to an undetectable level) for 4 hours after a single IV administration of isoflurane (IF)-anesthetized normal rats. In contrast, a value of AUC (compound treated)/AUC (saline control)*100 that is equal to or greater than 100 would be indicative of an inactive compound.

TABLE 1

In vitro and In vivo activity of Exemplary Compounds

| | | In vivo activity in normal rats** | | |
|---|---|---|---|---|
| SEQ ID NO. | Structure* | % PTH reduction of baseline at 1 hour post IV admin. of 0.5 mg/kg compound | 0.5 mg/kg IV bolus % PTH AUC of saline control | In vitro EC$_{50}$ (uM) |
| SEQ ID NO: 6 | Ac-crrrrrr-NH$_2$ | 4 | 0 | 0.5 |
| SEQ ID NO: 8 | Ac-carrrrr-NH$_2$ | 0 | 0 | 1.1 |
| SEQ ID NO: 9 | Ac-crarrrr-NH$_2$ | 0 | 7 | 1.0 |
| SEQ ID NO: 10 | Ac-crrarrr-NH$_2$ | 0 | 0 | 1.1 |
| SEQ ID NO: 11 | Ac-crrrarr-NH$_2$ | 9 | 45 | 5.9 |
| SEQ ID NO: 12 | Ac-crrrrar-NH$_2$ | 3 | 3 | 0.45 |

TABLE 1-continued

In vitro and In vivo activity of Exemplary Compounds

| | | In vivo activity in normal rats** | | |
| | | % PTH reduction of baseline at 1 hour post IV admin. of 0.5 mg/kg compound | 0.5 mg/kg IV bolus % PTH AUC of saline control | In vitro EC$_{50}$ (uM) |
| SEQ ID NO. | Structure* | | | |
| --- | --- | --- | --- | --- |
| SEQ ID NO: 13 | Ac-crrrrra-NH$_2$ | 4 | 28 | 1.1 |
| | Saline | 128 | 100 | ND |

*Bolded fond indicates D-alanine substitutions of cationic amino acids (D-arginine in SEQ ID NO: 6).
**PTH reduction following 0.5 mg/kg IV administration in isofluorane-anesthetized normal rats-PTH was measured at 1, 2, 3 and 4 hours post administration and cumulative AUC was calculated. PTH data were calculated according to the following formula: AUC$_{cmpd\ treated}$/AUC$_{saline\ control}$*100.

In Table 1, the compounds Ac-crrrrrr-NH$_2$ (SEQ ID NO:6), Ac-carrrrr-NH$_2$ (SEQ ID NO:8) and Ac-crrarrr-NH$_2$ (SEQ ID NO:10) were quite potent, as evidenced by the decrease in percent PTH to below the detection limit or essentially zero as measured in vivo after a single IV administration in normal rats. Substitution of the cationic (arginine) residue at positions 2, 3, 4 or 7 of Ac-crrrrrr-NH$_2$ (SEQ ID NO:6) resulted in an approximately two-fold loss in in vitro potency. The substitution at position 5 to produce the compound Ac-crrrarr-NH$_2$ (SEQ ID NO:11) produced a 5-10 fold reduction in in vitro potency, although the in vivo percent PTH AUC reduction of 45% could be sufficiently active for clinical therapy. Surprisingly, the substitution of the cationic arginine residue at position 6 with the uncharged (alanine) residue actually improved potency. The data illustrate that cationic and uncharged residues at different positions are not all equal and there are changes in activity as a result of change in the compound structure.

To further evaluate the effect of change in activity as a function of change in compound structure, another series of analogs of Ac-crrrrrr-NH$_2$ (SEQ ID NO:6) was generated containing double amino acid substitutions, where two cationic (arginine) residues were replaced by uncharged (alanine) residues, and tested for potency. Data are shown in Table 2. It is worth noting that this series of compounds have the same net cationic charge as SEQ ID NO:4 (four cationic residues) yet surprisingly some are very active (SEQ ID NO:26) with very low % PTH AUC of saline control while others are inactive (e.g., SEQ ID NO:14). Unexpectedly, this suggests that position of charges as well as total cationic charge can influence potency of the compounds for reduction of PTH. The data shown in Table 2 is consistent with the data shown in Table 1 suggesting that the cationic residues of SEQ ID NO:6 are essential at positions 5 and 7 but is not required at position 6, for PTH-lowering activity.

TABLE 2

In vivo Activity of Exemplary Compounds

| | | In vivo activity in normal rats** | |
| | | % PTH reduction of baseline at 1 hour Post IV administration of 0.5 mg/kg compound | 0.5 mg/kg IV bolus % PTH AUC of saline control* |
| SEQ ID NO. | Compound Structure* | | |
| --- | --- | --- | --- |
| Saline | Saline | 128 | 100 |
| SEQ ID NO: 14 | Ac-crrarra-NH$_2$ | 86 | 130 |
| SEQ ID NO: 15 | Ac-cararrr-NH$_2$ | 75 | 116 |
| SEQ ID NO: 16 | Ac-carrarr-NH$_2$ | 118 | 105 |
| SEQ ID NO: 17 | Ac-crraarr-NH$_2$ | 39 | 102 |
| SEQ ID NO: 18 | Ac-crararr-NH$_2$ | 72 | 87 |
| SEQ ID NO: 19 | Ac-carrrra-NH$_2$ | 29 | 72 |
| SEQ ID NO: 20 | Ac-crarrra-NH$_2$ | 45 | 69 |
| SEQ ID NO: 21 | Ac-crrraar-NH$_2$ | 36 | 50 |
| SEQ ID NO: 22 | Ac-caarrrr-NH$_2$ | 24 | 48 |
| SEQ ID NO: 23 | Ac-crarrar-NH$_2$ | 0 | 43 |
| SEQ ID NO: 24 | Ac-craarrr-NH$_2$ | 8 | 9 |
| SEQ ID NO: 25 | Ac-crrarar-NH$_2$ | 4 | 6 |
| SEQ ID NO: 26 | Ac-carrrar-NH$_2$ | 0 | 1 |
| SEQ ID NO: 27 | Ac-c(C)arrrar-NH$_2$ | 2 | 8 |
| SEQ ID NO: 28 | Ac-c(C)rrarar-NH$_2$ | 0 | 16 |

*Bolded font indicates respsective D-alanine substitutions of cationic amino acids (D-arginine) in Ac-crrrrrr-NH$_2$ (SEQ ID NO: 6)
**PTH reduction following 0.5 mg/kg IV administration in isofluorine-anesthetized normal rats-PTH was measured at 1, 2, 3 and 4 hours post administration and cumulative AUC was calculated. PTH data were calculated according to the following formula: AUC$_{cmpd\ treated}$/AUC$_{saline\ control}$*100.

The data in Table 2 illustrates the structural changes that influence activity. In one embodiment, the compound is Ac-caarrrr-NH$_2$ (SEQ ID NO:22) and in another embodiment, the compound is Ac-craarrr-NH$_2$ (SEQ ID NO:24).

Figure 2A:
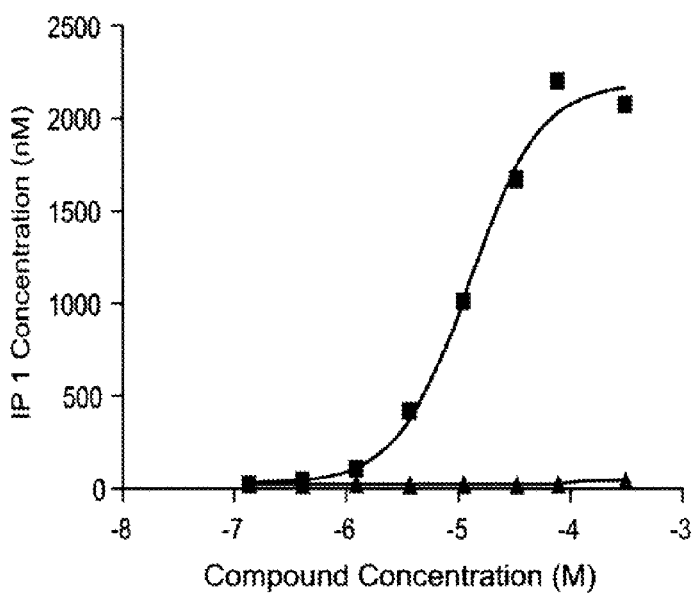
FIG. 2A is a graph of IP$_1$ concentration, in nM, as a function of compound concentration of Ac-carrrar-NH$_2$ (SEQ ID NO:26, squares) and Ac-arrrar-NH$_2$ (SEQ ID NO:29, triangles), as a measure of the compound's ability to activate the human CaSR in an in vitro cell assay when the human CaSR is expressed as a stable transfected HEK-293 cell line.

Further structure-activity relationship studies were conducted using the in vitro cell assay in HEK 293 cells that express the human calcium-sensing receptor, as described in Example 4. The ability of the peptides Ac-carrrar-NH$_2$ (SEQ ID NO:26) and Ac-arrrar-NH$_2$ (SEQ ID NO:29) to activate the human CaSR was ascertained by the measuring accumulation of inositol monophosphate (IP$_1$), which is reflective of IP$_3$ production. IP$_3$ production is an important cell signaling second messenger and its production is a direct downstream consequence of CaSR activation. Accumulation of IP$_1$ following IP$_3$ production can be obtained by treating the cells used in the assay with Lithium Chloride (LiCl$_2$) which inhibits the enzyme that converts IP$_1$ to inositol. In the studies described in Example 4 accumulation of IP$_1$ was measured in the presence of the exemplary compounds Ac-carrrar-NH$_2$ (SEQ ID NO:26) and Ac-arrrar-NH$_2$ (SEQ ID NO:29). Results are shown in FIG. 2A.

The concentration of IP$_1$ is reported as nM along the Y-axis and compound concentrations of SEQ ID NO:26 or SEQ ID NO:29 are reported as M along the X-axis. Absence of the N-terminal D-cysteine residue from SEQ ID NO:29 dramatically reduced the ability of the compound to activate the CaSR as compared to SEQ ID NO:26. That is, elimination of the N-terminal cysteine residue significantly reduced the potency of the compound, as the peptides Ac-carrrar-NH (SEQ ID NO:26) and Ac-arrrar-NH$_2$ (SEQ ID NO:29) differ only by the presence or absence of the N-terminal D-cysteine.

The contribution of the thiol-containing group in the X$_1$ subunit of the compound (e.g., in certain embodiments where the compound is a peptide on the N-terminal residue), was also investigated in an in vivo study. The PTH-lowering activity of the peptides identified as SEQ ID NO:26 (Ac-carrrar-NH$_2$) and as SEQ ID NO:29 (Ac-arrrar-NH$_2$) was evaluated in vivo according to the procedures in Example 4. Plasma PTH levels were assessed prior to dosing and at 1, 2, 3 and 4 hours after dosing. The results are shown in FIG.

2B. As seen, a 0.5 mg/kg dose of the peptide Ac-carrrar-NH$_2$(SEQ ID NO:26) (squares) decreased PTH blood concentration to a non-detectable level for up to 4 hours after dosing. In contrast, the peptide lacking an N-terminal residue with a thiol-containing group, Ac-arrrar-NH$_2$ (SEQ ID NO:29), diamonds, did not reduce PTH concentration, even at a substantially higher dose (i.e., 9 mg/kg).

The structure-activity relationship of the thiol-containing group in the $X_1$ subunit of the compound was further analyzed by preparing compounds with differing $X_1$ subunits. The compounds, shown in Table 3, were tested in vivo in normal rats for activity to reduce PTH.

TABLE 3

In vivo Activity of Exemplary Compounds

| SEQ ID NO. | Compound Structure | In vivo activity in normal rats* 0.5 mg/kg IV bolus % PTH AUC of saline control** |
|---|---|---|
| Saline | Saline | 100 |
| SEQ ID NO: 6 | Ac-crrrrrr-NH$_2$ | 3 |
| SEQ ID NO: 30 | Ac-bAla-crrrrrr-NH$_2$ | 0 |
| SEQ ID NO: 31 | Mpa-rrrrrr-NH$_2$ | 2 |
| SEQ ID NO: 32 | Ac-dHcy-rrrrrr-NH$_2$ | 21 |
| SEQ ID NO: 33 | Ac-dPen-rrrrrr-NH$_2$ | 9 |

*Bolded font indicates respective substitution of thiol-containing residue (D-cysteine) in Ac-crrrrrr-NH$_2$ (SEQ ID NO: 6).
**PTH reduction following 0.5 mg/kg IV administration in isoflurane-anesthetized normal rats-PTH was measured at 1, 2, 3 and 4 hours post administration and cumulative AUC was calculated. PTH data were calculated according to the following formula: AUC$_{cmpd\ treated}$/AUC$_{saline\ control}$*100.

The data in Table 3 illustrates that the thiol-containing $X_1$ subunit can be varied. Compounds with the following in the N-terminal residue were tested—D-cysteine (cys), D-penicillamine (dPen), d-homocysteine (dHcy) and mercaptopropionic acid (Mpa). In addition, a natural or non-natural amino acid, such as beta alanine, can be conjugated to the N-terminal thiol-containing residue. The data illustrates that cationic compounds such as Ac-crrrrrr-NH$_2$ (SEQ ID NO:6) containing different thiol-containing groups in the $X_1$ subunit effectively reduce PTH in vivo. Substituting the N-terminal cysteine residue with methionine, which does not contain a thiol group, resulted in a compound with very poor in vivo PTH-lowering activity (data not shown).

Based on the studies above, compounds of the contiguous sequence of subunits $X_1$-$X_2$-$X_3$-$X_4$-$X_5$-$X_6$-$X_7$, where $X_1$ is a subunit comprising a thiol-containing group, have activity to decrease parathyroid hormone levels. In one embodiment, the thiol-containing group on the $X_1$ subunit is selected from the group consisting of thiol-containing amino acid residues and organic thiol-containing moieties. In another embodiment, the thiol-containing group is capable of reacting with another thiol group under physiologic pH and temperature. In certain embodiments where the thiol-containing residue is an amino acid residue, the $X_1$ subunit can be any one of cysteine, glutathione, mercapto-propionic acid, n-acetylated cysteine and PEGylated cysteine. In embodiments where the thiol-containing group is on a non-amino acid residue subunit, such an organic small molecule with a thiol-containing group, the $X_1$ subunit can be a thiol-alkyl, or thioacyl moieties such as 3-mercaptopropyl or 3-mercaptopropionyl residues. In one embodiment, the thiol is not homocysteine.

Accordingly, and in another embodiment, the compounds described herein have "clinical activity to decrease parathyroid hormone level", which intends that the compound, upon administration to a subject, lowers plasma parathyroid hormone as measured by the cumulative PTH area under the curve (PTH AUC) over 4 hours post administration compared to PTH AUC of a corresponding vehicle treated control subject. The plasma PTH concentrations are measured using, for example, a commercially available ELISA kit that detects bioactive intact PTH 1-84 (see Example 3 for a specific kit). compound with clinical activity to decrease parathyroid hormone level reduces the PTH AUC by at least 20%, 30%, 40%, 50%, 60%, 70%, 80%, 90%, 95% compared to the PTH AUC of a corresponding vehicle treated control subject.

The studies above, and others described below, illustrate further embodiments of the compounds described herein, wherein the $X_1$ subunit in some embodiments can be modified chemically, such as by chemical modification to include an acetyl group, a benzoyl group, a benzyl group, a butyl group, a natural or unnatural amino acid such as acetylated-beta-alanine or is joined by a covalent linkage to another thiol moiety. Peptide therapeutics may be vulnerable to attack by peptidases. Exopeptidases are typically non-specific enzymes which cleave amino acid residues from the amino or carboxy termini of a peptide or protein. Endopeptidases, which cleave within an amino acid sequence, can also be non-specific; however endopeptidases frequently recognize particular amino sequences (recognition sites) and cleave the peptide at or near those sites. Accordingly, modifications to the compound to protect it from proteolytic degradation are contemplated.

One method of protecting a peptide from proteolytic degradation involves chemically modifying, or "capping," the amino and/or carboxy termini of the peptides. As used herein, the terms "chemically modified" or "capped" are used interchangeably to refer to the introduction of a blocking group to a terminus or to both termini of the compound via a covalent modification. Suitable blocking groups serve to cap the termini of the peptides without decreasing the biological activity of the peptides. Any residue positioned at the amino or carboxy termini, or both, of the described compounds, including the thiol-containing subunits can be chemically modified.

In a preferred embodiment, the amino terminus of the compound is chemically modified by acetylation, to provide an N-acetyl peptide (which may be represented as "Ac-" in a structure or formula herein). In a preferred embodiment, the carboxy terminus of the described peptides, is chemically modified by amidation to provide a primary carboxamide at the C-terminus (which may be represented as "—NH$_2$" in a peptide sequence, structure or formula herein). In a preferred embodiment, both the amino terminus and carboxy terminus are chemically modified by acetylation and amidation, respectively. However, other capping groups are possible. For example, the amino terminus may be capped by acylation with groups such as an acetyl group, a benzoyl group, or with natural or unnatural amino acids such as beta-alanine capped with an acetyl group, or by alkylation with groups such as a benzyl group or a butyl group, or by sulfonylation to form sulfonamides. Similarly, the carboxy terminus may be esterified, or converted to a secondary amide, and acyl sulfonamide, or the like. In some embodiments, the amino terminus or the carboxy terminus may comprise a site for attachment of a polyethylene glycol (PEG) moiety, i.e., the amino or carboxy termini may be chemically modified by reaction with a suitably functionalized PEG.

Protecting peptides from endopeptidases typically involves identification and elimination of an endopeptidase recognition site from a peptide. Protease recognition sites are well known to those of ordinary skill in the art. Thus it is possible to identify a potential endoprotease recognition site and then eliminating that site by altering the amino acid sequence within the recognition site. Residues in the recognition sequence can be moved or removed to destroy the recognition site. Preferably, a conservative substitution is made with one or more of the amino acids which comprise an identified protease recognition site.

A. Additional Structure-Activity Relationship Studies

Additional structure activity studies were conducted, to further evaluate the effect of properties of each subunit in the compound on its therapeutic activity. These studies are now to be described with reference to Example 5.

A series of compounds having an L-amino acid residue substituted for a D-amino acid residue were prepared based on the PTH-lowering scaffold Ac-c(C)arrrar-NH$_2$ (SEQ ID NO:3). The compounds were administered to subjects and plasma PTH levels were assessed prior to dosing and 1, 2, 3 and 4 hours after dosing, as described in Example 5 and the AUC was calculated as the sum of the PTH concentration values at the time points of 1, 2, 3 and 4 hours, normalized by the AUC for the saline control at the same time points, multiplied by 100. The results are shown in Table 4.

TABLE 4

Effect of L-Amino Acid Substitution on Potency

| Compound Name | Structure | In vivo activity in normal rats 0.5 mg/kg IV bolus % PTH AUC* of saline control |
| --- | --- | --- |
| SEQ ID NO: 3 | Ac-c(C)arrrar-NH$_2$ | 8 |
| SEQ ID NO: 34 | Ac-C(C)arrrar-NH$_2$ | 17 |
| SEQ ID NO: 35 | Ac-c(C)Arrrar-NH$_2$ | 68 |
| SEQ ID NO: 36 | Ac-c(C)aRrrar-NH$_2$ | 87 |
| SEQ ID NO: 37 | Ac-c(C)arRrar-NH$_2$ | 182 |
| SEQ ID NO: 38 | Ac-c(C)arrRar-NH$_2$ | 130 |
| SEQ ID NO: 39 | Ac-c(C)arrrAr-NH$_2$ | 129 |
| SEQ ID NO: 40 | Ac-c(C)arrraR-NH$_2$ | 142 |
| | Saline | 100 |

*PTH reduction following 0.5 mg/kg IV administration in isoflurane-anesthetized normal rats-PTH was measured at 1, 2, 3 and 4 hours post administration and cumulative AUC was calculated. PTH data were calculated according to the following formula: AUC$_{cmpd\ treated}$/AUC$_{saline\ control}$*100

The exemplary compounds shown in Table 4 were chemically modified at both the N-terminus and the C-terminus, as indicated by the Ac and NH$_2$ designations. The sequence of seven subunits carrrar (SEQ ID NO:3), wherein all subunits were D-amino acid residues, was modified by replacing one subunit at a time with an L-amino acid. The X$_1$ subunit was a D-Cys residue (or L-Cys residue in SEQ ID NO:34) conjugated via a disulfide linkage to an L-Cys residue, as indicated by the parenthetical designation (C). The PTH-lowering in vivo data in Table 4 shows that chirality of Arg and Ala affect activity of the compounds. In one embodiment, a compound of the sequence X$_1$-X$_2$-X$_3$-X$_4$-X$_5$-X$_6$-X$_7$ is contemplated, where at least the subunits identified as X$_4$ and X$_7$ are D-amino acid residue subunits. In another embodiment, the subunits identified as X$_4$, X$_5$, X$_6$ and X$_7$ are D-amino acid residue subunits. In a preferred embodiment, the subunits identified as X$_3$, X$_4$, X$_5$, X$_6$ and X$_7$ are D-amino acid residue subunits. In most preferred embodiments, the subunits identified as X$_2$, X$_3$, X$_4$, X$_5$, X$_6$ and X$_7$ are D-amino acid residue subunits, and all of the subunits X$_1$, X$_2$, X$_3$, X$_4$, X$_5$, X$_6$ and X$_7$ are D-amino acid residue subunits.

In other studies, it also was found that substitution of a peptide having all L-amino acids with all D-amino acids did not reduce the in vitro activity of the peptides tested; in fact, peptides composed entirely of D-amino acids appeared to enhance the potency for activation of the CaSR. It was also shown that some of the cationic (arginine) residues, at specific positions relative to the cysteine residue, could be substituted with uncharged (alanine) residues with minimal effect on the activity toward the CaSR.

To further characterize the relationship between structure and activity against the CaSR, a variety of cationic peptides with different numbers (4 to 8) of arginine residues (all of which contained an N-terminal cysteine) were tested using the HEK-293 in vitro cell assay. A direct correlation was found between the number of cationic subunits and the potency of the compound, where potency is evidenced by ability to activate the CaSR. Reducing the number of cationic (e.g., arginine) subunits from 5 to 4 resulted in the largest shift in potency (>10-fold) suggesting that there may be an activity inflection point between compounds having these net charges, that a cationic subunit at subunit X$_5$ is preferred for activity. Accordingly, the compounds of the structure X$_1$-X$_2$-X$_3$-X$_4$-X$_5$-X$_6$-X$_7$ are contemplated, wherein X$_5$ is a cationic subunit. In certain embodiments the X$_1$ is a subunit comprises a thiol group that is capable of reacting with another thiol group under physiologic conditions (a "reactive thiol", intending a thiol that reacts with another thiol (e.g., cysteine with cysteine) under physiologic conditions of pH 7.4 and body temperature).

Unexpectedly, Ac-crrrrrr-NH$_2$ (SEQ ID NO:6) with six cationic residues, when evaluated in vivo, exhibited greater and more prolonged activity than Ac-crrrrrrrr-NH$_2$ (SEQ ID NO:41), which has eight cationic residues. This is in contrast to the observation that SEQ ID NO:41 was more potent at activating the CaSR in this in vitro cell assay. Without wishing to be bound by theory, it is thought that the superior performance of Ac-crrrrrr-NH$_2$ (SEQ ID NO:6) in vivo may stem from better pharmacokinetic properties of Ac-crrrrrr-NH$_2$ (SEQ ID NO:6), because Ac-crrrrrrrr-NH$_2$ (SEQ ID NO:6441 is expected to be taken up into cells by virtue of its cell-penetrating characteristic, and thus removed from proximity to the active portion of the CaSR.

To further explore the structure-activity relationship of Ac-crrrrrr-NH$_2$ (SEQ ID NO:6), some of the cationic (arginine) residues were replaced with uncharged (alanine) residues. It was found that replacing the cationic (arginine) residues at subunit positions X$_2$ and X$_4$ resulted in a compound (SEQ ID NO:15) that had significantly reduced potency in vitro in activating the CaSR. By contrast, replacing the cationic (arginine) residues at subunit positions X$_2$ and X$_6$ resulted in a compound (SEQ ID NO:26) that retained much of the potency seen with Ac-crrrrrr-NH$_2$ (SEQ ID NO:6). These results suggest that the position of charged residues in the compound contributes to potency and, in some embodiments, may outweigh the contribution of total positive charge of the peptide. It also appears that cationic (arginine) residues at certain positions, such as subunit position X$_5$, contribute disproportionately to potency.

It was found that the presence of an N-terminal cysteine markedly enhances the potency of the peptides for activating the CaSR. The CaSR is a 7-transmembrane G-protein-coupled receptor with a large extracellular domain that functions as a homodimeric receptor. There are 18 cysteine residues in the extracellular domain, some of which have been shown by polymorphism or mutational analysis to be important for receptor activity. Of particular note are cysteines 129 and 131 of the Loop 2 region of the extracellular domain. Cysteines 129 and 131 are thought to form an intermolecular disulfide bridge between the two monomers of the receptor complex, which is in a closed or inhibited configuration. Mutation of cysteine 129 activates the CaSR, as do a number of other mutations including a full deletion of the Loop2 region. The enhanced potency provided by the N-terminal cysteine residue in the described compounds could result from a specific interaction with one or more of the cysteine residues in the extracellular domain of the CaSR.

To further evaluate the effect of chirality of amino acid substitutions on in vitro CaSR activity, a series of analogs of Ac-crrrrrr-NH$_2$ (SEQ ID NO:6) were generated containing L-amino acid or achiral amino acid (glycine) substitutions at various positions and tested for potency against the CaSR. Tested analogs included Ac-cGrrrGr-NH$_2$ (SEQ ID NO:42), (ii) Ac-cArrrAr-NH$_2$ (SEQ ID NO:43), and (iii) Ac-CaR-rRaR-NH$_2$ (SEQ ID NO:44). All of the foregoing analogs had significantly lower potency than Ac-crrrrrr-NH$_2$ (SEQ ID NO:6), ranging from a 10-fold difference for SEQ ID NO:44 (the most potent of the three analogs) and a more than 2000-fold difference for SEQ ID NO:43 (the least potent of the three analogs). Ac-carrrar-NH$_2$ (SEQ ID NO:26), in which cationic D-amino acid residues (D-arginine residues) at positions 2 and 6 of SEQ ID NO:6 were replaced by uncharged D-amino acid residues (D-arginine residues), the change in activity was much less (~3 fold difference). Thus, surprisingly, it was found that interrupting the all D-amino acid residue of Ac-crrrrrr-NH$_2$ (SEQ ID NO:6) with two or more L-amino acid residues resulted in a significant reduction in potency. Also surprising was that potency was decreased more than 80-fold when the interrupting residue was an uncharged achiral amino acid residue (glycine residue) compared to when it was an uncharged L-amino acid residue (L-alanine residue).

Also surprising was that replacing the two uncharged D-amino acid residues (D-alanine residues) of Ac-carrrar-NH$_2$ (SEQ ID NO:26) with their L-counterparts (SEQ ID NO:43), resulted in a greater than 600-fold decrease in potency, while replacing them with an uncharged achiral amino acid residue (glycine residue) (SEQ ID NO:42) resulted in less than an 8-fold reduction in potency; and that replacing three cationic D-amino acid residues (D-arginine residues) of Ac-carrrar-NH$_2$ (SEQ ID NO:26) with their L-counterparts (SEQ ID NO:44), resulted in less than a 4-fold difference in potency.

The activity of a variety of peptides and conjugates was tested against the human CaSR. These studies were conducted by measuring IP$_1$ production in HEK293 cells that express the human CaSR. The EC$_{50}$ values are shown in Table 5. Each peptide was tested in eight different concentrations, in duplicates, to establish a dose response curve. Curve fitting was performed using GraphPad Prism. In Table 5, and throughout the specification, residues provided in capital letters are L-amino acids, while lower case letters indicate D-amino acids. "Ac" indicates an acetyl capping group, "NH$_2$" indicates an amide capping group, "Ac-bAla" is an acetylated beta-alanine, "GSH" indicates reduced glutathione, "GS" indicates oxidized glutathione, "PEG" refers to polyethylene glycol, "PEG2" and "PEG5" refer to polyethylene glycol moieties of 2 kDa and 5 kDa, respectively, and "Mpa" refers to mercaptopropionic acid. A group bracketed by parentheses indicates that group or moiety is attached to the side-chain of the preceding subunit or amino acid residue.

TABLE 5

EC$_{50}$ values for cationic peptides in CaSR in vitro assay

| Compound Name | Structure | EC$_{50}$ (μM) |
|---|---|---|
| (SEQ ID NO: 45) | CHDAPIGYD<br>\|<br>Ac-CYGRKKRRQRRR-NH$_2$ | 21 |
| (SEQ ID NO: 47) | | |
| (SEQ ID NO: 46) | CPDYHDAGI<br>\|<br>Ac-CYGRKKRRQRRR-NH$_2$ | 21 |
| (SEQ ID NO: 47) | | |
| (SEQ ID NO: 47) | Ac-CYGRKKRRQRRR-NH$_2$ | 4.5 |
| (SEQ ID NO: 48) | Ac-YGRKKRRQRRR-NH$_2$ | 16 |
| (SEQ ID NO: 41) | Ac-crrrrrrr-NH$_2$ | 0.3 |
| (SEQ ID NO: 6) | Ac-crrrrrr-NH$_2$ | 0.5 |
| (SEQ ID NO: 15) | Ac-cararrr-NH$_2$ | 13 |
| (SEQ ID NO: 26) | Ac-carrrar-NH$_2$ | 1.6 |
| (SEQ ID NO: 4) | Ac-crrrr-NH$_2$ | 16 |
| (SEQ ID NO: 5) | Ac-crrrrr-NH$_2$ | 2.5 |
| (SEQ ID NO: 7) | Ac-crrrrrrr-NH$_2$ | 0.6 |
| (SEQ ID NO: 49) | Ac-caraarrr-NH$_2$ | 1000 |
| (SEQ ID NO: 8) | Ac-carrrr-NH$_2$ | 1.1 |
| (SEQ ID NO: 9) | Ac-crarrr-NH$_2$ | 1 |
| (SEQ ID NO: 10) | Ac-crrarrr-NH$_2$ | 1.1 |
| (SEQ ID NO: 50) | Ac-cygrkkrrqrrr-NH$_2$ | 2 |
| (SEQ ID NO: 51) | H$_2$N-crrrrrr-NH$_2$<br>\|<br>H$_2$N-crrrrrr-NH$_2$ | 0.44 |
| (SEQ ID NO: 3) | Ac-c(C)arrrar-NH$_2$ | 10 |
| (SEQ ID NO: 52) | Ac-carrrar-NH$_2$<br>\|<br>Ac-carrrar-NH$_2$ | 0.7 |
| (SEQ ID NO: 30) | Ac-bAla-crrrrrr-NH$_2$ | 1 |
| (SEQ ID NO: 53) | Ac-c(GS)rrrrrr-NH$_2$ | 7.8 |
| (SEQ ID NO: 54) | GS-crrrrrr | — |
| (SEQ ID NO: 55) | Ac-c(Ac-C)arrrar-NH$_2$ | 21 |
| (SEQ ID NO: 56) | Ac-c(Mpa)arrrar-NH$_2$ | 21 |
| (SEQ ID NO: 57) | Ac-c(PEG2-C)arrrar-NH$_2$ | 2.3 |
| (SEQ ID NO: 58) | Ac-c(PEG5-C)rrrrrr-NH$_2$ | 0.58 |
| (SEQ ID NO: 59) | Ac-c(PEG2-C)rrrrrr-NH$_2$ | 0.02 |
| (SEQ ID NO: 34) | Ac-C(C)arrrar-NH$_2$ | 2.5 |
| (SEQ ID NO: 60) | c(C)arrrar-NH$_2$ | 3.1 |
| (SEQ ID NO: 61) | Ac-bAla-c(C)arrrar-NH$_2$ | 2.6 |
| (SEQ ID NO: 62) | bAla-c(C)arrrar | — |
| (SEQ ID NO: 42) | Ac-cGrrrGr-NH$_2$ | 12 |
| (SEQ ID NO: 63) | Ac-cGrrrGr | — |
| (SEQ ID NO: 64) | Ac-cArrrAr | — |
| (SEQ ID NO: 43) | Ac-cArrrAr-NH$_2$ | >1000 |
| (SEQ ID NO: 44) | Ac-CaRrRaR-NH$_2$ | 5.6 |
| (SEQ ID NO: 65) | Ac-cvrrrvr-NH$_2$ | 35 |
| (SEQ ID NO: 66) | Ac-cvrrrvr | — |
| (SEQ ID NO: 67) | Ac-Crrrrrr-NH$_2$ | 6.2 |
| (SEQ ID NO: 68) | Ac-carrrer-NH$_2$ | 62 |
| (SEQ ID NO: 69) | Ac-cerrrar-NH$_2$ | 31 |
| (SEQ ID NO: 72) | Ac-cakrrar-NH$_2$ | 35 |
| (SEQ ID NO: 73) | Ac-carkrar-NH$_2$ | 31 |
| (SEQ ID NO: 74) | Ac-carrrar-OH | 31 |
| (SEQ ID NO: 11) | Ac-crrrarr-NH$_2$ | 5.9 |
| (SEQ ID NO: 12) | Ac-crrrrar-NH$_2$ | 0.45 |
| (SEQ ID NO: 13) | Ac-crrrrra-NH$_2$ | 1.1 |
| (SEQ ID NO: 75) | Ac-CARRRAR-NH$_2$ | 58 |
| (SEQ ID NO: 76) | Ac-caarrrrr-NH$_2$ | 4.5 |
| (SEQ ID NO: 77) | Ac-caaarrrrr-NH$_2$ | 4.6 |
| (SEQ ID NO: 78) | Ac-carararar-NH$_2$ | 5.3 |
| (SEQ ID NO: 29) | Ac-arrrar-NH$_2$ | >1000 |
| (SEQ ID NO: 79) | Ac-carrrarar-NH$_2$ | 13 |
| (SEQ ID NO: 80) | crrrrrr-NH$_2$ | 1.1 |
| (SEQ ID NO: 32) | Ac-dHcy rrrrrr-NH$_2$ | 2 |
| (SEQ ID NO: 81) | Ac-c(Benzoyl)rrrrrr-NH$_2$ | 3.6 |
| (SEQ ID NO: 82) | Ac-c(acetyl)rrrrrr-NH$_2$ | 4.1 |

In another study of the structure activity relationship, the contribution of non-cationic amino acids to the potency of the peptides was evaluated by preparing a series of peptides with various D-amino acid residues or glycine (Table 6) or with sterically-hindered non-natural amino acids (Table 7), substituted at various positions in the peptide Ac-carrrar-NH$_2$ (SEQ ID NO:26) and in the peptide Ac-crrarar-NH$_2$ (SEQ ID NO:153). The peptides were administered as an IV bolus to normal Sprague Dawley rats at a dose of 0.5 mg/kg. An intravenous (IV) bolus of saline was used as a control. Plasma PTH levels were assessed prior to dosing and 1, 2, 3 and 4 hours after dosing. The results are shown in the tables below, and indicate that: 1) a small amino acid such as alanine, glycine or serine is preferred at position 6 in the Ac-carrrar-NH$_2$ peptide (SEQ ID NO:26), and 2) the alanine in position 2 in Ac-carrrar-NH$_2$ (SEQ ID NO:26) is much more permissive to substitutions and can be substituted with hydrophobic (e.g. D-Val, D-Leu), aromatic (e.g. D-Phe), or polar (e.g. D-Ser, D-Gln) natural amino acids as well as non-natural bulky hydrophobic amino acids (e.g. dNle, dNva) but not acidic ones, and that 3) the alanine residue in position 4 of the Ac-crrarar-NH$_2$ (SEQ ID NO:25) peptide is also very permissive to substitutions and can accommodate most types of natural amino acids (as well as non-natural bulky hydrophobic amino acids (e.g. dNle, dNva) but is not permissive to amino acids that affect secondary conformation, namely glycine or proline or amino acids with acidic side chain.

TABLE 6

Activity of Exemplary Peptide Compounds

| SEQ ID NO. | Compound Structure* | In vivo activity in normal rats** 0.5 mg/kg IV bolus % PTH AUC of saline control |
|---|---|---|
| Saline | Saline | 100 |
| SEQ ID NO: 83 | Ac-carrrfr-NH$_2$ | 177 |
| SEQ ID NO: 84 | Ac-carrrir-NH$_2$ | 161 |
| SEQ ID NO: 85 | Ac-carrrlr-NH$_2$ | 140 |
| SEQ ID NO: 68 | Ac-carrrer-NH$_2$ | 81 |
| SEQ ID NO: 87 | Ac-carrrvr-NH$_2$ | 79 |
| SEQ ID NO: 88 | Ac-carrrpr-NH$_2$ | 76 |
| SEQ ID NO: 89 | Ac-carrrhr-NH$_2$ | 48 |
| SEQ ID NO: 90 | Ac-carrrqr-NH$_2$ | 41 |
| SEQ ID NO: 91 | Ac-carrrtr-NH$_2$ | 18 |
| SEQ ID NO: 92 | Ac-carrrsr-NH$_2$ | 6 |
| SEQ ID NO: 93 | Ac-carrrGr-NH$_2$ | 5 |
| SEQ ID NO: 94 | Ac-cerrrar-NH$_2$ | 103 |
| SEQ ID NO: 95 | Ac-cGrrrar-NH$_2$ | 45 |
| SEQ ID NO: 96 | Ac-cirrrar-NH$_2$ | 33 |
| SEQ ID NO: 97 | Ac-cprrrar-NH$_2$ | 30 |
| SEQ ID NO: 98 | Ac-clrrrar-NH$_2$ | 26 |
| SEQ ID NO: 99 | Ac-cqrrrar-NH$_2$ | 24 |
| SEQ ID NO: 100 | Ac-ctrrrar-NH$_2$ | 23 |
| SEQ ID NO: 101 | Ac-cvrrrar-NH$_2$ | 19 |
| SEQ ID NO: 102 | Ac-csrrrar-NH$_2$ | 13 |
| SEQ ID NO: 103 | Ac-chrrrar-NH$_2$ | 1 |
| SEQ ID NO: 104 | Ac-cfrrrar-NH$_2$ | 0 |
| SEQ ID NO: 105 | Ac-crrGrar-NH$_2$ | 69 |
| SEQ ID NO: 106 | Ac-crrprar-NH$_2$ | 68 |
| SEQ ID NO: 107 | Ac-crrerar-NH$_2$ | 56 |
| SEQ ID NO: 108 | Ac-crrtrar-NH$_2$ | 13 |
| SEQ ID NO: 109 | Ac-crrhrar-NH$_2$ | 9 |
| SEQ ID NO: 110 | Ac-crrfrar-NH$_2$ | 6 |
| SEQ ID NO: 111 | Ac-crrsrar-NH$_2$ | 4 |
| SEQ ID NO: 112 | Ac-crrqrar-NH$_2$ | 4 |
| SEQ ID NO: 113 | Ac-crrvrar-NH$_2$ | 3 |
| SEQ ID NO: 114 | Ac-crrlrar-NH$_2$ | 1 |
| SEQ ID NO: 115 | Ac-crrirar-NH$_2$ | 0 |

*Bolded font indicates respective substitution of alanine residues in Ac-carrrar-NH$_2$ (SEQ ID NO: 6) or Ac-crrarar-NH$_2$ (SEQ ID NO: 25).
**PTH reduction following 0.5 mg/kg IV administration in isoflurane-anesthetized normal rats-PTH was measured at 1, 2, 3 and 4 hours post administration and cumulative AUC was calculated. PTH data were calculated according to the following formula: AUC$_{cmpd\ treated}$/AUC$_{saline\ control}$*100.

TABLE 7

Activity of Exemplary Peptide Compounds

| SEQ ID NO. | Compound Structure* | In vivo activity in normal rats* 0.5 mg/kg IV bolus % PTH AUC of saline control** |
|---|---|---|
| Saline | Saline | 100 |
| SEQ ID NO: 116 | Ac-crr-Sar-rar-NH$_2$ | 141 |
| SEQ ID NO: 117 | Ac-carrr-Sar-r-NH$_2$ | 111 |
| SEQ ID NO: 118 | Ac-c-Nma-rrr-Nma-r-NH$_2$ | 105 |
| SEQ ID NO: 119 | Ac-crrar-Nma-r-NH$_2$ | 101 |
| SEQ ID NO: 120 | Ac-c-Aib-rrr-Aib-r-NH$_2$ | 94 |
| SEQ ID NO: 121 | Ac-crr-Nma-rar-NH$_2$ | 86 |
| SEQ ID NO: 122 | Ac-carrr-Nma-r-NH$_2$ | 74 |
| SEQ ID NO: 123 | Ac-c-Aib-rrrar-NH$_2$ | 70 |
| SEQ ID NO: 124 | Ac-carrr-Aib-r-NH$_2$ | 68 |
| SEQ ID NO: 125 | Ac-c-Sar-rrr-Sar-r-NH$_2$ | 65 |
| SEQ ID NO: 126 | Ac-crrar-Sar-r-NH$_2$ | 62 |
| SEQ ID NO: 127 | Ac-c-Nma-rrrar-NH$_2$ | 56 |
| SEQ ID NO: 128 | Ac-c-Sar-rrrar-NH$_2$ | 50 |
| SEQ ID NO: 129 | Ac-carrr-Nle-r-NH$_2$ | 64 |
| SEQ ID NO: 130 | Ac-c-dNle-rrr-dNle-r-NH$_2$ | 54 |
| SEQ ID NO: 131 | Ac-carrr-dNva-r-NH$_2$ | 54 |
| SEQ ID NO: 132 | Ac-c-dNva-rrr-dNva-r-NH$_2$ | 27 |
| SEQ ID NO: 133 | Ac-crrar-dNle-r-NH$_2$ | 26 |
| SEQ ID NO: 134 | Ac-c-dNle-rrrar-NH$_2$ | 10 |
| SEQ ID NO: 135 | Ac-crrar-dNva-r-NH$_2$ | 8 |
| SEQ ID NO: 136 | Ac-c-dNva-rrrar-NH$_2$ | 7 |
| SEQ ID NO: 137 | Ac-crr-dNva-rar-NH$_2$ | 3 |
| SEQ ID NO: 138 | Ac-crr-dNle-rar-NH$_2$ | 3 |

*Bolded font indicates respective substitution of alanine residues in Ac-carrrar-NH$_2$ (SEQ ID NO: 26) or Ac-crrarar-NH$_2$ (SEQ ID NO: 25).
Sar = the non-natural amino acid Sarcosine;
Nma = N-methyl alanine;
AiB = amino isobutyric acid;
dNva = D-Norvaline;
dNle = D-Norleucine
**PTH reduction following 0.5 mg/kg IV administration in isoflurane-anesthetized normal rats-PTH was measured at 1, 2, 3 and 4 hours post administration and cumulative AUC was calculated. PTH data were calculated according to the following formula: AUC$_{cmpd\ treated}$/AUC$_{saline\ control}$*100.

TABLE 8

Activity of Exemplary Peptide Compounds

| SEQ ID NO. | Compound Structure* | In vivo activity in normal rats** 0.5 mg/kg IV bolus % PTH AUC of saline control |
|---|---|---|
| Saline | Saline | 100 |
| SEQ ID NO: 97 | Ac-c(C)arrrar-NH$_2$ | 8 |
| SEQ ID NO: 101 | Ac-c(GS)rrrrr-NH$_2$ | 12 |

TABLE 8-continued

Activity of Exemplary Peptide Compounds

| SEQ ID NO. | Compound Structure* | In vivo activity in normal rats** 0.5 mg/kg IV bolus % PTH AUC of saline control |
|---|---|---|
| SEQ ID NO: 139 | Ac-c(dHcy)arrrar-NH$_2$ | 32 |
| SEQ ID NO: 140 | Ac-c(Mpa)arrrar-NH$_2$ | 25 |
| SEQ ID NO: 141 | Ac-c(Ac-C)arrrar-NH$_2$ | 38 |
| SEQ ID NO: 142 | Ac-c(c)arrrar-NH$_2$ | 0 |
| SEQ ID NO: 143* | Ac-c(C-PEG20**)rrrrrr-NH$_2$ | 25 |
| SEQ ID NO: 144** | Ac-c(C-PEG40**)rrrrrr-NH$_2$ | 15 |
| SEQ ID NO: 145 | CEEEEEE<br>|<br>Ac-crrrrrr-NH$_2$ | 40 |
| SEQ ID NO: 145<br><br>SEQ ID NO: 26 | CEEEEEE<br>|<br>Ac-carrrar-NH$_2$ | 42 |
| SEQ ID NO: 25<br><br>SEQ ID NO: 25 | Ac-crrarar-NH$_2$<br>|<br>Ac-crrarar-NH$_2$ | 2 |
| SEQ ID NO: 26<br><br>SEQ ID NO: 26 | Ac-carrrar-NH$_2$<br>|<br>Ac-carrrar-NH$_2$ | 1 |

*Bolded font showing in parenthesis indicates respective thiol-containing conjugating groups.
GS = oxidized glutathione; dHcy = D-homocysteine; Mpa = Mercaptopropionic acid; PEG = polyethylene glycol.
**PTH reduction following 0.5 mg/kg IV administration in isoflurane-anesthetized normal rats-PTH was measured at 1, 2, 3 and 4 hours post administration and cumulative AUC was calculated. PTH data were calculated according to the following formula: AUC$_{cmpd\ treated}$/AUC$_{saline\ control}$*100.
***Compound was dosed at 10 mg/kg (~equivalent molarity to a 0.5 mg/kg non-PEGylated peptide)
****Compound was dosed at 20 mg/kg (~equivalent molarity to a 0.5 mg/kg non-PEGylated peptide)

B. Histamine Response and Structure-Activity Relationship Studies

Poly-cationic compounds have been reported in the literature to trigger the release of the active biogenic amine histamine. See Church et al., *J. Immunol,* 128(5):2116-2121 (1982); Lagunoff et al., *Ann. Rev. Pharmacol. Toxicol.,* 23:331-51 (1983). It is thought that histamine release is a result of mast cell and basophil activation occurring in a Gαi dependent manner. See Aridor et al., *J. Cell Biol.,* 111(3): 909-17 (1990). Reducing or eliminating this physiological reaction is desirable, inter alia, for improving the therapeutic margin of cationic peptide calcimimetics for the treatment of SHPT.

Studies were conducted to evaluate the histamine release induced upon in vivo administration of the compounds described herein. In a first study, described in Example 6, dosing by IV bolus or infusion into normal Sprague Dawley rats was used to evaluate histamine release associated with various compounds. To evaluate the effect of net positive charge on the histamine release associated with a compound, peptides containing 4 to 7 cationic (arginine) residues were generated and tested for their ability to trigger histamine release in vivo, according to the procedure described in Example 6. The tested peptides included (i) Ac-crrrr-NH$_2$ (SEQ ID NO:4), (ii) Ac-crrrrr-NH$_2$ (SEQ ID NO:5), (iii) Ac-crrrrrr-NH$_2$ (SEQ ID NO:6) and (iv) Ac-crrrrrrrr-NH$_2$ (SEQ ID NO:41).

Figure 3:
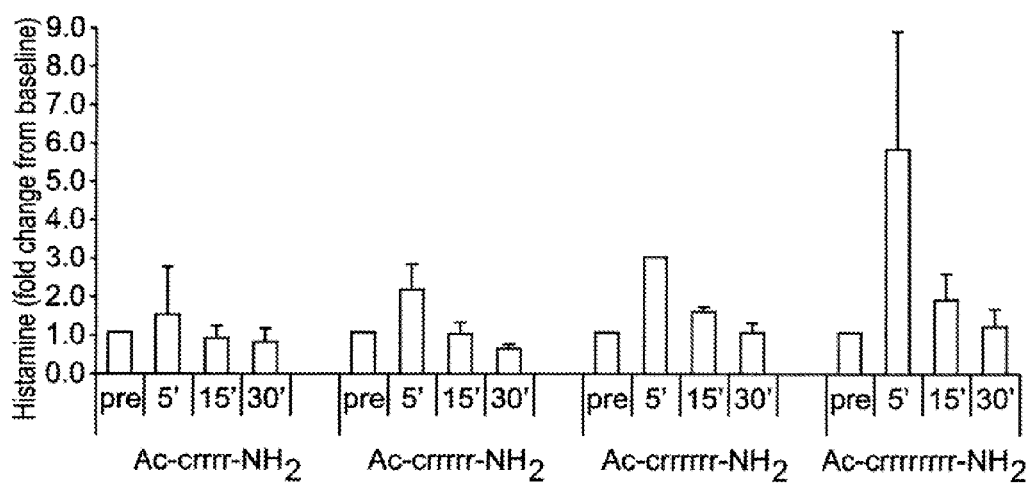
FIG. 3 is a bar graph that compares the release of histamine following IV bolus administration of various compounds in normal Sprague Dawley rats, where the compounds Ac-crrrr-NH$_2$ (SEQ ID NO:4), Ac-crrrrr-NH$_2$ (SEQ ID NO:5), Ac-crrrrrr-NH$_2$ (SEQ ID NO:6) and Ac-crrrrrrrr-NH$_2$ (SEQ ID NO:41) were dosed in an equimolar IV bolus dose of 2.1 µmol/kg, and plasma histamine was measured before dosing (pre-dose), 5, 15 and 30 minutes after dosing.

As shown in FIG. 3, when an equivalent number of moles of each peptide was administered by IV bolus to normal rats, SEQ ID NO:41 (8 arginine residues) displayed the largest induction of histamine. Other compounds with fewer Arg residues, including SEQ ID NO:6 (6 arginine residues), SEQ ID NO:5 (5 arginine residues), and SEQ ID NO:4 (4 arginine residues), also produced a spike in histamine level, but to a lesser extent compared to SEQ ID NO:41. SEQ ID NO:6, SEQ ID NO:5 and SEQ ID NO:4 generated milder responses in their histamine release activity (~2-3 fold above baseline). SEQ ID NO:5 and SEQ ID NO:4 were, however, less potent than SEQ ID NO:6 with respect to lowering plasma PTH.

Because the PTH-reducing activity of Ac-crrrrrr-NH$_2$ (SEQ ID NO:6) was accompanied by lack of a histamine response, additional evaluations were conducted based on Ac-crrrrrr-NH$_2$ (SEQ ID NO:6) in order to evaluate whether it was possible to still further decrease histamine response without sacrificing PTH-lowering activity. As will be shown in the data below, substitution of cationic (arginine) residues in Ac-crrrrrr-NH$_2$ (SEQ ID NO:6) with non-cationic (alanine) residues was performed to produce a series of analogs with an overall reduced net charge and reduced charge density. Of these analogs, both Ac-cararrr-NH$_2$ (SEQ ID NO:15) and Ac-carrrar-NH$_2$ (SEQ ID NO:26) were associated with lack of a histamine response when administered to rats by IV bolus. Importantly, these two peptides retained their potent calcimimetic properties and were able to reduced PTH secretion in both normal rats and rats with renal dysfunction.

The compound Ac-crrrrrr-NH$_2$ identified as SEQ ID NO:6 (2.1 μmole/kg=2.3 mg/kg) triggered an observable histamine response of about 2-3 fold over baseline compared to 6-9 fold with SEQ ID NO:41 when dosed by IV bolus (given over less than 1 minute) in normal rats. The histamine release triggered by Ac-crrrrrr-NH$_2$ (SEQ ID NO:6) peaked at 5 minutes after dosing and returned to baseline levels 15 minutes later (FIG. 3). Further reduction in the number of charged subunits to 5 and 4 arginine residues per peptide (SEQ ID NO:5 and SEQ ID NO:4, respectively) further reduced the histamine response as compared with the longer oligo-arginine peptides; however, a 2-3 fold increase in histamine over baseline was still observed 5 minutes after IV bolus dosing (FIG. 3). These results suggest a relationship between the net charge of the peptide and the associated release of histamine. It is also noted that arginine-rich peptides with fewer than 7 arginines are quite limited in their ability to enter cells, suggesting that cell penetration is not required to trigger histamine release.

The histamine release associated with the PTH-lowering compounds Ac-crrrrrr-NH$_2$ (SEQ ID NO:6) and Ac-c(C) arrrar-NH$_2$ (SEQ ID NO:3) was evaluated in vivo. The compound Ac-c(C)arrrar-NH$_2$ (SEQ ID NO:3) has the following structure:

(SEQ ID NO: 3)

This conjugate structure is denoted herein as Ac-c(C)arrrar-NH$_2$ (SEQ ID NO:273) where the L-Cys residue linked to the thiol-containing residue in the X$_1$ subunit of the compound (here, a D-Cys residue) via a Cys-Cys disulfide bond, is placed in parenthesis in the formula. This notation is used throughout to designate that the parenthetical moiety is linked to a second thiol-containing group. Relative to Ac-crrrrrr-NH$_2$ (SEQ ID NO:6) the compound Ac-c(C)arrrar-NH$_2$ (SEQ ID NO: 3) has two cationic (arginine) residues substituted with uncharged (alanine) residues at subunit positions $X_2$ and $X_6$. In addition, the D-Cys residue in the $X_1$ position is conjugated to an L-Cys residue.

Figure 4:
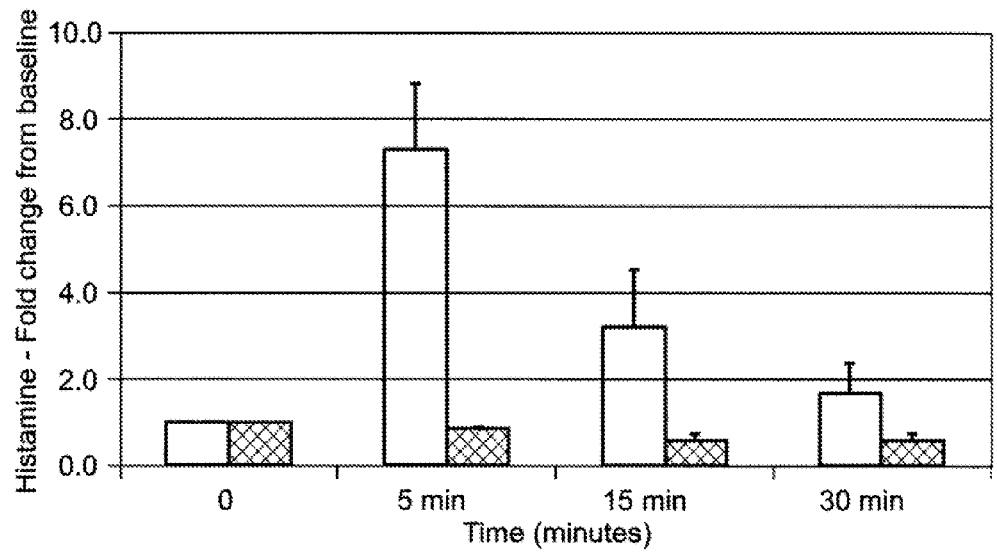
FIG. 4 is a bar graph that compares the release of histamine following IV bolus administration of two compounds in normal Sprague Dawley rats, where the compounds Ac-c(C)arrrar-NH$_2$ (SEQ ID NO:3, cross hatched bars) and Ac-crrrrrr-NH$_2$ (SEQ ID NO:6, open bars) were dosed at 3 mg/kg, and plasma histamine was measured before dosing (time zero) and 5, 15 and 30 minutes after dosing.

These two compounds were administered to isoflurane-anesthetized rats (Sprague Dawley) at 3 mg/kg by intravenous (IV) bolus (given over less than 1 minute). Blood was drawn prior to dosing and a 5, 15 and 30 minutes after dosing. Histamine concentration was measured, and the fold change in blood histamine concentration relative to the pre-dose blood histamine concentration is shown in FIG. 4. The compound Ac-crrrrrr-NH$_2$ (SEQ ID NO:6, open bars) induced a histamine response, observed at the data point 5 minutes post-dosing where a 7-fold increase in histamine level was observed. The compound Ac-c(C)arrrar-NH$_2$ (SEQ ID NO:3, cross hatched bars) induced no apparent histamine response, as seen by the data points at 5, 10 and 15 minutes post dosing where the histamine level was not increased relative to the pre-dose (time zero) histamine level.

To further evaluate the relationship between compound structure and histamine release, a series of compounds was prepared and assessed for their ability to trigger induction of histamine in an in vitro assay using rat peritoneal mast cells. In this assay, compounds are incubated at 10 µM for 15 minutes at 37° C. with cells isolated from peritoneal lavage of SD rats. Following incubation, cell medium is collected and histamine is determined. The data is shown in Table 9.

TABLE 9

In vitro Histamine Induction in Rat Peritoneal Mast Cells of Exemplary Peptide Compounds

| SEQ ID NO. | Compound Sequence | *Histamine in vitro Fold change of non-treated at 10 uM* |
|---|---|---|
| Saline | Saline | 1.0 |
| SEQ ID NO: 6 | Ac-crrrrrr-NH$_2$ | 11.5 |
| SEQ ID NO: 8 | Ac-carrrrr-NH$_2$ | 6.6 |
| SEQ ID NO: 9 | Ac-crarrrr-NH$_2$ | 6.8 |
| SEQ ID NO: 10 | Ac-crrarrr-NH$_2$ | 5.3 |
| SEQ ID NO: 11 | Ac-crrrarr-NH$_2$ | 5.0 |
| SEQ ID NO: 12 | Ac-crrrrar-NH$_2$ | 5.0 |
| SEQ ID NO: 13 | Ac-crrrrra-NH$_2$ | 4.1 |
| SEQ ID NO: 15 | Ac-cararrr-NH$_2$ | 2.5 |
| SEQ ID NO: 22 | Ac-caarrrr-NH$_2$ | 1.2 |
| SEQ ID NO: 17 | Ac-crraarr-NH$_2$ | 1.3 |
| SEQ ID NO: 146 | Ac-crrrraa-NH$_2$ | 1.9 |
| SEQ ID NO: 26 | Ac-carrrar-NH$_2$ | 1.4 |
| SEQ ID NO: 3 | Ac-c(C)arrrar-NH$_2$ | 0.6 |
| SEQ ID NO: 16 | Ac-carrarr-NH$_2$ | 1.4 |
| SEQ ID NO: 19 | Ac-carrrra-NH$_2$ | 1.3 |
| SEQ ID NO: 23 | Ac-crarrar-NH$_2$ | 1.5 |
| SEQ ID NO: 18 | Ac-crararr-NH$_2$ | 1.4 |
| SEQ ID NO: 20 | Ac-crarrra-NH$_2$ | 1.1 |
| SEQ ID NO: 25 | Ac-crrarar-NH$_2$ | 1.2 |
| SEQ ID NO: 14 | Ac-crrarra-NH$_2$ | 1.6 |
| SEQ ID NO: 130 | Ac-c-dNle-rrr-dNle-r-NH$_2$ | 9.2 |
| SEQ ID NO: 132 | Ac-c-dNva-rrr-dNva-r-NH$_2$ | 4.1 |
| SEQ ID NO: 28 | Ac-c(C)rrarar-NH$_2$ | 0.7 |
| SEQ ID NO: 24 | Ac-craarrr-NH$_2$ | 1.0 |
| SEQ ID NO: 21 | Ac-crrrraar-NH$_2$ | 1.0 |
| SEQ ID NO: 134 | Ac-c-dNle-rrrar-NH$_2$ | 2.2 |
| SEQ ID NO: 129 | Ac-carrr-dNle-r-NH$_2$ | 2.6 |
| SEQ ID NO: 136 | Ac-c-dNva-rrrar-NH$_2$ | 2.1 |
| SEQ ID NO: 131 | Ac-carrr-dNva-r-NH$_2$ | 1.8 |
| SEQ ID NO: 133 | Ac-crrar-dNle-r-NH$_2$ | 4.3 |
| SEQ ID NO: 135 | Ac-crrar-dNva-r-NH$_2$ | 1.1 |
| SEQ ID NO: 95 | Ac-cGrrrar-NH$_2$ | 1.5 |
| SEQ ID NO: 99 | Ac-cqrrrar-NH$_2$ | 1.9 |
| SEQ ID NO: 103 | Ac-chrrrar-NH$_2$ | 1.6 |
| SEQ ID NO: 96 | Ac-cirrrar-NH$_2$ | 3.0 |
| SEQ ID NO: 98 | Ac-clrrrar-NH$_2$ | 2.2 |
| SEQ ID NO: 97 | Ac-cprrrar-NH$_2$ | 0.8 |
| SEQ ID NO: 102 | Ac-csrrrar-NH$_2$ | 0.9 |

TABLE 9-continued

In vitro Histamine Induction in Rat Peritoneal Mast Cells of Exemplary Peptide Compounds

| SEQ ID NO. | Compound Sequence | *Histamine in vitro Fold change of non-treated at 10 uM* |
|---|---|---|
| SEQ ID NO: 100 | Ac-ctrrrar-NH$_2$ | 1.1 |
| SEQ ID NO: 101 | Ac-cvrrrar-NH$_2$ | 1.5 |
| SEQ ID NO: 93 | Ac-carrrGr-NH$_2$ | 0.9 |
| SEQ ID NO: 90 | Ac-carrrqr-NH$_2$ | 0.9 |
| SEQ ID NO: 89 | Ac-carrrhr-NH$_2$ | 2.0 |
| SEQ ID NO: 84 | Ac-carrrir-NH$_2$ | 1.8 |
| SEQ ID NO: 85 | Ac-carrrlr-NH$_2$ | 2.5 |
| SEQ ID NO: 88 | Ac-carrrpr-NH$_2$ | 1.0 |
| SEQ ID NO: 92 | Ac-carrrsr-NH$_2$ | 1.2 |
| SEQ ID NO: 91 | Ac-carrrtr-NH$_2$ | 1.7 |
| SEQ ID NO: 87 | Ac-carrrvr-NH$_2$ | 1.2 |
| SEQ ID NO: 147 | Ac-cakkkak-NH$_2$ | 1.1 |
| SEQ ID NO: 72 | Ac-cakrrar-NH$_2$ | 1.1 |
| SEQ ID NO: 73 | Ac-carkrar-NH$_2$ | 1.4 |
| SEQ ID NO: 105 | Ac-crrGrar-NH$_2$ | 1.8 |
| SEQ ID NO: 112 | Ac-crrqrar-NH$_2$ | 1.2 |
| SEQ ID NO: 109 | Ac-crrhrar-NH$_2$ | 2.3 |
| SEQ ID NO: 115 | Ac-crrirar-NH$_2$ | 3.4 |
| SEQ ID NO: 114 | Ac-crrlrar-NH$_2$ | 4.5 |
| SEQ ID NO: 106 | Ac-crrprar-NH$_2$ | 1.1 |
| SEQ ID NO: 111 | Ac-crrsrar-NH$_2$ | 2.0 |
| SEQ ID NO: 108 | Ac-crrtrar-NH$_2$ | 1.2 |
| SEQ ID NO: 113 | Ac-crrvrar-NH$_2$ | 1.9 |
| SEQ ID NO: 104 | Ac-cfrrrar-NH$_2$ | 6.8 |
| SEQ ID NO: 83 | Ac-carrrfr-NH$_2$ | 4.0 |
| SEQ ID NO: 68 | Ac-carrrer-NH$_2$ | 1.3 |
| SEQ ID NO: 110 | Ac-crrfrar-NH$_2$ | 6.2 |
| SEQ ID NO: 107 | Ac-crrerar-NH$_2$ | 0.6 |
| SEQ ID NO: 86 | Ac-carrkar-NH$_2$ | 1.0 |
| SEQ ID NO: 70 | Ac-carrrak-NH$_2$ | 0.9 |
| SEQ ID NO: 148 | Ac-cararar-NH$_2$ | 0.6 |
| SEQ ID NO: 25 | Ac-crrarar-NH$_2$ <br> \| <br> Ac-carrrar-NH$_2$ | 9.3 |
| SEQ ID NO: 149 | Ac-crrarGr-NH$_2$ | 1.6 |
| SEQ ID NO: 150 | Ac-crrarqr-NH$_2$ | 1.6 |
| SQ ID NO: 151 | Ac-crrarhr-NH$_2$ | 2.5 |
| SEQ ID NO: 152 | Ac-crrarir-NH$_2$ | 4.1 |
| SEQ ID NO: 153 | Ac-ca(DAP)rrar-NH$_2$ | 1.6 |
| SEQ ID NO: 154 | Ac-ca(dHar)(dHar)(dHar)ar-NH$_2$ | 2.7 |

*Method set forth in Example 7
Abbreviations: See Example 7

To further evaluate the relationship between compound structure and histamine release, a series of compounds was prepared assessed for their ability to trigger induction of histamine in an in vivo assays. The data is shown in Table 10.

TABLE 10

In vivo Histamine Induction of Exemplary Peptide Compounds

| SEQ ID NO. | Compound Structure | * Histamine response in vivo Fold change from pre-dose levels 5' post injection 2 mg/kg IV bolus |
|---|---|---|
| Saline | Saline | 1.0 |
| SEQ ID NO: 6 | Ac-crrrrrr-NH$_2$ | 2.7 |
| SEQ ID NO: 26 | Ac-carrrar-NH$_2$ | 1.0 |
| SEQ ID NO: 25 | Ac-crrarar-NH$_2$ | 0.9 |
| SEQ ID NO: 15 | Ac-cararrr-NH$_2$ | 1.0 |
| SEQ ID NO: 18 | Ac-crararr-NH$_2$ | 1.1 |
| SEQ ID NO: 20 | Ac-crarrra-NH$_2$ | 1.0 |

TABLE 10-continued

In vivo Histamine Induction of Exemplary Peptide Compounds

| SEQ ID NO. | Compound Structure | *Histamine response in vivo Fold change from pre-dose levels 5' post injection 2 mg/kg IV bolus |
|---|---|---|
| SEQ ID NO: 19 | Ac-carrrra-NH$_2$ | 0.9 |
| SEQ ID NO: 23 | Ac-crarrar-NH$_2$ | 0.8 |
| SEQ ID NO: 18 | Ac-crararr-NH$_2$ | 1.0 |
| SEQ ID NO: 27 | Ac-c(C)arrrar-NH$_2$ | 0.9 |
| SEQ ID NO: 28 | Ac-c(C)rrarar-NH$_2$ | 0.9 |

*Method set forth in Example 7.

Accordingly, and as can be appreciated in view of the PTH data and the histamine data described hereinabove, in one embodiment, a compound that has activity to decrease PTH level in a subject in the absence of a histamine response is contemplated. In certain embodiments, absence of a histamine response intends a dose of the compound that produces a less than 10-fold, more preferably 8-fold, still more preferably 5-fold, and even still more preferably 3-fold, increase in histamine, measured in vitro in an assay as described herein, where the fold change is determined based on histamine levels before incubation with the compound and after 15 minutes incubation with compound. In a specific embodiment, the histamine response is determined in an in vitro assay using rat peritoneal mast cells isolated from peritoneal lavage of normal Sprague Dawley rats, and where the fold change is determined based on histamine levels before incubation with the compound and after 15 minutes incubation with compound. In the studies conducted herein, the in vitro evaluation of histamine release was performed using isolated rat peritoneal mast cells isolated by peritoneal lavage using cold HBSS+25 mM HEPES pH 7.4 containing heparin (5 u/mL). Cells were washed twice in stimulation buffer (HBSS+25 mM HEPES pH 7.4) and incubated with 10 µM of compound in stimulation buffer (HBSS+25 mM HEPES pH 7.4) for 15 minutes in a 96-well plate (106/well) at 37° C. Cell supernatant was analyzed for histamine using histamine EIA kit (Cayman #589651).

In another embodiment, a compound that has activity to decrease PTH level in a subject in the absence of an clinical histamine response is contemplated. As used herein, absence of a "clinical histamine response" intends is that a therapeutically effective amount of a compound as described herein is administered to the subject without producing a clinically adverse increase in plasma or blood histamine as measured 5-10 minutes after completion of dosing or over the course of treatment. For example, when a compound required to produce a desired therapeutic effect is administered to a subject by bolus (as used herein "bolus" means administered over one minute or less) produced an increase in plasma or blood histamine 5-10 minutes after completion of dosing that is less than 15-fold, 10-fold, 9-fold, 8-fold, 7-fold, 6-fold, 5-fold, 4-fold, 3-fold, 2-fold above pre-dose levels.

As can be appreciated from the studies described above, in one embodiment, the compound comprises a sequence of 3 to 35 amino acid residues, wherein a plurality of positively charged amino acid residue subunits is present in the sequence. In some embodiments, the described compounds comprise 5 to 25 subunits, and in a preferred embodiment each subunit is an amino acid residue. In other embodiments, the described compounds comprise 6 to 12 subunits. In still other embodiments, the described compounds comprise 3 to 9 amino acid subunits. In alternative embodiments the described compounds comprise 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 subunits.

The subunits of the described compounds are, in one embodiment, independently selected from natural or unnatural amino acids, or their analogs, and may have either the L- or D-configuration (except for glycine which is achiral). Glycine, the aliphatic residues alanine, valine, leucine, or isoleucine, proline, the hydroxyl residues serine and threonine, the acidic residues aspartic acid and glutamic acid, the amide residues asparagine, and glutamine, the basic residues lysine and arginine, histidine, the aromatic residues phenylalanine, tyrosine, and tryptophan, and the sulfur-containing residues methionine and cysteine are all contemplated for use in the described compounds. The number of positively charged subunits, and their density can affect the potency of the compound for reducing PTH. In some embodiments, positively charged subunits are separated by one or more other subunits ("separating subunits"). In one embodiment, the separating subunits are alanine residues. In some embodiments, the chirality of the separating subunit affects the potency of the compound.

Positively charged amino acid residues of the described compounds may be a specific natural or unnatural residue, or analog thereof, having either the L- or D-configuration (e.g., L-arginine) that is repeated in the sequence, or may be a variety of natural or unnatural residues, or analogs thereof, having either the L- or D-configuration. In some embodiments, the compound is a peptide comprised of from 3 to 20 positively charged amino acid residues, 6 to 12 positively charged amino acid residues, 3 to 9 positively charged amino acid residues. In some embodiments, the peptides comprise 3, 4, 5, 6, 7, 8, 9, 10, 11, 12, 13, 14, 15, 16, 17, 18, 19, or 20 positively charged amino acid residues.

In some embodiments, the positively charged amino acid residues are independently selected from natural amino acids. In some embodiments, the positively charged amino acid residues are independently selected from natural and/or unnatural amino acids. In some embodiments, the positively charged amino acid residues are independently selected from the group consisting of arginine, lysine, histidine, 2,3-diaminopropionic acid (Dap), 2,4-diaminobutyric acid (Dab), ornithine, and homoarginine. In a preferred embodiment, the positively charged amino acid residues are arginine residues.

In some embodiments, the compound is a peptide and is a single continuous peptide chain or strand. In other embodiments, the compound is a peptide that is branched. In still other embodiments, the peptide is conjugated to one or more thiol-containing moieties (each, a "thiol-containing conjugating group" or a "conjugating group"). In a preferred embodiment, and as merely illustrative, the peptide compound is conjugated to a Cys conjugating group, via a (—S—S—) disulfide bond (for example -Cys-Cys-). As used herein, the term "compound" is intended to encompass both such peptides and such conjugates.

The compounds typically comprise one or more thiol moieties, preferably one or more reactive thiol moieties. Subunits that have a thiol group include non-amino acid compounds having a thiol group and amino acids with a thiol group. The thiol group of the thiol-containing subunit may be in a conjugated form (e.g., via a disulfide bond to a conjugating group) or in an unconjugated form (i.e., as a reduced thiol). In a preferred embodiment, when the thiol group is in either an unconjugated form or a conjugated form, it is capable of forming a disulfide bond with a thiol-containing group. The thiol-containing residue may be located at any position along the peptide chain, including the amino terminus, the carboxy terminus, or some other position. In a preferred embodiment, the thiol-containing residue or subunit may be located at the amino terminus. In other embodiments, the thiol-containing residue or subunit may be located at the carboxy terminus or within the peptide sequence.

Some representative examples of thiol-containing residues include, without limitation, cysteine, mercaptopropionic acid, homo-cysteine, and penicillamine. When the thiol-containing residue contains a chiral center, it may be present in the L- or D-configuration. In a preferred embodiment, the thiol-containing residue is cysteine.

In some embodiments, the cross-linkage between the thiol containing subunit at the $X_1$ position in the compound and the thiol-containing conjugating group may be cleavable and/or exchangeable with other thiol-containing conjugating groups such as cysteine (e.g., by reduction of the disulfide linkage) in vivo to yield a biologically active form of the compound. In this way, the conjugate may function as a pro-drug of the compound. A conjugating group also may be used to modify the physicochemical, pharmacokinetic and/or pharmacodynamic properties of the described compounds (e.g., conjugation via a disulfide linkage to a large PEGylated moiety to enhance the pharmacokinetics).

In some embodiments, the compound is a peptide comprised of the amino acid sequence $(X_{aa1})$-$(X_{aa2})$-$(X_{aa3})$-$(X_{aa4})$-$(X_{aa5})$-$(X_{aa6})$-$(X_{aa7})$ (SEQ ID NO:155), wherein $(X_{aa1})$ is a thiol-containing amino acid residue, $(X_{aa2})$ is a non-cationic amino acid residue, $(X_{aa3})$ is any amino acid residue, $(X_{aa4})$ is any amino acid residue, $(X_{aa5})$ is a cationic amino acid residue, $(X_{aa6})$ is a non-cationic residue, and $(X_{aa7})$ is any amino acid residue. The peptide may be modified at the N-terminus, the C-terminus, or both. In a preferred embodiment, the peptide is modified at both the N-terminus and C-terminus by acetylation and amidation, respectively.

In some embodiments, a peptide comprises the amino acid sequence (D-Cys)-$(X_{aa2})$-$(X_{aa3})$-$(X_{aa4})$-$(X_{aa5})$-$(X_{aa6})$-$(X_{aa7})$ (SEQ ID NO:156), wherein $(X_{aa2})$ is a non-cationic amino acid residue, $(X_{aa3})$ is any amino acid residue, $(X_{aa4})$ is any amino acid residue, $(X_{aa5})$ is selected from the group consisting of D-Arg, L-Arg, D-Lys and L-Lys, $(X_{aa6})$ is a non-cationic residue, and $(X_{aa7})$ is any amino acid residue. The peptide may have an N-terminal cap, a C-terminal cap, or both. In a preferred embodiment, the peptide has both an N-terminal cap and a C-terminal cap.

In some embodiments, a peptide comprises the amino acid sequence (D-Cys)-$(X_{aa2})$-$(X_{aa3})$-$(X_{aa4})$-$(X_{aa5})$-$(X_{aa6})$-$(X_{aa7})$ (SEQ ID NO:157), wherein $(X_{aa2})$, $(X_{aa3})$ and $(X_{aa4})$ are, independently, any amino acid residue (but in a preferred embodiment are, independently, selected from the group consisting of D-Ala, D-Val, D-Leu, D-NorVal, and D-NorLeu), $(X_{aa5})$ and $(X_{aa7})$ are, independently, any cationic amino acid residue (but in a preferred embodiment are, independently, selected from the group consisting of D-Arg, L-Arg, D-Lys and L-Lys), $(X_{aa6})$ is a non-cationic amino acid residue (in a preferred embodiment, selected from the group consisting of D-Ala, D-Val, D-Leu, D-NorVal and D-NorLeu). The peptide may have an N-terminal cap, a C-terminal cap, or both. In a preferred embodiment, the peptide has both an N-terminal cap and a C-terminal cap.

In some embodiments, a peptide comprises the amino acid sequence (D-Cys)-$(X_{aa2})$-$(X_{aa3})$-$(X_{aa4})$-$(X_{aa5})$-$(X_{aa6})$-$(X_{aa7})$ (SEQ ID NO:158), wherein $(X_{aa2})$ is a non-cationic amino acid residue, $(X_{aa3})$ is any amino acid residue, $(X_{aa4})$ is any amino acid residue, $(X_{aa5})$ is selected from the group consisting of D-Arg, L-Arg, D-Lys and L-Lys, $(X_{aa6})$ is a non-cationic residue, and $(X_{aa7})$ is any amino acid residue. The peptide may have an N-terminal cap, a C-terminal cap, or both. In a preferred embodiment, the peptide has both an N-terminal cap and a C-terminal cap.

In some embodiments, a peptide comprises the amino acid sequence (D-Cys)-(D-Ala)-$(X_{aa3})$-$(X_{aa4})$-(D-Arg)-(D-Ala)-$(X_{aa7})$ (SEQ ID NO:159), wherein $(X_{aa3})$ is any cationic amino acid residue, $(X_{aa4})$ is any cationic amino acid residue, and $(X_{aa7})$ is any cationic amino acid residue. The peptide may have an N-terminal cap, a C-terminal cap, or both. In a preferred embodiment, the peptide has both an N-terminal cap and a C-terminal cap.

In some embodiments, a peptide comprises the amino acid sequence (D-Cys)-$(X_{aa2})$-$(X_{aa3})$-(D-Ala)-(D-Arg)-(D-Ala)-$(X_{aa7})$ (SEQ ID NO:160), wherein $(X_{aa2})$, $(X_{aa3})$ and $(X_{aa7})$ are, independently, any cationic amino acid residue. The peptide may have an N-terminal cap, a C-terminal cap, or both. In a preferred embodiment, the peptide has both an N-terminal cap and a C-terminal cap.

Another embodiment is a calcimimetic peptide, comprising a sequence of amino acids linked by peptide bonds, wherein the sequence comprises 5 to 10 amino acid residues, and wherein the sequence comprises an amino terminus, a carboxy terminus, at least one thiol-containing residue, and from 3 to 9 positively charged residues. In one embodiment, the at least one thiol-containing residue is a cysteine residue. In another aspect, the cysteine residue is positioned at the amino terminus of the peptide. In certain embodiment, the cysteine residue is an L-Cys residue, a D-Cys residue, or an L- or D-homoCys residue. In other embodiments, the amino acid residues of the peptide are D-amino acids or L-amino acids.

Also encompassed within the scope of the claimed compounds are peptidomimetic molecules that comprise approximately seven subunits, wherein at least one subunit contains a thiol moiety, preferably a reactive thiol moiety, and other subunits are a plurality of non-cationic subunits, and from 1 to 4 positively charged subunits. Such peptidomimetic molecules may comprise non-peptide bonds between two or more of the subunits. The various features of the compounds discussed above apply generally to the peptidomimetic molecule. For example, as discussed above, the subunits used to construct the molecules can be naturally-occurring amino acids, or residues with non-natural side chains, the termini of the modules can be capped or non-capped in the manner discussed above. Similarly, the amino acid residues of the molecule can be L- or D-amino acid residues. Also as discussed above, the thiol-containing residues can be in a reduced or oxidized form with any of the thiol-containing moieties discussed above.

Many peptidomimetic frameworks and methods for their synthesis have been developed (Babine, R. E.; Bender, S. L., Chem. Rev., 97:1359, 1997; Hanessian, S.; et al., Tetrahedron, 53:12789, 1997; Fletcher, M. D.; Cambell, M. C., Chem. Rev., 98:763, 1998); Peptidomimetics Protocols; Kazmierski W. M., Ed.; Methods in Molecular Medicine Series, Vol. 23; Humana Press, Inc.; Totowa, N.J. (1999).

Conjugates

In some embodiments, the compound is chemically cross-linked to a thiol-containing conjugating group via a disulfide bond between the thiol of the compound and a thiol from the conjugating group. The thiol-containing conjugating group can be a small molecule, such as cysteine, or a macromolecule, such as a polypeptide containing a cysteine residue.

Examples of suitable thiol-containing conjugating groups include cysteine, glutathione, thioalkyl, moieties such as thiobenzyl, mercaptopropionic acid, N-acetylated cysteine, cysteamide, N-acetylcysteamide, homocysteine, penicillamine and poly (ethylene glycol) (PEG) modified (referred to as "PEGylated") thiols such as PEGylated cysteine or a duplication of the compound (i.e., to form a homodimer linked by a disulfide linkage). In a preferred embodiment, the thiol-containing conjugating group is cysteine. Other cysteine homologs are also contemplated for use as thiol-containing conjugating groups, either alone or comprised in a larger conjugating group. Similarly, stereoisomers of cysteine, homocysteine, and cysteamide are suitable for use as thiol-containing moieties. Conjugating groups can be used to improve chemical stability and therefore shelf-life of a pharmaceutical product. In certain embodiments the thiol-containing conjugating group and the peptide are the same (i.e., the conjugate is a dimer), which unexpectedly showed very good chemical stability compared to heterologous conjugating group such as cysteine. Without being bound by theory, presumably when the thiol-containing conjugating group and the peptide are the same, then any disproportionation (e.g., scrambling of the conjugating group) will reconstitute the original dimer compound. In contrast, disproportionation of a compound with a heterologous conjugating group such as cysteine can lead to formation of homodimers of the peptide plus cystine (cysteine-cysteine homodimer) plus residual parent compound. A homo-dimer of the peptide (i.e., conjugating group and the peptide are the same) would be converted to a cysteine conjugated form of the peptide in vivo due to the high concentration of reduced cysteine in systemic circulation.

In some embodiments, the teachings include a disulfide conjugate of a thiol-containing conjugating group and a peptide comprising the amino acid sequence $(X_{aa1})$-$(X_{aa2})$-$(X_{aa3})$-$(X_{aa4})$-$(X_{aa5})$-$(X_{aa6})$-$(X_{aa7})$ (SEQ ID NO:155), wherein $(X_{aa1})$ is an amino acid residue with a thiol-containing moiety, $(X_{aa2})$ is a non-cationic amino acid residue, $(X_{aa3})$ is any amino acid residue, $(X_{aa4})$ is any amino acid residue, $(X_{aa5})$ is a cationic amino acid residue, $(X_{aa6})$ is a non-cationic residue, and $(X_{aa7})$ is any amino acid residue. The peptide may have an N-terminal cap, a C-terminal cap, or both. In a preferred embodiment, the peptide has both an N-terminal cap and a C-terminal cap. In a preferred embodiment, the thiol-containing conjugating group is selected from the group consisting of D-Cys, L-Cys, a peptide containing D-Cys, and a peptide containing L-Cys. When the thiol-containing conjugate group is an amino acid or a peptide, it may have an N-terminal cap, a C-terminal cap, or both. In a preferred embodiment, the thiol-containing conjugate group has both an N-terminal cap and a C-terminal cap. In some embodiments, the thiol-containing conjugating group is itself a peptide comprising the amino acid sequence of SEQ ID NO:155. In some embodiments, the thiol-containing conjugating group and the peptide are the same (i.e., the conjugate is a dimer).

In some embodiments, the teachings include a conjugate of a thiol-containing conjugating group and a peptide comprising the amino acid sequence (D-Cys)-$(X_{aa2})$-$(X_{aa3})$-$(X_{aa4})$-$(X_{aa5})$-$(X_{aa6})$-$(X_{aa7})$ (SEQ ID NO:156), wherein $(X_{aa2})$ is a non-cationic amino acid residue, $(X_{aa3})$ is any amino acid residue, $(X_{aa4})$ is any amino acid residue, $(X_{aa5})$ is selected from the group consisting of D-Arg, L-Arg, D-Lys and L-Lys, $(X_{aa6})$ is a non-cationic residue, and $(X_{aa7})$ is any amino acid residue. The peptide may have an N-terminal cap, a C-terminal cap, or both. In a preferred embodiment, the peptide has both an N-terminal cap and a C-terminal cap. In a preferred embodiment, the thiol-containing conjugating group is selected from the group consisting of D-Cys, L-Cys, a peptide containing D-Cys, and a peptide containing L-Cys. When the thiol-containing conjugate group is an amino acid or a peptide, it may have an N-terminal cap, a C-terminal cap, or both. In a preferred embodiment, the thiol-containing conjugate group has both an N-terminal cap and a C-terminal cap. In some embodiments, the thiol-containing conjugating group is itself a peptide comprising the amino acid sequence of SEQ ID NO:156. In some embodiments, the thiol-containing conjugating group and the peptide are the same (i.e., the conjugate is a dimer).

In some embodiments, the teachings include a conjugate of a thiol-containing conjugating group and a peptide comprising the amino acid sequence (L-Cys)-$(X_{aa2})$-$(X_{aa3})$-$(X_{aa4})$-$(X_{aa5})$-$(X_{aa6})$-$(X_{aa7})$ (SEQ ID NO:183), wherein $(X_{aa2})$ is a non-cationic amino acid residue, $(X_{aa3})$ is any amino acid residue, $(X_{aa4})$ is any amino acid residue, $(X_{aa5})$ is selected from the group consisting of D-Arg, L-Arg, D-Lys and L-Lys, $(X_{aa6})$ is a non-cationic residue, and $(X_{aa7})$ is any amino acid residue. The peptide may have an N-terminal cap, a C-terminal cap, or both. In a preferred embodiment, the peptide has both an N-terminal cap and a C-terminal cap. In a preferred embodiment, the thiol-containing conjugating group is selected from the group consisting of D-Cys, L-Cys, a peptide containing D-Cys, and a peptide containing L-Cys. When the thiol-containing conjugate group is an amino acid or a peptide, it may have an N-terminal cap, a C-terminal cap, or both. In a preferred embodiment, the thiol-containing conjugate group has both an N-terminal cap and a C-terminal cap. In some embodiments, the thiol-containing conjugating group is itself a peptide comprising the amino acid sequence of SEQ ID NO:183. In some embodiments, the thiol-containing conjugating group and the peptide are the same (i.e., the conjugate is a dimer).

In some embodiments, the teachings include a conjugate of a thiol-containing conjugating group and a peptide comprising the amino acid sequence (D-Cys)-(D-Ala)-$(X_{aa3})$-$(X_{aa4})$-(D-Arg)-(D-Ala)-$(X_{aa7})$ (SEQ ID NO:161), wherein $(X_{aa3})$ is any amino acid residue, $(X_{aa4})$ is any amino acid residue, and $(X_{aa7})$ is any amino acid residue. The peptide may have an N-terminal cap, a C-terminal cap, or both. In a preferred embodiment, the peptide has both an N-terminal cap and a C-terminal cap. In a preferred embodiment, the thiol-containing conjugating group is selected from the group consisting of D-Cys, L-Cys, a peptide containing D-Cys, and a peptide containing L-Cys. When the thiol-containing conjugate group is an amino acid or a peptide, it may have an N-terminal cap, a C-terminal cap, or both. In a preferred embodiment, the thiol-containing conjugate group has both an N-terminal cap and a C-terminal cap. In some embodiments, the thiol-containing conjugating group is itself a peptide comprising the amino acid sequence of SEQ ID NO:161. In some embodiments, the thiol-containing conjugating group and the peptide are the same (i.e., the conjugate is a dimer).

III. Methods of Use

In one aspect, methods to prevent, treat or ameliorate hyperparathyroidism, bone disease and/or other hypercalcemic disorders by administering the compounds described herein are contemplated. As illustrated above, the compounds have activity to decrease PTH and/or calcium levels in a target tissue or tissues, or in a subject. In certain embodiments, the described compounds are capable of decreasing PTH and/or calcium levels when a therapeutically effective amount of the compound is administered to a subject in need of such treatment. The methods of use will now be described with reference to Examples 3 and 8-11.

Figure 5:
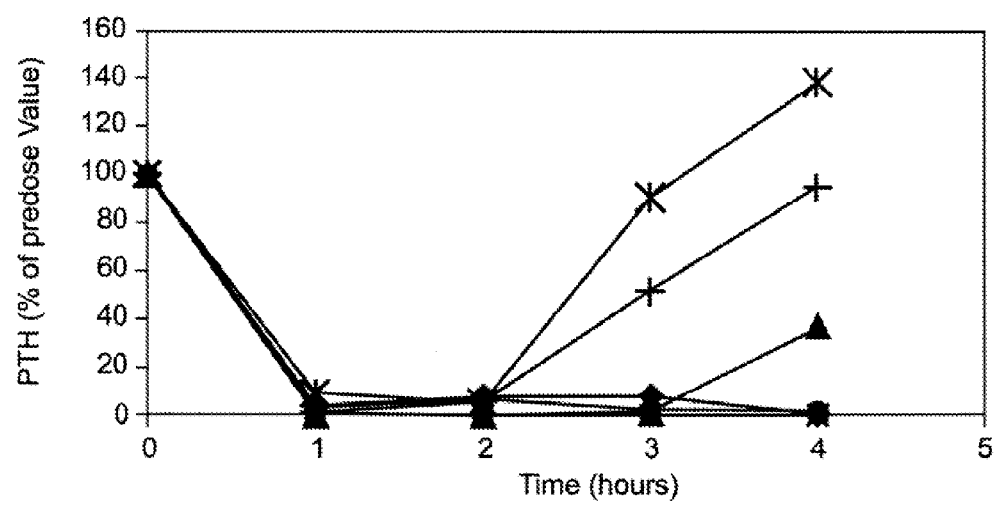
FIG. 5 is a graph of parathyroid hormone level, as percent of the baseline pre-dose value, as a function of time, in hours, in normal rats dosed with 0.5 mg/kg by IV bolus of Ac-crrrrrr-NH$_2$ (SEQ ID NO:6, diamonds), Ac-carrrrr-NH$_2$ (SEQ ID NO:8, squares), Ac-crarrrr-NH$_2$ (SEQ ID NO:9, triangles), Ac-crrarrr-NH$_2$ (SEQ ID NO:10, x symbols), Ac-crrrarr-NH$_2$ (SEQ ID NO:11, * symbols), Ac-crrrrar-NH$_2$ (SEQ ID NO:12, circles) or Ac-crrrrra-NH$_2$ (SEQ ID NO:13, + symbols)

With reference again to Example 3, and as discussed above with respect to Table 1, the series of compounds where a cationic (arginine) residue was sequentially replaced with a non-cationic residue (alanine) were administered to rats. FIG. 5 shows the time profile of each compound's ability to reduce blood PTH and the duration of action of the varying compounds. In FIG. 5, the compounds Ac-crrrrrr-NH$_2$ (SEQ ID NO:6, diamonds), Ac-carrrrr-NH$_2$ (SEQ ID NO:8, squares) and Ac-crrarrr-NH$_2$ (SEQ ID NO:10, x symbols) and Ac-crrtrar-NH$_2$ (SEQ ID NO:12, circles) were potent in vivo, as evidenced by the decrease in percent PTH of predose baseline to essentially zero and provided a duration of potency, where the PTH blood concentration remained decreased for at least four hours. The compounds Ac-crarrrr-NH$_2$ (SEQ ID NO:9, triangles), Ac-crrrarr-NH$_2$ (SEQ ID NO:11, * symbols) and Ac-crrrrra-NH$_2$ (SEQ ID NO:13, + symbols) decreased percent PTH of baseline for about 2-3 hours, and thereafter the blood concentration of PTH began to increase. Substitution of the cationic (arginine) residue at subunit positions 5 or 7 of Ac-crrrrrr-NH$_2$ (SEQ ID NO:6) impacted the duration of PTH lowering activity.

Figure 6A:
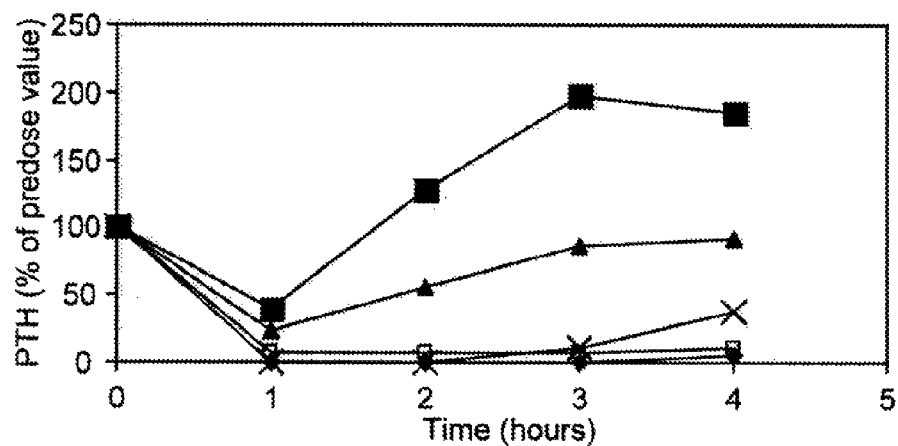
FIGS. 6A-6B are graphs of parathyroid hormone level, as percent of the baseline pre-dose value, as a function of time, in hours, in healthy rats dosed with 0.5 mg/kg by IV bolus of Ac-carrrar-NH$_2$ (SEQ ID NO:26, open diamonds), Ac-crrarar-NH$_2$ (SEQ ID NO:25, open squares), Ac-caarrrr-NH$_2$ (SEQ ID NO:22, triangles), Ac-crraarr-NH$_2$ (SEQ ID NO:17, closed squares), Ac-c(C)arrrar-NH$_2$ (SEQ ID NO:3, diamonds FIG. 6B), Ac-craarrr-NH$_2$ (SEQ ID NO:24, x symbols in FIG. 6A); Ac-c(C)rrarar-NH$_2$ (SEQ ID NO:28, x symbols, FIG. 6B)
Figure 6B:
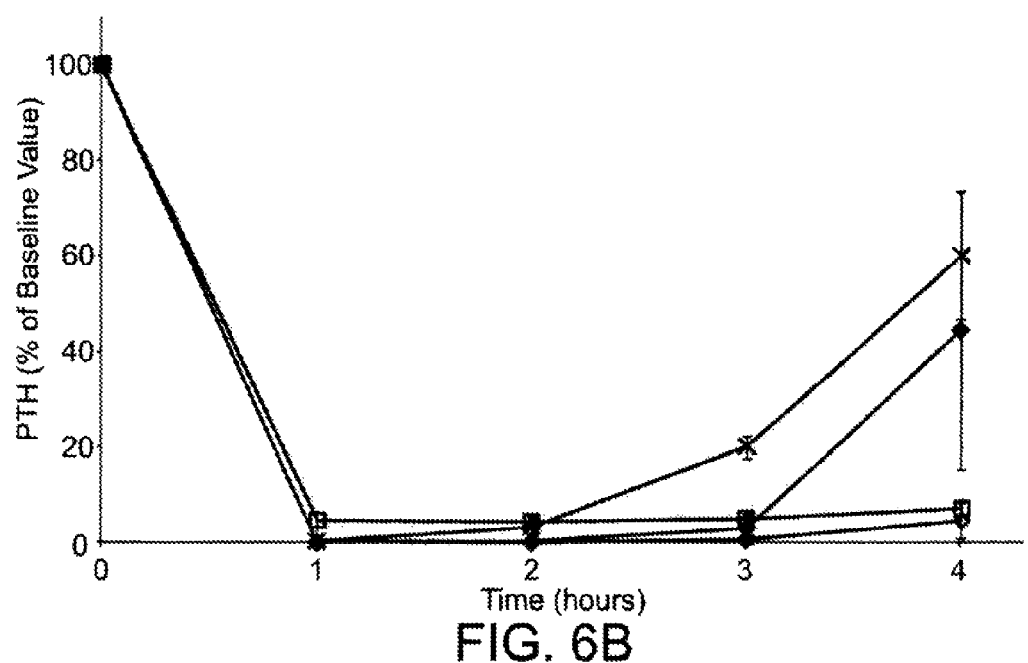

The profile of PTH reduction for a series of compounds containing double amino acid substitutions was also evaluated. Selected compounds set forth in Table 2, above, were administered to normal rats by IV bolus at a dose of 0.5 mg/kg and the reduction in PTH relative to predose PTH blood level was evaluated. Data are shown in FIGS. 6A-6B, where the compound are identified as follows: Ac-carrrar-NH$_2$ (SEQ ID NO:26, open diamonds), Ac-crrarar-NH$_2$ (SEQ ID NO:25, open squares), Ac-caarrrr-NH$_2$ (SEQ ID NO:22, triangles), Ac-crraarr-NH$_2$ (SEQ ID NO:17, circles), Ac-c(C)arrrar-NH$_2$ (SEQ ID NO:3, diamonds FIG. 6B), Ac-c(C)rrarar-NH$_2$ (SEQ ID NO:28, x symbols, FIG. 6B).

Figure 7:
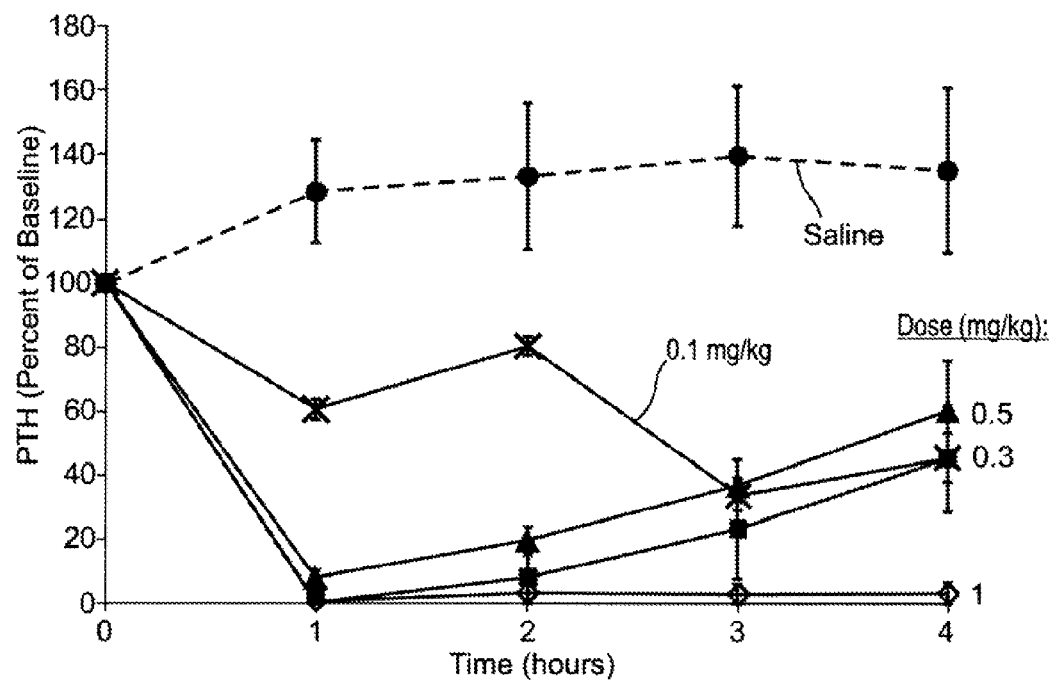
FIG. 7 shows the decrease in parathyroid hormone levels in the blood as a function of time, for the compound Ac-c(C)arrrar-NH$_2$ (SEQ ID NO:3) administered as an IV bolus to normal Sprague Dawley rats at doses of 1 mg/kg (diamonds), 0.5 mg/kg (squares), 0.3 mg/kg (triangles), and 0.1 mg/kg (x symbols). An intravenous (IV) bolus of saline (circles) was used as a control. Plasma PTH levels were assessed prior to dosing and at 1, 2, 3 and 4 hours after dosing.

Another study was done to further evaluate the potency of the compound Ac-c(C)arrrar-NH$_2$ (SEQ ID NO: 3). The compound was intravenously administered to normal rats, as detailed in Example 2, at doses of 1 mg/kg, 0.5 mg/kg, 0.3 mg/kg, and 0.1 mg/kg. Plasma PTH levels were assessed prior to dosing and for 4 hours thereafter. FIG. 7 shows the results, where the PTH blood concentration is shown as percent of the baseline pre-dose value. A dose-related PTH reduction was observed following a single IV bolus administration with the highest dose of 1 mg/kg (diamonds) had the largest reduction in PTH, followed by the 0.5 mg/kg (squares), 0.3 mg/kg (triangles), and 0.1 mg/kg (x symbols). The saline control is shown by the circles symbols. As seen, the peptide when administered at a therapeutically effective dose achieves a reduction in PTH of greater than 50% relative to the concentration of PTH before dosing ("baseline"). Specifically, the peptide when administered at doses of greater than 0.1 mg/kg reduced PTH concentration to less than 90% of the baseline PTH concentration 1 hour after IV administration. These doses of the peptide identified as SEQ ID NO:3 also achieved an area under the curve (AUC) of less than 50%, the AUC calculated as the sum of the PTH concentration values at the time points of 1, 2, 3 and 4 hours, normalized by the AUC for the saline control at the same time points, multiplied by 100.

Figure 8:
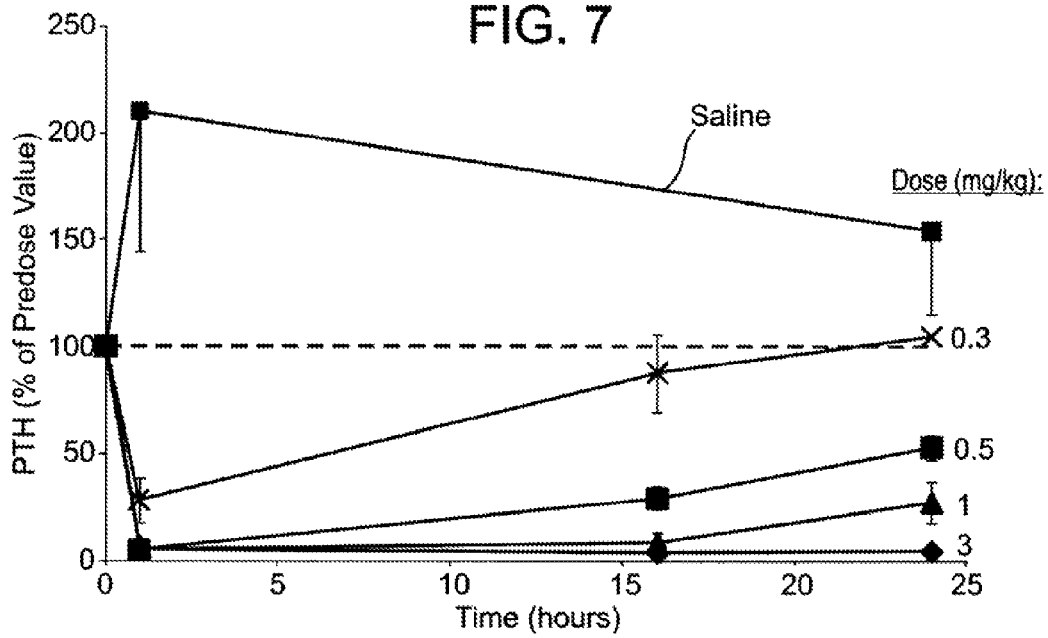
FIG. 8 is a graph of parathyroid hormone level, as percent of the baseline pre-dose value, as a function of time, in hours, in rats with acute renal insufficiency (1K1C model), in rats with 1K1C model of acute renal insufficiency, where the rats were dosed via IV bolus with the compound Ac-c(C)arrrar-NH$_2$ (SEQ ID NO:3) at doses of 3 mg/kg (diamonds), 1 mg/kg (triangles), 0.5 mg/kg (squares) and 0.3 mg/kg (x symbols), or saline (squares); the dashed line in FIG. 8 indicating baseline PTH level pre-dosing.

The same compound was also tested in subjects (rats) with renal insufficiency. In this study, the 1K1C model of acute renal insufficiency was used to evaluate a the compound Ac-c(C)arrrar-NH$_2$ (SEQ ID NO: 3) to characterize its PTH-lowering activity in a renal dysfunction environment. The model is described in Example 1A. The compound was intravenously administered as a bolus to renally compromised animals (rats) at doses of 3 mg/kg (n=2), 1 mg/kg (n=5), 0.5 mg/kg (n=6) and 0.3 mg/kg (n=5). A control group of animals was dosed with saline. Plasma PTH levels were assessed prior to dosing and for several hours thereafter. FIG. 8 shows the results, where the saline treated animals (squares) had an increased PTH concentration relative to the starting PTH level. At various doses of SEQ ID NO:3, a dose-dependant effect was observed on the duration and extent of PTH reduction. Animals treated with the lowest dose of 0.3 mg/kg (x symbols) exhibiting reduced PTH at the earliest time point and an increase in PTH between hours 1-24 after dosing. The dose levels of 3 mg/kg (diamonds), 1 mg/kg (triangles) and 0.5 mg/kg (squares) provided a reduced PTH blood concentration for more than 15 hours, and for the highest dose, for more than 24 hours.

In another study to evaluate the effect of substituting cationic subunits with uncharged subunits, as exemplified by alanine amino acid residues, in the context of a subject with renal insufficiency, an analog of Ac-crrrrrr-NH$_2$ (SEQ ID NO:6) was generated and tested for its ability to lower PTH in 1K1C model animals following a 1 mg/kg single intravenous administration. In the tested analog Ac-carrrar-NH$_2$ (SEQ ID NO:26), the cationic subunits at positions X$_2$ and X$_6$ of Ac-crrrrrr-NH$_2$ (SEQ ID NO:6) were substituted with uncharged amino acids.

Figure 9:
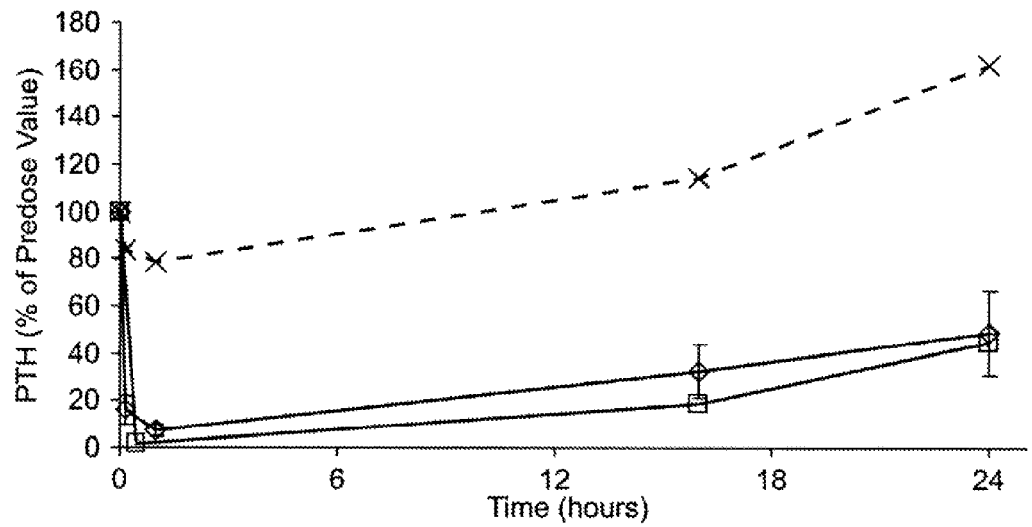
FIG. 9 is a graph of parathyroid hormone level, as percent of the baseline pre-dose value, as a function of time, in hours, in rats dosed intravenously with saline (x symbols) or with the compounds Ac-crrrrrr-NH$_2$ (SEQ ID NO:6, open diamonds), and Ac-carrrar-NH$_2$ (SEQ ID NO:26, open squares) at 1 mg/kg via a 30-minute IV infusion, where plasma PTH levels were assessed prior to dosing, 16 hours and 24 hours after dosing.

As shown in FIG. 9, Ac-carrrar-NH$_2$ (SEQ ID NO:26, open squares) shows activity that is equivalent to Ac-crrrrrr-NH$_2$ (SEQ ID NO:6, open diamonds) at the dose tested (1 mg/kg) with similar extended duration of action over 24 hours. The analog of Ac-crrrrrr-NH$_2$ (SEQ ID NO:6) with uncharged subunit substitutions was found to retain activity and may, in fact, have in vivo potency and duration of action superior to that of the compound identified as SEQ ID NO:6. In the compound, Ac-carrrar-NH$_2$ (SEQ ID NO:26), D-Arg residues at positions X$_2$ and X$_6$ were substituted with D-Ala residues relative to the compound identified as SEQ ID NO:6.

Significantly, as discussed above, administration of the compound Ac-carrrar-NH$_2$ (SEQ ID NO:26) was not accompanied with histamine release, an undesirable side-effect that is seen with Ac-crrrrrr-NH$_2$ (SEQ ID NO:6) and other similar compounds when administered at higher doses (>1 mg/kg) by IV bolus. The marked attenuation of the histamine release with the compound identified SEQ ID NO:26 increases the therapeutic margin between the desired PTH-lowering activity and the undesired histamine-inducing activity following administration by IV bolus. Accordingly, in a preferred embodiment, compounds having activity to reduce PTH concentration in vivo in the absence of a histamine response are provided. Accordingly, in one embodiment, a compound is provided that has activity to decrease PTH where the compound when administered an a subject, human or otherwise, decreases PTH level to below 50% of the pre-dose level within one hour after dosing. In a specific embodiment, a compound that has significant activity to decrease PTH intends a compound that when administered to a normal rat decreases PTH level to below 50% of the pre-dose level within one hour after dosing by IV bolus.

In another study, detailed in Example 8, compounds in the form of a conjugate, where the thiol-containing subunit in position $X_1$ was linked through a disulfide linkage to an L-Cys residue. These compounds have the following structures:

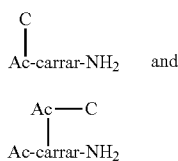

(SEQ ID NO: 3)

and (SEQ ID NO:141)

Figure 10:
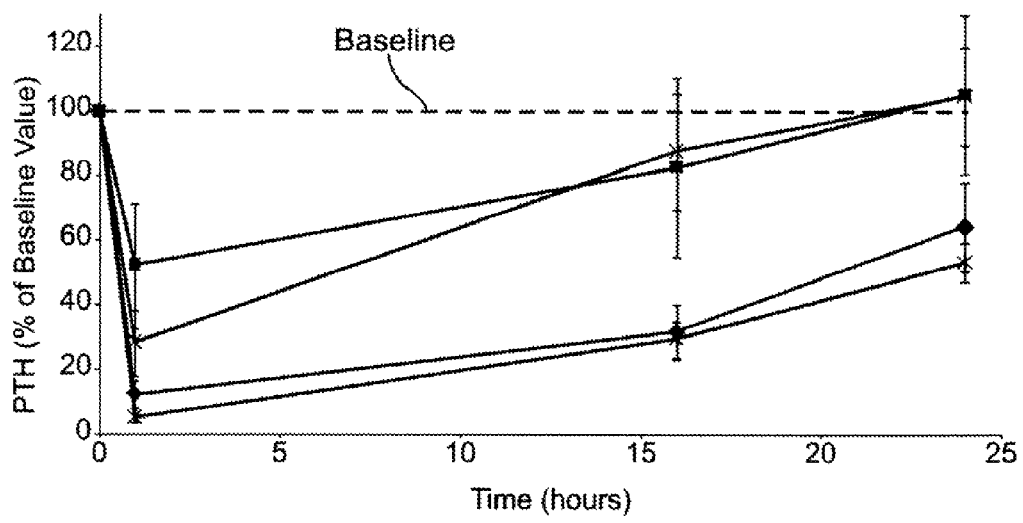
FIG. 10 is a graph of parathyroid hormone level, as percent of the baseline pre-dose value, as a function of time, in hours, in rats with acute renal insufficiency (1K1C model), where the rats were dosed via IV bolus with the compounds Ac-c(C)arrrar-NH$_2$ (SEQ ID NO:3, squares, * symbols) and Ac-c(Ac-C)arrrar-NH$_2$ (SEQ ID NO:146, triangles, diamonds) at doses of 0.3 mg/kg (squares, triangles) and 0.5 mg/kg (*, diamonds)

In the notation used herein, the compound that is linked to the thiol-containing moiety in the $X_1$ subunit is identified parenthetically, where in these exemplary conjugates the compound L-Cys is indicated (C) is linked to the thiol-containing moiety in the $X_1$ subunit: Ac-c(C)arrrar-NH$_2$ (SEQ ID NO:3) and Ac-c(Ac—C)arrrar-NH$_2$ (SEQ ID NO:141). These compounds were administered via IV bolus to animals with acute renal insufficiency (1K1C model) at doses of 0.3 and 0.5 mg/kg, and the results are shown in FIG. 10. The compound Ac-c(C)arrrar-NH$_2$ (SEQ ID NO:3) is represented by squares (0.3 mg/kg, n=5) and * symbols (0.5 mg/kg, n=6) and the compound Ac-c(Ac—C)arrrar-NH$_2$ (SEQ ID NO:141) by triangles (0.3 mg/kg, n=8) and diamonds (0.5 mg/kg, n=7). This in vivo dose response with SEQ ID NO:3 displays a dose-dependent reduction in PTH very similar to Ac-crrrrrr-NH$_2$ (SEQ ID NO:6).

Figure 11:
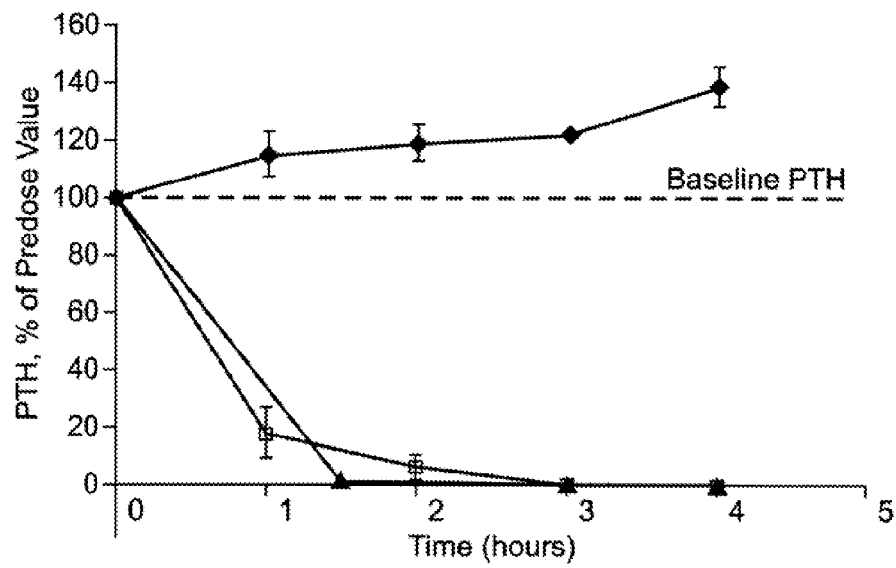
FIG. 11 is a graph of parathyroid hormone level, as percent of the baseline pre-dose value, as a function of time, in hours, in rats treated via micropore-facilitated transdermal delivery of Ac-crrrrrr-NH$_2$ (SEQ ID NO:6, two animals, squares and triangles) or with saline via transdermal delivery (diamonds)

In some of the in vivo studies described herein, the compounds, including compounds in conjugate form where the thiol in the $X_1$ subunit is cross-linked via a disulfide bond to another subunit, were administered as a 30-minute IV infusion. However, it should be noted that shorter infusions (e.g., <5 minutes) or delivery by IV bolus typically produce comparable pharmacodynamic reduction of PTH as a longer 30-minute infusion. Subcutaneous bolus administration also proved to be an efficacious route of delivery that generated a smaller initial drop in PTH but displayed a sustained reduction in PTH similar to the profile seen by the IV route. As shown in FIG. 11, the compound Ac-crrrrrr-NH$_2$ (SEQ ID NO:6), was also administered by micropore-facilitated (e.g., microporation of the stratum corneum) transdermal delivery, and demonstrated a reduction in plasma PTH for the several hours it was monitored. The compound Ac-crrrrrr-NH$_2$ (SEQ ID NO:6), was also administered by the transdermal route after microporation resulting in a reduction in plasma PTH for several hours. Transdermal delivery of Ac-crrrrrr-NH$_2$ (SEQ ID NO:6) provides an addition option for clinical delivery of the described compounds.

To evaluate the effect of administration route on the activity of Ac-crrrrrr-NH$_2$ (SEQ ID NO:6) in the context of a subject with renal insufficiency, rats in the 1K1C model were given 1 mg/kg of the peptide as either a subcutaneous (SC) bolus or a 30-minute IV infusion. Both routes of administration effectively reduced plasma PTH levels for over 24 hours. When Ac-crrrrrr-NH$_2$ (SEQ ID NO:6) was delivered by IV infusion, PTH levels fell rapidly by 80-90% from baseline. By 16 hours after dosing, PTH levels had started to rise although they were still reduced by ~80% from baseline. When Ac-crrrrrr-NH$_2$ (SEQ ID NO:6) was delivered by SC bolus, PTH levels exhibited a more moderate initial drop to ~40% of baseline, but exhibited a similar duration of reduction as when the peptide was delivered by the IV route. Twenty-four hours after dosing, PTH levels in animals dosed by either route had partially rebounded although both still displayed reduced PTH levels that were ~40-60% from baseline. The results showed that this route of administration provides a similar profile with respect to efficacy and duration of PTH reduction as IV administration, thus providing an alternative path for clinical dosing (data not shown).

Accordingly, in a preferred embodiment, a subject having secondary hyperparathyroidism (SHPT) is treated using the described compounds to reduce plasma PTH levels and/or calcium. Untreated SHPT patients with moderately severe hyperparathyroidism often have baseline circulating intact PTH levels >300 pg/ml, and levels that can exceed 600 pg/mL. In a preferred embodiment, the decrease in PTH levels is measured as a decrease in intact PTH below pretreatment baseline levels. In another embodiment the desired decrease in PTH is to bring the plasma PTH levels into generally recognized guidelines established by the National Kidney Foundation or other experts in the treatment of kidney disorders and renal insufficiency.

In another aspect, methods for treating hyperparathyroidism, hypercalcemia and/or bone disease are provided, comprising administering a therapeutically effective amount of a described compound. In another embodiment, the subject can be treated with a described compound in combination with one or more other therapeutically effective agents.

In another aspect, the described compound is administered in an amount effective to reduce PTH or PTH effect. In some embodiments, the reduction in plasma PTH is at least 1%, 2%, 3%, 4%, 5%, 6%, 7%, 8%, 9%, 10%, 11%, 12%, 13%, 14%, 15%, 16%, 17%, 18%, 19%, 20%, 25% or 30% below pretreatment baseline levels for at least 10 hours post administration of the described compound. In specific embodiments, the reduction in plasma PTH is at least 20% at 10 hours post administration. In preferred embodiments, the reduction in plasma PTH is 15 to 40%, preferably 20 to 50%, more preferably 30 to 70% below pretreatment baseline levels for at least 48 hours post administration of the described compound.

In another aspect, the described compound is administered in an amount effective to decrease serum calcium or calcium effect. In some embodiments, the reduction in serum calcium is at least 1%, 2%, 3%, 4%, 5%, 6%, 7%, 8%, 9%, 10%, 11%, 12%, 13%, 14%, 15%, 16%, 17%, 18%, 19%, 20% or 25% below pretreatment levels for at least 10 hours post administration of the polycationic peptide. In some preferred embodiments, the reduction in serum calcium is at least 5% at 10 hours post administration. In some preferred embodiments, the reduction is serum calcium is 5 to 10%, preferably 5 to 20% below pretreatment levels for at least 48 hours post administration of the described compound.

In another aspect, a method for treating hyperparathyroidism and/or hypercalcemia in a subject in need thereof is provided, comprising: administering a therapeutically effective amount of a described compound, whereby PTH and/or calcium is reduced.

Based on the relationship between serum calcium, bone metabolism and PTH, it is thought that the described compounds are beneficial for the treatment of various forms of bone disease and/or hypercalcemia in addition to hyperparathyroidism. The described compounds may have advantages compared to current therapeutic agents, because they may be administered parenterally and may not be associated with gastrointestinal adverse effects, are not metabolized by cytochrome P450 and may result in more effective reductions in plasma PTH and calcium.

As discussed above, the described methods may be used alone or in combination with one or more other therapeutically effective agents. Such other therapeutically effective agents include, but are not limited to, treatment with anti-resorptive bisphosphonate agents, such as alendronate and risedronate; integrin blockers, such as $\alpha_v\beta_3$ antagonists; conjugated estrogens used in hormone replacement therapy, such as PREMPRO™, PREMARIN™ and ENDOMETRION™; selective estrogen receptor modulators (SERMs), such as raloxifene, droloxifene, CP-336,156 (Pfizer) and lasofoxifene; cathespin K inhibitors; vitamin D therapy; vitamin D analogs, such as ZEMPLAR™ (paricalcitol); CALCIJEX® (calcitriol), HECTOROL® (doxercalciferol), ONE-ALPHA® (alfacalcidol) and the analogs in development from Cytochroma known as CTA-018, CTAP201 and CTAP101; other calcimimetics such as Sensipar® (cinacalcet); inhibitors of type II sodium-dependent phosphate transporter family, SLC34 (including the two renal isoforms NaPi-IIa and NaPi-IIc, and the intestinal NaPi-IIb transporter); phosphatonins (including FGF-23, sFRP4, MEPE or FGF-7); low dose PTH treatment (with or without estrogen); calcitonin; inhibitors of RANK ligand; antibodies against RANK ligand, osteoprotegrin; adensosine antagonists; and ATP proton pump inhibitors.

In one embodiment, a described compound is administered at a dose sufficient to decrease both PTH and serum calcium levels. In another embodiment, a described compound is administered at a dose sufficient to decrease PTH without significantly affecting serum calcium levels. In a further embodiment, a described compound is administered at a dose sufficient to increase PTH without significantly affecting serum calcium levels.

Formulations

A pharmaceutical composition comprising a described compound and at least one pharmaceutically acceptable excipient or carrier is provided. Methods of preparing such pharmaceutical compositions typically comprise the step of bringing into association a described compound with a carrier and, optionally, one or more accessory ingredients. The described compounds and/or pharmaceutical compositions comprising same may be formulated into pharmaceutically-acceptable dosage forms by conventional methods known to those of skill in the art. Typically, formulations are prepared by uniformly and intimately bringing into association a described compound with liquid carriers, or finely divided solid carriers, or both, and then, if necessary, shaping the product.

Pharmaceutical compositions of the present invention suitable for parenteral administration comprise one or more described compounds in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, amino acids, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These pharmaceutical compositions may also contain adjuvants such as preservatives, wetting agents, emulsifying agents and dispersing agents. Prevention of the action of microorganisms upon the described compounds may be ensured by the inclusion of various antibacterial and antifungal agents, for example, paraben, chlorobutanol, phenol sorbic acid, and the like. It may also be desirable to include agents to control tonicity, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

For example, a described compound may be delivered to a human in a form of solution that is made by reconstituting a solid form of the drug with liquid. This solution may be further diluted with infusion fluid such as water for injection, 0.9% sodium chloride injection, 5% dextrose injection and lactated ringer's injection. It is preferred that the reconstituted and diluted solutions be used within 4-6 hours for delivery of maximum potency. Alternatively, a described compound may be delivered to a human in a form of tablet or capsule.

Injectable depot forms are made by forming microencapsulated matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the described compounds are administered as pharmaceuticals, to humans and animals, they can be given alone or as a pharmaceutical composition containing, for example, 0.1 to 99% (more preferably, 10 to 30%) of active ingredient in combination with a pharmaceutically acceptable carrier. In other embodiments, the pharmaceutical composition may contain 0.2-25%, preferably 0.5-5% or 0.5-2%, of active ingredient. These compounds may be administered to humans and other animals for therapy by any suitable route of administration, including, e.g., subcutaneous injection, subcutaneous depot, intravenous injection, intravenous or subcutaneous infusion. These compounds may be administered rapidly (within <1 minute) as a bolus or more slowly over an extended period of time (over several minutes, hours or days). These compounds may be delivered daily or over multiple days, continuously or intermittently. In one embodiment, the compounds may be administered transdermally (e.g., using a patch, microneedles, micropores, ointment, microjet or nanojet).

Regardless of the route of administration selected, the described compounds, which may be used in a suitable hydrated form, and/or the pharmaceutical compositions, are formulated into pharmaceutically-acceptable dosage forms by conventional methods known to those of skill in the art.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular described compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the described compounds employed in the pharmaceutical composition at levels lower than that required in order to achieve the desired therapeutic effect and gradually increase the dosage until the desired effect is achieved.

In general, a suitable daily dose of a described compound will be that amount of the compound which is the lowest dose effective to produce a therapeutic effect. Such an effective dose will generally depend upon the factors described above. Generally, intravenous, intramuscular, transdermal, intracerebroventricular and subcutaneous doses of the described compounds for a patient, when used for the indicated effects, will range from about 1 µg to about 5 mg per kilogram of body weight per hour. In other embodiments, the dose will range from about 5 µg to about 2.5 mg per kilogram of body weight per hour. In further embodiments, the dose will range from about 5 µg to about 1 mg per kilogram of body weight per hour.

If desired, the effective daily dose of a described compound may be administered as two, three, four, five, six or more sub-doses administered separately at appropriate intervals throughout the day, optionally, in unit dosage forms. In one embodiment, the described compound is administered as one dose per day. In further embodiments, the compound is administered continuously, as through intravenous or other routes. In other embodiments, the compound is administered less frequently than daily, such as every 2-3 days, in conjunction with dialysis treatment, weekly or less frequently.

The subject receiving this treatment is any animal in need, including primates, in particular humans, and other mammals such as equines, cattle, swine and sheep; and poultry and pets in general.

The described compounds may be administered as such or in admixtures with pharmaceutically acceptable carriers and can also be administered in conjunction with antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

Routes of Administration for Disclosed Compounds

These compounds may be administered to humans and other animals for therapy by any suitable route of administration. As used herein, the term "route" of administration is intended to include, but is not limited to subcutaneous injection, subcutaneous depot, intravenous injection, intravenous or subcutaneous infusion, intraocular injection, intradermal injection, intramuscular injection, intraperitoneal injection, intratracheal administration, intraadiposal administration, intraarticular administration, intrathecal administration, epidural administration, inhalation, intranasal administration, sublingual administration, buccal administration, rectal administration, vaginal administration, intracisternal administration and topical administration, transdermal administration, or administration via local delivery (for example by catheter or stent).

Transdermal drug delivery to the body is a desirable and convenient method for systemic delivery of biologically active substances to a subject, and in particular for delivery of substances that have poor oral bioavailability, such as proteins and peptides. The transdermal route of delivery has been particularly successful with small (e.g., less than about 1,000 Daltons) lipophilic compounds, such as scopolamine and nicotine, that can penetrate the stratum corneum outer layer of the skin, which serves as an effective barrier to entry of substances into the body. Below the stratum corneum is the viable epidermis, which contains no blood vessels, but has some nerves. Deeper still is the dermis, which contains blood vessels, lymphatics and nerves. Drugs that cross the stratum corneum barrier can generally diffuse to the capillaries in the dermis for absorption and systemic distribution.

Technological advances in transdermal delivery have focused on addressing the need in the art to deliver hydrophilic, high molecular weight compounds, such as proteins and peptides, across the skin. One approach involves disruption of the stratum corneum using chemical or physical methods to reduce the barrier posed by the stratum corneum. Skin microporation technology, which involves the creation of micron dimension transport pathways (micropores) in the skin (in particular, the micropores in the stratum corneum) using a minimally invasive technique, is a more recent approach. Techniques to create micropores in the skin (stratum corneum) include thermal microporation or ablation, microneedle arrays, phonophoresis, laser ablation and radiofrequency ablation (Prausnitz and Langer (2008) *Nat. Biotechnology* 11:1261-68; Arora et al., *Int. J. Pharmaceutics*, 364:227 (2008); Nanda et al., *Current Drug Delivery*, 3:233 (2006); Meidan et al. *American J. Therapeutics*, 11:312 (2004)).

As noted above, PTH secretion is regulated by the CaSR which is expressed on the cell surface of parathyroid cells. Thus, in order to activate the CaSR, the agent or compound must be delivered to the parathyroid cell. Transdermal delivery of calcimimetic agents must achieve delivery across the stratum corneum and provide systemic exposure to reach the parathyroid cell. To date, the art has not demonstrated whether a calcimimetic compound can be delivered transdermally in an amount sufficient for therapeutic benefit and in particular in an amount sufficient for decreasing PTH and/or the treatment, attenuation, lessening and/or relief hypercalcemia.

In addition to calcimimetics, 1,25-$(OH)_2$ vitamin $D_3$ analogs are the most commonly used treatments for patients with hyperparathyroidism associated with chronic kidney disease and end stage renal disease. Vitamin D analogs act by facilitating intestinal absorption of dietary calcium, and reduce PTH levels by inhibiting PTH synthesis and secretion. While intravenous and oral delivery of vitamin D has been used therapeutically, to date, the art has not demonstrated whether vitamin D analogs, such as ZEMPLAR™

(paricalcitol), CALCIJEX® (calcitriol), ONE-ALPHA® (alfacalcidol) and HECTOROL® (doxercalciferol) can be delivered transdermally in an amount sufficient for therapeutic benefit and in particular in an amount sufficient for decreasing parathyroid hormone (PTH). In addition, the art has not demonstrated whether the co-administration by transdermal delivery of a calcimimetic agent in combination with a vitamin D analog (either as separate formulations or as a co-formulation) in amounts sufficient for therapeutic benefit, and in particular in amounts sufficient for decreasing PTH and provide effective treatment for patients suffering from hyperparathyroidism.

The calcimimetic agents may be administered across the stratum corneum, and/or other layers of the epidermis, for local or systemic delivery, for decreasing parathyroid hormone (PTH) and/or treating hypercalcemia. In one embodiment, the calcimimetic agent is delivered via microporation. Any one of a number of techniques for microporation is contemplated, and several are briefly described.

Microporation can be achieved by mechanical means and/or external driving forces, to breach the stratum corneum to deliver the calcimimetic agents described herein through the surface of the skin and into the underlying skin layers and/or the bloodstream.

In a first embodiment, the microporation technique is ablation of the stratum corneum in a specific region of the skin using a pulsed laser light of wavelength, pulse length, pulse energy, pulse number, and pulse repetition rate sufficient to ablate the stratum corneum without significantly damaging the underlying epidermis. The calcimimetic agent is then applied to the region of ablation. Another laser ablation microporation technique, referred to as laser-induced stress waves (LISW), involves broadband, unipolar and compressible waves generated by high-power pulsed lasers. The LISWs interact with tissues to disrupt the lipids in the stratum corneum, creating intercellular channels transiently within the stratum corneum. These channel, or micropores, in the stratum corneum permit entry of the calcimimetic agent.

Sonophoresis or phonophoresis is another microporation technique that uses ultrasound energy. Ultrasound is a sound wave possessing frequencies above 20 KHz. Ultrasound can be applied either continuously or pulsed, and applied at various frequency and intensity ranges (Nanda et al., *Current Drug Delivery*, 3:233 (2006)).

Another microporation technique involves the use of a microneedle array. The array of microneedles when applied to a skin region on a subject pierce the stratum corneum and do not penetrate to a depth that significantly stimulates nerves or punctures capillaries. The patient, thus, feels no or minimal discomfort or pain upon application of the microneedle array for generation of micropores through which the calcimimetic agent is delivered.

Microneedle arrays comprised of hollow or solid microneedles are contemplated, where the calcimimetic agent can be coated on the external surface of the needles or dispensed from the interior of hollow needles. Examples of microneedle arrays are described, for example, in Nanda et al., *Current Drug Delivery*, 3:233 (2006) and Meidan et al. *American J. Therapeutics*, 11:312 (2004). First generation microneedle arrays were comprised of solid, silicon microneedles that were externally coated with a therapeutic agent. When the microarray of needles was pressed against the skin and removed after about 10 seconds, the permeation of the agent on the needles into the body was readily achieved. Second generation microneedle arrays were comprised of microneedles of solid or hollow silicon, polycarbonate, titanium or other suitable polymer and coated or filled with a solution of the therapeutic compound. Newer generations of microneedle arrays are prepared from biodegradable polymers, where the tips of the needles coated with a therapeutic agent remain in the stratum corneum and slowly dissolve.

The microneedles can be constructed from a variety of materials, including metals, ceramics, semiconductors, organics, polymers, and composites. Exemplary materials of construction include pharmaceutical grade stainless steel, gold, titanium, nickel, iron, tin, chromium, copper, palladium, platinum, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with poly(ethylene glycol), polyanhydrides, poly(ortho)esters, polyurethanes, poly(butyric acid), poly(valeric acid), and poly(lactide-co-caprolactone). Representative non-biodegradable polymers include polycarbonate, polyester, and polyacrylamides.

The microneedles can have straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips. A hollow microneedle that has a substantially uniform diameter, but which does not taper to a point, is referred to herein as a "microtube." As used herein, the term "microneedle" includes both microtubes and tapered needles unless otherwise indicated.

Electroporation is another technique for creating micropores in the skin. This approach uses the application of microsecond or millisecond long high-voltage electrical pulses to created transient, permeable pores within the stratum corneum.

Other microporation techniques include use of radio waves to create microchannels in the skin. Thermal ablation is yet another approach to achieve delivery of larger molecular weight compounds transdermally.

Applicants have discovered that low doses of calcimimetic agents may be therapeutically administered over an extended period of time to treat SHPT. This markedly differs from current dose requirements of other calcimimetics (e.g., cinacalcet hydrochloride).

Transdermal delivery of the compounds described herein was demonstrated in the studies described in Examples 9-10. In a first study, the compound Ac-crrrrrr-NH$_2$ (SEQ ID NO:6) was administered transdermally to rats in which a small area of the skin was microporated by 5 passes of a 1.0 mm derma roller under moderate pressure. A solution of either Ac-crrrrrr-NH$_2$ (SEQ ID NO: 6) or saline was placed on the microporated area of skin. Blood draws were taken over a 4 hour period and plasma was analyzed for PTH levels by ELISA. The results are shown in FIG. 11, where the plasma PTH is shown as a percent of pre-dose baseline for the saline treated animal (diamonds) and the two animals treated with the test compound (squares, triangles). These data indicate that the compound Ac-crrrrrr-NH$_2$ (SEQ ID NO: 6) can be delivered systemically in sufficient quantities by transdermal route (in this case, micropore-facilitated transdermal delivery) using a derma roller to effectively and significantly reduce PTH levels from baseline for the ~4 hours that were studies. It should be noted that Ac-crrrrrr-NH$_2$ (SEQ ID NO: 6) has been shown to effectively reduce PTH levels from baseline in the 1K1C rat model of acute renal insufficiency when administered by short IV infusion as well as in normal rats (data not shown).

Figure 12:
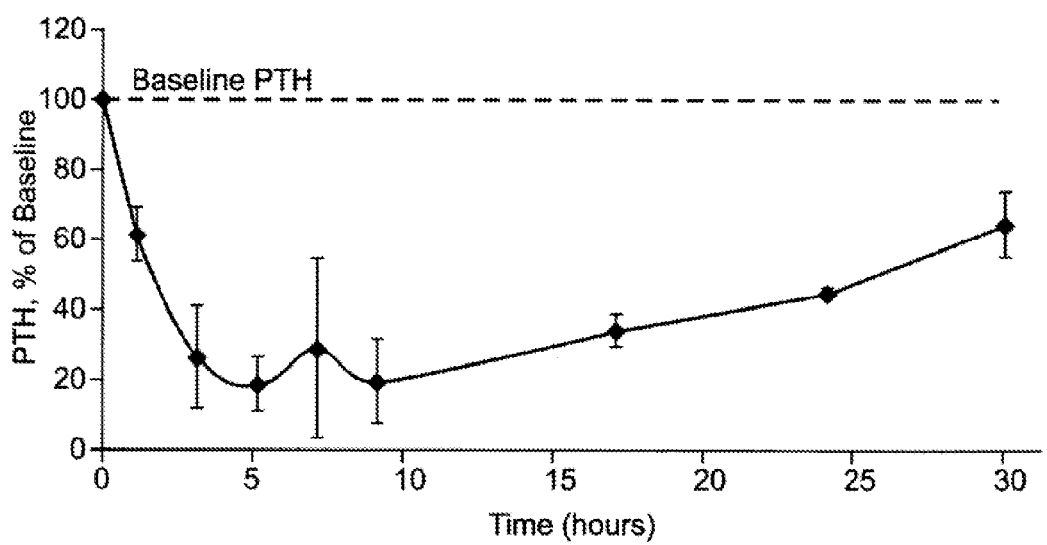
FIG. 12 is a graph of parathyroid hormone level, as percent of the baseline pre-dose value, as a function of time, in hours, in rats treated via micropore-facilitated transdermal delivery of Ac-c(C)arrrar-NH$_2$ (SEQ ID NO:3)

In another study, described in Example 10, the compound Ac-c(C)arrrar-NH$_2$ (SEQ ID NO:3) was administered micropore-facilitated transdermal delivery to normal rats using a transdermal patch. A transdermal patch system containing 10% solution (by weight) of Ac-c(C)arrrar-NH$_2$ (SEQ ID NO:3) in saline was placed over the microporated area and left in place for ~30 hours. Blood draws were taken from the rats periodically over the 30 hours and plasma samples were analyzed for PTH levels by ELISA. The results are shown in FIG. 12. Surprisingly, these data demonstrate that micropore-facilitated transdermal delivery can achieve sufficient sustained delivery of Ac-c(C)arrrar-NH$_2$ (SEQ ID NO:3) to produced a significant and extended reduction in PTH for >30 hours in rats with normal renal function. These data demonstrate that microporation facilitated transdermal delivery of the conjugate Ac-c(C)arrrar-NH$_2$ (SEQ ID NO:3) using a patch can achieve sufficient blood exposure of the peptide over the course of treatment to produce a significant and sustained reduction in PTH from baseline for >30 hrs. These data demonstrate that transdermal patch delivery on a daily basis or longer would enable treatment of both dialysis and non-hemodialysis patients in need of treatment. For example, CKD (stage 4), primary hyperparathyroidism and secondary hyperparathyroidism (SHPT) in renal transplant patients who are not typically treated with IV drugs, but could be readily treated by a daily transdermal patch via microporation facilitated transdermal delivery.

Another study was conducted to further evaluate the route of administration of the compounds. As described in Example 11, the compound Ac-c(C)arrrar-NH$_2$ (SEQ ID NO:3) was administered by very low dose IV infusion to normal rats and to rats with renal insufficiency to identify the lowest dose needed to be administered by infusion, transdermal patch system or other sustained delivery means to achieve significant PTH reduction. Healthy rats were intravenously infused for six hours with very low doses (1 µg/kg/hr, 3 µg/kg/hr, and 10 µg/kg/hr) of Ac-c(C)arrrar-NH$_2$ (SEQ ID NO:3). Blood samples were taken prior to dosing (pre) and at 2 hours, 4 hours, 6 hours (just prior to the end of infusion; EOI) and 8 hours (2 hrs post EOI) after the start of infusion and plasma was analyzed for PTH levels by ELISA. Surprisingly, the data shown in FIG. 13 demonstrate that infusion of very low doses of Ac-c(C)arrrar-NH$_2$ (SEQ ID NO:3) (1 µg/kg/hr (squares), 3 µg/kg/hr (circles), and 10 µg/kg/hr (triangles)) for 6 hours are effective to produce significant reduction in PTH from baseline over the course of infusion. These data indicate that low doses delivered continuously could be as effective as (or even more effective than) much larger doses delivery as a single bolus.

Figure 14A:
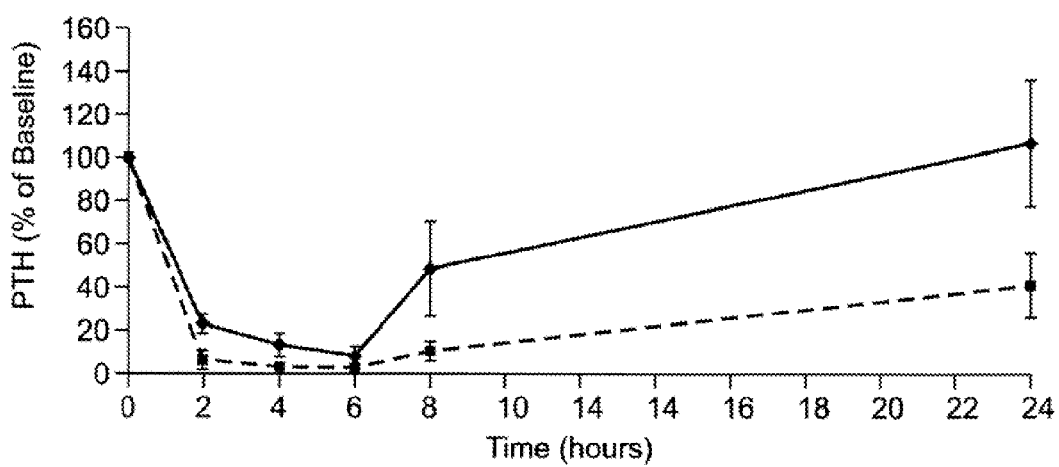
FIG. 14A shows PTH (as a percent of baseline) during and following a 6 hour IV infusion of Ac-c(C)arrrar-NH$_2$ (SEQ ID NO:3) in the 1K1C rat model of acute renal insufficiency, where rats were intravenously infused at dose rates of 30 µg/kg/hr (diamonds) and 100 µg/kg/hr (squares)
Figure 14B:
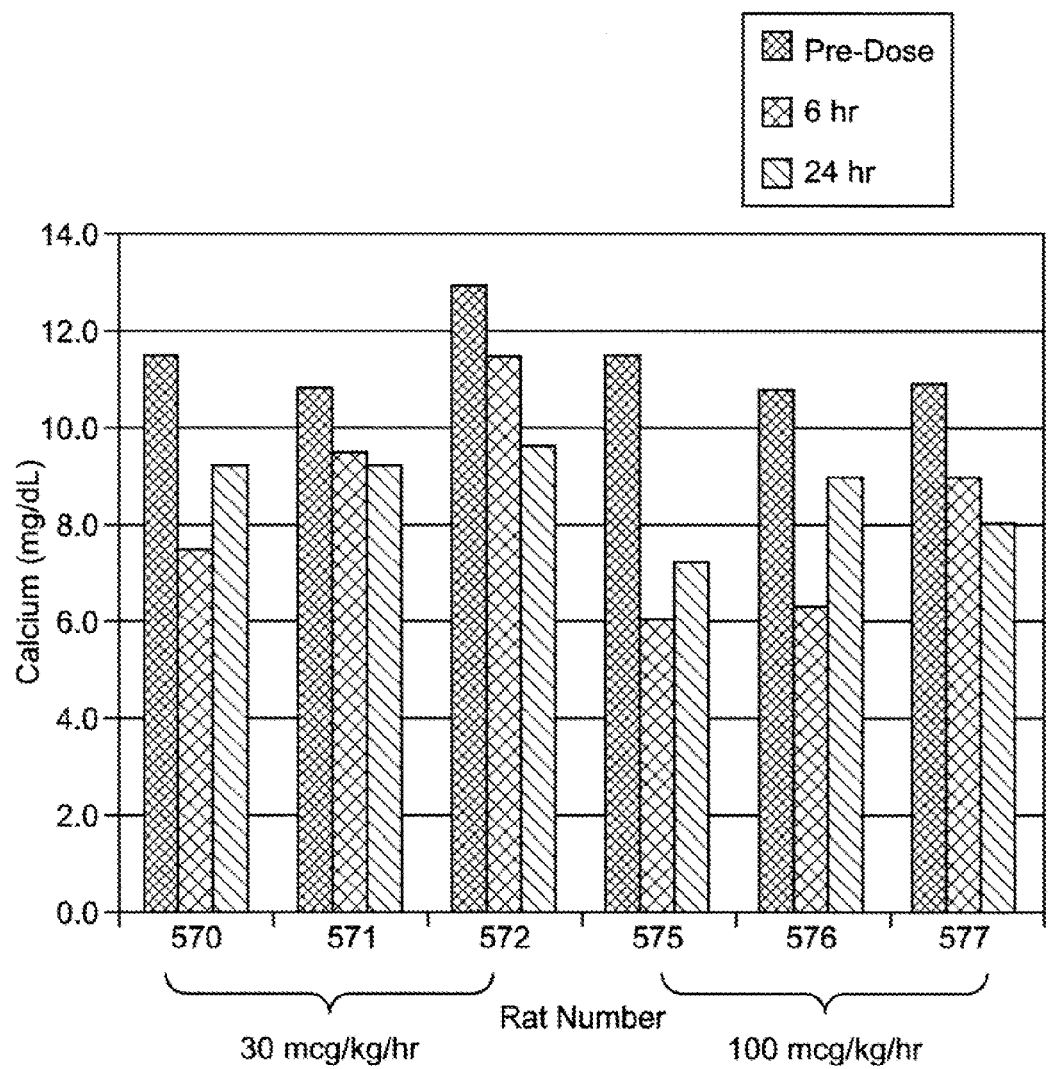
FIG. 14B is a bar graph showing serum calcium, in mg/dL, for the 1K1C model rats treated as in FIG. 14A.

The PTH lowering effect was further evaluated in the rat 1K1C model of acute renal insufficiency. 1K1C model rats were intravenously infused with low doses of Ac-c(C)arrrar-NH$_2$ (SEQ ID NO:3) (30 µg/kg/hr and 100 µg/kg/hr) for 6 hours. Blood samples were taken prior to dosing (Pre), and at 2 hours, 4 hours, 6 hours (just prior to the end of infusion; EOI), 8 hours (2 hrs post EOI) and 24 hours after the start of infusion and plasma was analyzed for PTH levels by ELISA. The data shown in FIG. 14A demonstrate that IV infusion of low doses of Ac-c(C)arrrar-NH$_2$ (SEQ ID NO:3) significantly reduce PTH from baseline levels in the 1K1C model, a model of renal insufficiency where baseline PTH levels can be seen to be from 400 to >1100 pg/mL. Surprisingly, 6 hours of low dose IV infusion (diamonds, 30 µg/kg/hr and squares, 100 µg/kg/hr) of Ac-c(C)arrrar-NH$_2$ (SEQ ID NO:3) were able to reduce PTH from baseline for ~24 hours. Consistent with this dramatic PTH reduction in the 1K1C rat model, FIG. 14B shows a bar graph plotting serum calcium data in this acute renal insufficiency, and show a corresponding reduction in serum calcium following low dose IV infusion of Ac-c(C)arrrar-NH$_2$ (SEQ ID NO:3). These data demonstrate that Ac-c(C)arrrar-NH$_2$ (SEQ ID NO:3) is a very potent calcimimetic compound that is able to reduce PTH and calcium following infusion or delivery of low doses (for example by transdermal delivery) over the course of ~24 hours. These data further support the conclusion that low dose sustained delivery of a calcimimetic agent by IV infusion or by micropore-facilitated transdermal delivery could be an effective treatment for patients on a daily or less frequent basis.

Combination Therapy

As described above, the methods of use may be used alone or in combination with other approaches for the treatment of hypercalcemia and/or bone disease. Such other approaches include, but are not limited to, treatment with agents such as bisphosphonate agents, integrin blockers, hormone replacement therapy, selective estrogen receptor modulators, cathepsin K inhibitors, vitamin D therapy, vitamin D analogs, such as ZEMPLAR™ (paricalcitol), CALCIJEX® (calcitriol), ONE-ALPHA® (alfacalcidol) and HECTOROL® (doxercalciferol), anti-inflammatory agents, low dose PTH therapy (with or without estrogen), calcimimetics, phosphate binders, calcitonin, inhibitors of RANK ligand, antibodies against RANK ligand, osteoprotegrin, adensosine antagonists and ATP proton pump inhibitors.

In one embodiment, a combination therapy uses vitamin D or a vitamin D analog in combination with a calcimimetic agent. Vitamin D aids in the absorption of calcium and functions to maintain normal blood levels of calcium and phosphorous. PTH works to enhance calcium absorption in the intestine by increasing the production of 1,25-(OH)$_2$ vitamin D, the active form of vitamin D. PTH also stimulates phosphorus excretion from the kidney, and increases release from bone.

As discussed above, secondary hyperparathyroidism is characterized by an elevation in parathyroid hormone (PTH) associated with inadequate levels of active vitamin D hormone. Vitamin D or a vitamin D analog may be used to reduce elevated PTH levels in treatment of secondary hyperparathryoidism. In one embodiment, the invention includes a pharmaceutical composition comprising a calcimimetic agent and a vitamin D analog.

In one embodiment, the invention includes a pharmaceutical composition comprising a calcimimetic agent and ZEMPLAR™ (paricalcitol). Paricalcitol is a synthetic analog of calcitriol, the metabolically active form of vitamin D. The recommended initial dose of Zemplar is based on baseline intact parathyroid hormone (iPTH) levels. If the baseline iPTH level is less than or equal to 500 pg/mL, the daily dose is 1 µg and the "three times a week" dose (to be administered not more than every other day) is 2 µg. If the baseline iPTH is greater than 500 pg/mL, the daily dose is 2 µg, and the "three times a week" does (to be administered not more than every other day) is 4 µg. Thereafter, dosing must be individualized and based on serum plasma iPTH levels, with monitoring of serum calcium and serum phosphorus. Paricalcitol is described in U.S. Pat. No. 5,246,925 and U.S. Pat. No. 5,587,497.

In another embodiment, the invention includes a pharmaceutical composition comprising a calcimimetic agent and CALCIJEX® (calcitriol). Calcitriol is the metabolically active form of vitamin D. The recommended initial dosage for CALCIJEX® (oral) is 0.25μ/day. This amount may be increased by 0.25 μg/day at 4- to 8-wk intervals. Normal or only slightly reduced calcium levels may respond to dosages of 0.25 μg every other day. For patients on dialysis, the recommended initial dose for CALCIJEX® (IV) is 0.02 μg/kg (1 to 2 μg) 3 times/week, every other day. This amount may be increased by 0.5 to 1 μg, every 2 to 4 wk. Calcitriol is described in U.S. Pat. No. 6,051,567 and U.S. Pat. No. 6,265,392 and U.S. Pat. No. 6,274,169.

In one embodiment, a pharmaceutical composition comprising a calcimimetic agent and HECTOROL® (doxercalciferol) is provided. Doxercalciferol is a synthetic analog of vitamin D that undergoes metabolic activiation in vivo to form 1α,25-dihydroxyvitamin $D_2$, a naturally occurring, biologically active form of vitamin D. The recommended initial dose of HECTOROL® is 10 μg administered three times weekly at dialysis (approximately every other day). The initial dose should be adjusted, as needed, in order to lower blood iPTH into the range of 150 to 300 pg/mL. The dose may be increased at 8-week intervals by 2.5 μg if iPTH is not lowered by 50% and fails to reach target range. The maximum recommended dose of HECTOROL is 20 μg administered three times a week at dialysis for a total of 60 μg per week. Doxercalciferol is described in U.S. Pat. No. 5,602,116 and U.S. Pat. No. 5,861,386 and U.S. Pat. No. 5,869,473 and U.S. Pat. No. 6,903,083.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

A combination treatment of the present invention as defined herein may be achieved by way of the simultaneous, sequential or separate administration of the individual components of said treatment.

The compounds or pharmaceutically acceptable compositions thereof may also be incorporated into compositions for coating implantable medical devices, bio-erodible polymers, implantable pump, and suppositories. Accordingly, in another aspect, a composition for coating an implantable device comprising a described compound as described generally above is contemplated, and a carrier suitable for coating the implantable device. In still another aspect, included is an implantable device coated with a composition comprising a compound as described generally above, and a carrier suitable for coating said implantable device.

Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Potential Clinical Markers for Determining Treatment Efficacy

Determination of the effectiveness of a described method of treatment may be determined by a variety of methods.

Normal levels of serum calcium are in the range of 8.8 mg/dL to 10.4 mg/dL (2.2 mmol/L to 2.6 mmol/L). In certain cases, the efficacy of treatment may be determined by measurement of serum and urinary markers related to calcium, including but not limited to, total and ionized serum calcium, albumin, plasma PTH, PTHrP, phosphate, vitamin D, and magnesium.

In other cases, efficacy may be determined by measurement of bone mineral density (BMD), or by measurement of biochemical markers for bone formation and/or bone resorption in serum or urine. Potential bone formation markers include, but are not limited to, total alkaline phosphatase, bone alkaline phosphatase, osteocalcin, under-carboxylated osteocalcin, C-terminal procollagen type I propeptide, and N-terminal procollagen type I propeptide. Potential bone resorption markers include, but are not limited, hydroxyproline, hydroxylysine, glycosyl-galactosyl hydroxylysine, galactosyl hydroxylysine, pyridinoline, deoxypyridinoline, N-terminal crosslinking telopeptide of type I collagen, C-terminal crosslinking telopeptide of type I collagen, C-terminal crosslinking telopeptide of type I collagen generated by MMPs, bone sialoprotein, acid phosphatase and tartrate-resistant acid phosphatase.

In other cases, efficacy may be determined by the percent reduction in PTH relative to a pre-dosing (baseline) level and/or by achieving a desirable PTH level as generally accepted as being beneficial to patients (for example, guidelines established by the National Kidney Foundation). Still in other cases, efficacy may be determined by measurement of the reduction in parathyroid gland hyperplasia associated with a hyperparathyroidism disease.

It is expected that when a described method of treatment is administered to a subject in need thereof, the method of treatment will produce an effect, as measured by, for example, one or more of: total serum calcium, ionized serum calcium, total blood calcium, ionized blood calcium, albumin, plasma PTH, blood PTH, PTHrP, phosphate, vitamin D, magnesium, bone mineral density (BMD), total alkaline phosphatase, bone alkaline phosphatase, osteocalcin, under carboxylated osteocalcin, C-terminal procollagen type I propeptide, N-terminal procollagen type I propeptide, hydroxyproline, hydroxylysine, glycosyl-galactosyl hydroxylysine, galactosyl hydroxylysine, pyridinoline, deoxypyridinoline, N-terminal crosslinking telopeptide of type I collagen, C-terminal crosslinking telopeptide of type I collagen, C-terminal crosslinking telopeptide of type I collagen generated by MMPs, bone sialoprotein, acid phosphatase and tartrate-resistant acid phosphatase. Effects include prophylactic treatment as well as treatment of existing disease.

A biologically effective molecule may be operably linked to a described peptide with a covalent bond or a non-covalent interaction. In specific embodiments, the operably linked biologically effective molecules can alter the pharmacokinetics of the described compounds by virtue of conferring properties to the compound as part of a linked molecule. Some of the properties that the biologically effective molecules can confer on the described compounds include, but are not limited to: delivery of a compound to a discrete location within the body; concentrating the activity of a compound at a desired location in the body and reducing its effects elsewhere; reducing side effects of treatment with a compound; changing the permeability of a compound; changing the bioavailability or the rate of delivery to the body of a compound; changing the length of the effect of treatment with a compound; altering the in vitro chemical stability of the compound; altering the in vivo stability of the compound, half-life, clearance, absorption, distribution and/or excretion; altering the rate of the onset and the decay of the effects of a compound; providing a permissive action by allowing a compound to have an effect.

In a further aspect, the described compound may be conjugated to polyethylene glycol (PEG). The selected PEG may be of any convenient molecular weight, and may be linear or branched, and may be optionally conjugated through a linker. The average molecular weight of PEG will preferably range from about 2 kiloDalton (kDa) to about 100 kDa, more preferably from about 5 kDa to about 40 kDa. Alternatively, the PEG moiety used can be 2, 3, 4, 5, 6, 7, 8, 9, 10, 11, 12, 13, 14, 15, 16, 17, 18, 19, or 20 kDa.

The described compounds may be conjugated to PEG through a suitable amino acid residue located at any position on the compounds. The described compounds may optionally contain an additional amino acid residue to which PEG is conjugated, including for example, an additional amine-containing residue, such as lysine.

PEGylated peptides are known in the art to increase serum half-life of conjugated peptide. A variety of methods are known in the art for the formation of PEGylated peptides. For example, the PEG moiety can be linked to the amino terminus, the carboxy terminus or through a side chain of the claimed peptide, optionally through the presence of a linking group. In other embodiments, the PEG moiety may be linked to the sulfur of a thiol-containing amino acid, such as cysteine, or may be coupled to the sidechain of an amine-containing amino acid, such as lysine.

The PEG groups will generally be attached to the described compound by acylation or alkylation through a reactive group on the PEG moiety (e.g., an aldehyde, amine, oxime, hydrazine thiol, ester, or carboxylic acid group) to a reactive group on the described compound (e.g., an aldehyde, amine, oxime, hydrazine, ester, acid or thiol group), which may be located at the amino terminus, carboxy terminus, or a sidechain position of the described compound. One approach for preparation of PEGylation of synthetic peptides consists of combining through a conjugate linkage in solution, a peptide and a PEG moiety, each bearing a functional group that is mutually reactive towards the other. Peptides can be easily prepared using conventional solution or solid phase synthesis techniques. Conjugation of the peptide and PEG is typically done in aqueous phase and may be monitored by reverse phase HPLC. The PEGylated peptides can be readily purified and characterized, using standard techniques known to one of skill in the art.

One or more individual subunits of the described compounds may also be modified with various derivatizing agents known to react with specific side chains or terminal residues. For example, lysinyl residues and amino terminal residues may be reacted with succinic anhydride or other similar carboxylic acid anhydrides which reverses the charge on the lysinyl or amino residue. Other suitable reagents include, e.g., imidoesters such as methyl picolinimidate; pyridoxal; pyridoxal phosphate; chloroborohydride; trinitrobenzenesulfonic acid; O-methylisourea; 2,4,-pentanedione; and transaminase-catalyzed reaction with glyoxalate. Arginyl residues may be modified by reaction with conventional agents such as phenylglyoxal, 2,3-butanedione, 1,2-cyclohexanedione, and ninhydrin.

In addition, the described compounds may be modified to include non-cationic residues that provide immunogenic residues useful for the development of antibodies for bioanalytical ELISA measurements, as well as to evaluate immunogenicity. For example, the described compounds may be modified by incorporation of tyrosine and/or glycine residues. Specific modifications of tyrosyl residues are of particular interest for introducing spectral labels into tyrosyl residues. Non-limiting examples include reaction with aromatic diazonium compounds or tetranitromethane. Most commonly, N-acetylimidazole and tetranitromethane are used to form O-acetyl tyrosyl and 3-nitro derivatives, respectively.

Kits Comprising the Disclosed Compounds

The invention also provides kits for carrying out the therapeutic regimens of the invention. Such kits comprise therapeutically effective amounts of the described compounds having activity as a CaSR modulator, in pharmaceutically acceptable form, alone or in combination with other agents, in pharmaceutically acceptable form. Preferred pharmaceutical forms include the described compounds in combination with sterile saline, dextrose solution, buffered solution, sterile water, or other pharmaceutically acceptable sterile fluid. Alternatively the composition may include an antimicrobial or bacteriostatic agent. Alternatively, the composition may be lyophilized or desiccated. In this instance, the kit may further comprise a pharmaceutically acceptable solution, preferably sterile, to form a solution for injection purposes. In another embodiment, the kit may further comprise a needle or syringe, preferably packaged in sterile form, for injecting the composition. In other embodiments, the kit further comprises an instruction means for administering the composition to a subject. The instruction means can be a written insert, an audiotape, an audiovisual tape, or any other means of instructing the administration of the composition to a subject.

In one embodiment, the kit comprises (i) a first container containing a described compound having activity as a CaSR modulator; and (ii) instruction means for use. In another embodiment the kit comprises (i) a first container containing a compound as described herein, and (ii) a second container containing a pharmaceutically acceptable vehicle for dilution or reconstitution.

In another embodiment, the kit comprises (i) a first container containing a described compound having activity as a CaSR modulator; (ii) a second container containing an anticalcemic agent; and (iii) instruction means for use.

In one embodiment, the anticalcemic agent is and agent selected from the group consisting of bisphosphonate agents, hormone replacement therapeutic agents, vitamin D therapy, vitamin D analogs, such as ZEMPLAR™ (paricalcitol); CALCIJEX® (calcitriol), ONE-ALPHA® (alfacalcidol) and HECTOROL® (doxercalciferol), low dose PTH (with or without estrogen), and calcitonin.

In related aspects, the invention provides articles of manufacture that comprise the contents of the kits described above. For instance, the invention provides an article of manufacture comprising an effective amount of a described peptide, alone or in combination with other agents, and instruction means indicating use for treating diseases described herein.

EXAMPLES

The following examples are offered to illustrate but not to limit the compounds and methods described herein. Various modifications may be made by the skilled person without departing from the true spirit and scope of the subject matter described herein.

Example 1

Cationic Compounds with PTH Lowering Activity

A. Model of Renal Insufficiency

A rat model of acute renal insufficiency (also referred to as the 1K1C model) was developed to simulate the pathology of SHPT associated with end stage renal disease. The model exhibits pathological characteristics of hyper parathyroidsm associated with a lack of renal function, specifically the significant elevation of plasma PTH and reduction in serum calcium. The development of this model allowed for the further characterization of described compounds in the context of a subject with renal dysfunction and elevated PTH. Typical baseline PTH levels in this model averaged ~450 pg/mL.

The 1K1C model of acute renal insufficiency involves the removal of one kidney followed by exposure of the remaining kidney to 45 minutes of ischemia and 48 hours of reperfusion. The ensuing ischemia/reperfusion (I/R) damage to the remaining kidney results in significant necrosis and renal failure. Serum creatinine levels were elevated for over 24-48 hours following I/R insult (data not shown). Also due to the resulting renal dysfunction, total PTH levels are dramatically increased from the pre-I/R injury levels of ~100 pg/mL. By 48 hours post-I/R, plasma PTH levels were elevated to ~450 pg/mL (~5 fold increase) and in some instances reach as high as ~1200 pg/mL. This reproducible increase in serum creatinine and PTH provided a robust model that mimics the physiology seen ESRD patients.

Cinacalcet hydrochloride (SENSIPAR®), an approved calcimimetic agent that is used to lower PTH for the treatment of SHPT, was tested in the 1K1C model of acute renal insufficiency. Oral administration of cinacalcet at 30 mg/kg significantly lowered PTH by approximately 50% for up to 6 hours. This result is consistent with the published preclinical data for cinacalcet (Nemeth et al., *J. Pharmacol. Exp. Ther.*, 308(2):627-35 (2004)) and validates that the 1K1C model of acute renal insufficiency is an appropriate model for evaluating the activity of calcimimetics for this indication.

The protocol used in this study is as follows. Male Sprague Dawley rats were purchased from Charles River Laboratories (Hollister, Calif.; requested purchase weight 250-275 g). For studies with test articles, animals were pre-cannulated in the femoral and jugular veins for drug administration and blood draws, respectively. Animals were maintained in a temperature-controlled environment with a constant 12 hours light/12 hours dark cycle and free access to food and water at all times. All experimental procedures with animals were performed according to IACUC guidelines.

General anesthesia was induced and maintained by intraperitoneal (IP) injection of sodium pentobarbital (5.2%, 0.4 mL/rat). For animals that received 45 minutes of renal ischemia an additional IP injection of sodium pentobarbital (5.2%, 0.1 mL/rat) was given to maintain the anesthetic plane. Blood sampling for PTH measurements following administration of compounds in normal rats was done under continuous isoflurane anesthesia.

A clean, aseptic technique was used for the entire procedure. After rats were anesthetized, the abdomen was shaved with electric clippers prior to the operation and the skin cleaned with 70% alcohol solution.

For model development studies, the left femoral vein was cannulated with a PE-10 tube for blood drawing. Both kidneys were exposed via a laparotomy. A right nephrectomy was performed after the right renal pedicle and ureter were ligated with double 2-0 silk sutures. After confirmation of non-bleeding in the right pedicle, the left renal artery was carefully dissected and clamped with a micro vascular clip to induce left renal global ischemia. Renal ischemia was confirmed by observation of a global white-grey color change (blanching). The abdominal incision was temporarily covered with gauze to help maintain the temperature of the abdominal organs. After 45 minutes, the designated period of ischemia, the clip was removed and left renal artery flow was considered restored upon observation of a global restoration of red color. The abdominal incision was closed in layers with 2-0 silk sutures. The animal was then recovered from anesthesia. Physiological parameters including body temperature (36-37.5° C.) and body weight were measured throughout the procedure. Body temperature was monitored and maintained using a heat pad rectal probe feedback system.

Approximately 48 hours after the 1K1C surgery (I/R injury), animals were dosed with various compounds to measure effects on plasma PTH and calcium. In most cases, test articles were administered by IV infusion (infusion time 5, 10 or 30 minutes) although in some studies compounds were administered by IV bolus or subcutaneous (SC) bolus injection. For drug administration and blood draws, animals were anesthetized with isoflurane.

Blood samples were collected periodically throughout the course of the study. Serum samples were analyzed for of calcium levels and plasma samples were analyzed for PTH. Due to the range of baseline PTH values for individual rats, all data are normalized to pre-dosing (baseline) levels. Serum creatinine was measured using a commercially available kit from BioAssay Systems (Hayward, Ca), catalog #DICT-500. Analyses were performed according to the manufacturer's instructions.

B. Testing Compounds in Renal Insufficiency Model

Compounds with the following sequences were prepared for testing in the renal insufficiency model: Ac-crrrr-NH$_2$ (SEQ ID NO:4), n=4, Ac-crrrrr-NH$_2$ (SEQ ID NO:5), n=4, Ac-crrrrrr-NH$_2$ (SEQ ID NO:6), n=7, Ac-crrrrrrr-NH$_2$ (SEQ ID NO:7), n=4, and saline control, n=2. The peptides were administered to animals at a dose of 3 mg/kg by a 30-minute IV infusion. Prior to dosing a blood sample was drawn to determine baseline, pre-dosing PTH plasma concentration. Results are shown in FIG. 1 as follows: Ac-crrrr-NH$_2$ (SEQ ID NO:4, diamonds), Ac-crrrrr-NH$_2$ (SEQ ID NO:5, squares), Ac-crrrrrr-NH$_2$ (SEQ ID NO:6, triangles), and Ac-crrrrrrr-NH$_2$ (SEQ ID NO:7, open squares).

Example 2

In Vitro Cell Assay in HEK-293 Expressing the Human Calcium-Sensing Receptor

Human embryonic kidney (HEK) 293T cells were seeded into a T25 flask at 2 million cells per flask and allowed to incubate at 37° C. in 5% CO$_2$ overnight. The day after, these cells were transfected with human CaSR receptor using lipofectamine 2000 transfection reagent 24 hrs post transfection, cells were seeded in 384 well plates at 8,000 cells/well. Assays were carried out 48 hours after the transfection. In some cases, EC$_{50}$ values were determined by measuring inositol monophosphate production in the HEK293 cells, stably transfected with the human calcium-sensing receptor (see Table 1).

The cell culture medium was aspirated from the wells and replaced with 28 µL of 1× stimulation buffer (Hepes 10 mM, CaCl2 1 mM, MgCl2 0.5 mM, KCl 4.2 mM, NaCl 146 mM, glucose 5.5 mM, LiCl 50 mM pH 7.4). Cells were incubated with compounds at various concentrations (1 mM or 300 µM as the highest and further ½ log serial dilutions) at 37° C. for 1.5 hrs before reaction termination. IP$_1$ production was determined in cells using the Cisbio IP-One Tb kit (621 PAPEC) and according to manufacturer instructions. In brief, incubation with the compound was terminated by sequentially adding D2 labeled-$IP_1$ and cryptate-labeled anti-$IP_1$ in lysis buffer and further incubating at room temperature for 60 minutes. Plates were read at 620 nm and 668 nm with 314 nm excitation. Non-transfected 293 cells were used as negative control.

The ratio of fluorescence at 668 nm and 620 nm was determined. $IP_1$ concentrations were calculated from standard curves (generated with Graph Pad Prism ver. 4) using known concentrations of $IP_1$ standards. $EC_{50}$s were calculated based on the values of the fluorescent ratio OD(668 nm)/(OD620 nm) using non-linear regression curve fitting in Prism software.

Peptides and conjugates were prepared by solid-phase chemistry at 0.25 mmol scale on an ABI automated synthesizer. Sequential coupling of Fmoc-amino acids (4 eq, Anaspec) to Rink-amide resin (NovaBiochem) was accomplished using HBTU/DIEA activation. The assembled peptide was cleaved with a TFA cocktail (phenol (5%), triisopropylsilane (2.5%) and water (2.5%); 10 mL per gram of resin) and isolated by precipitation with diethyl ether. After purification by $C_{18}$ HPLC the final product was isolated in the TFA salt form by lyophilization of appropriate fractions, and characterized by HPLC (>95% purity) and LC-MS (confirmed MW).

Example 3

In Vivo Administration of Compounds with Cationic Subunits

The peptides were administered intravenously at a dose of 0.5 mg/kg into isoflurane-anesthetized normal Sprague Dawley rats. A control group of rats was treated with saline. Blood was drawn prior to dosing and every hour for 4 hours. Rats were maintained under isoflurane anesthesia for the entire study. The concentration of PTH in the plasma was measured by ELISA, detecting the bioactive intact PTH 1-84 (Immutopics International catalog number 60-2700), and the cumulative area under the curve for AUC was calculated for the data points inclusive of 1-4 hours. Percent PTH reduction was calculated according to the following formula: $AUC_{cmpd\ treated}/AUC_{saline\ control}*100$.

Example 4

Structure-Activity Relationship Studies: In Vivo Activity

Figure 2B:
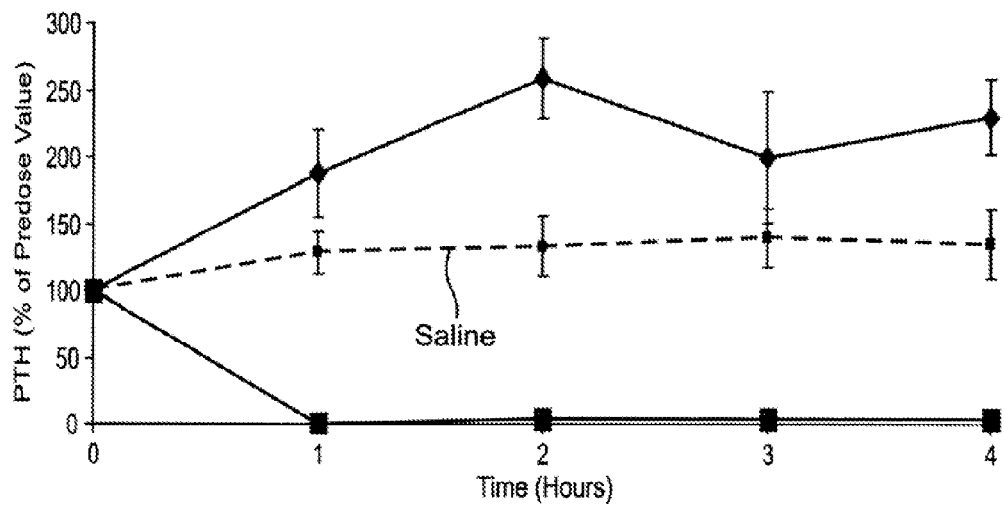
FIG. 2B shows the reduction in PTH concentration upon in vivo administration of peptides identified as SEQ ID NO:26 (Ac-carrrar-NH$_2$) (squares) and as SEQ ID NO:29 (Ac-arrrar-NH$_2$) (diamonds), where the peptides were administered as an IV bolus to normal Sprague Dawley rats at doses of 9 mg/kg for SEQ ID NO:29 and at 0.5 mg/kg for SEQ ID NO:26. An intravenous (IV) bolus of saline was used as a control (dashed line). Plasma PTH levels were assessed prior to dosing and 1, 2, 3 and 4 hours after dosing. Results are presented as group average±standard deviation (SD), and PTH is shown as percent of the baseline pre-dose value.

The peptides tested identified herein as SEQ ID NO: 26 (Ac-carrrar-$NH_2$) and as SEQ ID NO:29 (Ac-arrrar-$NH_2$) were tested in vitro using the HEK293 CaSR transfected cells, according to the procedure in Example 2. The peptides were also tested in vivo, by administering as an IV bolus to normal Sprague Dawley rats at doses of 9 mg/kg for SEQ ID NO:29 and at 0.5 mg/kg for SEQ ID NO: 26. An intravenous (IV) bolus of saline was used as a control. Plasma ($K_2$EDTA) PTH levels were assessed prior to dosing and 1, 2, 3 and 4 hours after dosing. Rats were maintained under isoflurane anesthesia for the entire study. The results are shown in FIGS. 2A-2B, presented as group average±standard deviation (SD). In FIG. 2B, PTH is shown as percent of the baseline pre-dose value.

Example 5

Structure-Activity Relationship Studies: D- and L-Amino Acid Subunits

A series of compounds having an L-amino acid residue substituted for a D-amino acid residue were prepared. The compounds were administered as an IV bolus to normal Sprague Dawley rats at a dose of 0.5 mg/kg. An intravenous (IV) bolus of saline was used as a control. Plasma ($K_2$EDTA) PTH levels were assessed prior to dosing and 1, 2, 3 and 4 hours after dosing, and the AUC was calculated as described above. Rats were maintained under isoflurane anesthesia for the entire study. The results are shown in Table 4 above.

Example 6

Structure-Activity Relationship Studies: Histamine Release

To evaluate the effect of net positive charge on the histamine release associated with a compound, peptides containing 4 to 7 cationic (arginine) residues were generated and tested for their ability to trigger histamine release in vivo. The tested peptides included (i) Ac-crrrr-$NH_2$ (SEQ ID NO:4), (ii) Ac-crrrrr-$NH_2$ (SEQ ID NO:5), (iii) Ac-crrrrrr-$NH_2$ (SEQ ID NO:6) and (iv) Ac-crrrrrrrr-$NH_2$; SEQ ID NO:41).

Male Sprague-Dawley rats were obtained (Charles River) pre-cannulated in the femoral and jugular veins for drug infusion and blood draws, respectively. All IV drug treatments were conducted under anesthetic (isoflurane). Animals were dosed by a 1-minute IV push in a total volume of 0.5 mL. Blood samples were taken at 5, 15 and 30 minutes following IV bolus to generate plasma ($K_2$EDTA) samples for histamine analysis. For 30 minute IV infusion studies, sample was taken at the end of infusion. In some case rats in the 1K1C model of acute renal ischemia were used.

An equal volume of saline was injected following each blood draw to replace lost volume. Approximately 0.2 mL of blood was withdrawn at each time point using pre-coated EDTA syringes to facilitate serum collection.

Histamine ELISAs were performed on diluted plasma using the Histamine Enzyme Immunoassay (EIA) kit (Cat #A05890, SPI-BIO, Montigny le Bretonneux, France). The Histamine EIA kit is a derivitization-amplified competitive enzyme immunoassay which detects histamine within the range of 40 pg/mL to 5,500 pg/mL. The samples were analyzed in duplicate according to the manufacturer's protocol.

Lyophilized peptides (TFA salts) were weighed and the recorded mass was adjusted for peptide content. Solutions were prepared by dissolving the material in normal saline to generate the desired peptide concentration. In some cases the molarity of peptide was adjusted to allow for inter-peptide comparison. The peptides were administered by IV bolus at an equivalent dose on a per mole basis as SEQ ID NO:41 (i.e., 0.7 μmole/rat) by a 1-minute IV bolus and plasma histamine was measured before dosing (pre-dose), 5, 15 and 30 minutes after dosing. Data are presented as group averages (n=2)±SD. Histamine release is shown as fold change from pre-dose (baseline) levels. Results are shown in FIG. 3. Data are presented as group averages (n=2)±SD.

Example 7

Structure-Activity Relationship Studies: Histamine Release

For in vitro evaluation of histamine release, isolated rat peritoneal mast cells were isolated by performing peritoneal lavage using cold HBSS+25 mM HEPES pH 7.4 containing heparin (5 u/mL). Cells were washed twice in stimulation buffer (HBSS+25 mM HEPES pH 7.4) and incubated with 10 µM of compound in stimulation buffer (HBSS+25 mM HEPES pH 7.4) for 15 minutes in a 96-well plate ($10^6$/well) at 37° C. Cell supernatant was analyzed for histamine using histamine EIA kit (Cayman #589651). Data is shown in Table 10.

For the in vivo evaluation of histamine release, compounds were dosed in isoflurane-anesthetized normal rats at 2 mg/kg by IV bolus (administered over less than one minute). Plasma histamine was measured 5 minutes after compound administration (Cayman histamine EIA #589651). Data is shown in Table 11.

The abbreviations used herein, and in particular in Tables 10-11 are summarized here.

| | |
|---|---|
| Ahx | 6-aminohexanoic acid |
| Aib | 2-aminoisobutyric acid |
| bAla | beta-alanine (3-aminopropionic acid) |
| dHcy | D-homocysteine |
| dNle | D-norleucine |
| dNva | D-norvaline |
| dPen | D-penicillamine |
| EG | ethylene glycol spacer, H2N—(CH2CH2—O)4—CH2—CO2H |
| Hcy | homocysteine |
| Mpa | 3-mercaptopropionic acid or mercaptopropionic acid |
| Nma | N-methylalanine |
| PEG | poly (ethylene glycol) |
| Sar | Sarcosine (N-methylglycine) |
| dHar | D-homoarginine |
| GS | Glutatione (conjugated) |
| DAP | 1,3-diaminopropionic acid |

Example 8

Structure-Activity Relationship Studies: In Vivo Activity

The compound Ac-c(C)arrrar-NH$_2$ (SEQ ID NO:3) was prepared for comparison with the compound Ac-carrrar-NH$_2$ (SEQ ID NO:26). In the compound Ac-c(C)arrrar-NH$_2$ (SEQ ID NO:3) the thiol-containing subunit in position $X_1$ is conjugated via a disulfide linkage to an L-Cys residue. The two compounds were administered via IV bolus to animals with the 1K1C model of acute renal insufficiency at doses of 0.3 and 0.5 mg/kg. Plasma PTH levels were assessed prior to dosing and periodically for 24 hours after dosing. Results are shown in FIG. 10, where data shown are group averages±SEM, where as a function of time, in hours, in rats with 1K1C model of acute renal insufficiency, the compound Ac-c(C)arrrar-NH$_2$ (SEQ ID NO:3) is represented by squares (0.3 mg/kg, n=5) and * symbols (0.5 mg/kg, n=6) and the compound Ac-c(Ac—C)arrrar-NH$_2$ (SEQ ID NO:141) by triangles (0.3 mg/kg, n=8) and diamonds (0.5 mg/kg, n=7).

Example 9

Micropore Facilitated Transdermal Delivery of Calcimimetic Agents

To evaluate systemic delivery of a calicimimetic agent, Ac-crrrrrr-NH$_2$ (SEQ ID NO:6) was administered to CD hairless rats transdermally using a reservoir. Ac-crrrrrr-NH$_2$ (SEQ ID NO:6) was applied as a 10% solution in saline to an approximately 1 cm$^2$ area on the back of CD® hairless rats that were microporated by 5 passes of a 1.0 mm Derma Roller under moderate pressure. A polystyrene chamber (I.D. 9.5 mm) was glued over the microporated area of skin to create a drug reservoir in which the solution of either Ac-crrrrrr-NH$_2$ (SEQ ID NO: 6) or a saline solution were applied. A 10% solution of Ac-crrrrrr-NH$_2$ (SEQ ID NO: 6) was administered in the reservoir chamber on two rats, a saline solution alone was administered in the reservoir chamber on one rat. The reservoirs were covered with tape to prevent evaporation. Blood draws were taken over a 4 hour period and plasma was analyzed for PTH levels by ELISA. The results are shown in FIG. 11.

Example 10

Sustained Delivery of Calcimimetic Agents by Micropore Facilitated Transdermal Patch To further evaluate systemic delivery of a calcimimetic agent, Ac-c(C)arrrar-NH$_2$ (SEQ ID NO:3) was administered transdermally to normal rats using a transdermal patch. Normal rats were treated with microneedle array and transdermal patch system. A small area of fur on the back of Sprague Dawley rats (~350 g) was sheared using clippers and an area of skin was microporated using a 14×14 array (~1 cm$^2$) of microneedles (~0.5 mm). A transdermal patch system containing 10% solution (by weight) of Ac-c(C) arrrar-NH$_2$ (SEQ ID NO:3) in saline was placed over the microporated area and left in place for ~30 hours. Blood draws were taken from the rats periodically over the 30 hours and plasma samples was analyzed for PTH levels by ELISA. The results are shown in FIG. 12.

Example 11

Infusion of Calcimimetic Agents

Figure 13:
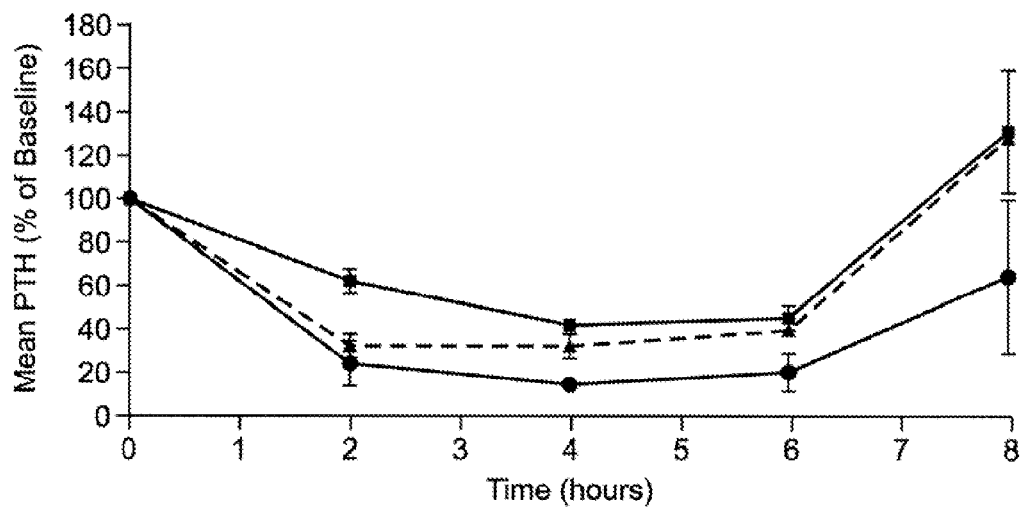
FIG. 13 is a graph of mean PTH (as percent of baseline) during and following a 6 hour IV infusion of Ac-c(C)arrrar-NH$_2$ (SEQ ID NO:3) in normal Sprague-Dawley rats, where the compound was infused at rates of 1 µg/kg/hr (squares), 3 µg/kg/hr (circles), and 10 µg/kg/hr (triangles)

To further evaluate the PTH lowering effect of the calcimimetic compound Ac-c(C)arrrar-NH$_2$ (SEQ ID NO:3) was administered by very low dose IV infusion to normal rats and rats with renal insufficiency to identify the lowest dose needed to be administered by infusion, transdermal patch system or other sustained delivery means to achieve significant PTH reduction. Normal Sprague-Dawley male rats (250-300 g) were intravenously infused for 6 hours with Ac-c(C)arrrar-NH$_2$ (SEQ ID NO: 3) at dose rates of 1 µg/kg/hr, 3 µg/kg/hr, and 10 µg/kg/hr. Blood samples were taken prior to dosing, at 2 hours, 4 hours, 6 hours (just prior to the end of infusion; EOI) and 8 hours (2 hrs post EOI) and plasma was analyzed for PTH levels by ELISA. The data are shown in FIG. 13, where rats treated with 1 µg/kg/hr (squares), 3 µg/kg/hr (diamonds), and 10 µg/kg/hr (triangles) for 6 hours were effective to produce significant reduction in PTH from baseline over the course of infusion.

A similar study was conducted in rats with the 1K1C model of acute renal insufficiency. 1K1C model rats were intravenously infused with Ac-c(C)arrrar-NH$_2$ (SEQ ID NO:

273 at dose rates of 30 µg/kg/hr and 100 µg/kg/hr for 6 hours. Blood samples were taken prior to dosing (Pre), at 2 hours, 4 hours, 6 hours (just prior to the end of infusion; EOI), 8 hours (2 hrs post EOI) and 24 hours and plasma was analyzed for PTH levels by ELISA. The data are shown in FIG. 14A (30 µg/kg/hr, diamonds, and 100 µg/kg/hr, squares) and the serum calcium for the animals is shown in FIG. 14B.

The invention claimed is:

1. A compound comprising a peptide 8 to 15 amino acids in length comprising the amino acid sequence $X_1$-$X_2$-$X_3$-$X_4$-$X_5$-$X_6$-$X_7$, wherein:
   $X_1$ is L-cysteine or D-cysteine,
   $X_2$ is D-alanine or D-arginine,
   $X_3$ is D-arginine,
   $X_4$ is D-alanine or D-arginine,
   $X_5$ is D-arginine,
   $X_6$ is D-alanine, and
   $X_7$ is D-arginine.

2. The compound of claim 1, wherein the peptide is 8 to 11 amino acids in length.

3. The compound of claim 1, wherein the peptide comprises the amino acid sequence $X_1$-$X_2$-$X_3$-$X_4$-$X_5$-$X_6$-$X_7$, wherein:
   $X_2$ is D-alanine,
   $X_3$ is D-arginine,
   $X_4$ is D-arginine,
   $X_5$ is D-arginine,
   $X_6$ is D-alanine, and
   $X_7$ is D-arginine.

4. The compound of claim 1, wherein the N-terminus of the peptide is acetylated.

5. The compound of claim 1, wherein the C-terminus of the peptide is amidated.

6. The compound of claim 1, wherein the N-terminus of the peptide is acetylated and the C-terminus of the peptide is amidated.

7. The compound of claim 1, wherein $X_1$ is conjugated to a conjugating group via a disulfide bond.

8. The compound of claim 7, wherein the conjugating group is selected from the group consisting of cysteine, homocysteine, glutathione, pegylated cysteine and a thiol-containing polypeptide.

9. The compound of claim 7, wherein the conjugating group is L-cysteine.

10. The compound of claim 7, wherein the conjugating group is D-cysteine.

11. The compound of claim 3, wherein the N-terminus of the peptide is acetylated.

12. The compound of claim 3, wherein the C-terminus of the peptide is amidated.

13. The compound of claim 3, wherein the N-terminus of the peptide is acetylated and the C-terminus of the peptide is amidated.

14. The compound of claim 3, wherein $X_1$ is conjugated to a conjugating group via a disulfide bond.

15. The compound of claim 14, wherein the conjugating group is selected from the group consisting of cysteine, homocysteine, glutathione, pegylated cysteine and a thiol-containing polypeptide.

16. The compound of claim 14, wherein the conjugating group is L-cysteine.

17. The compound of claim 14, wherein the conjugating group is D-cysteine.

18. A pharmaceutical composition comprising the compound of claim 1.

19. A pharmaceutical composition comprising the compound of claim 3.

20. A method of treating secondary hyperparathyroidism (SHPT) in a subject, comprising administering to the subject a therapeutically effective amount of the compound according to claim 1.

21. The method of claim 20, wherein the subject is suffering from chronic kidney disease.

22. The method according to claim 20, wherein the administering is intravenous.

23. A method of treating secondary hyperparathyroidism (SHPT) in a subject, comprising administering to the subject a therapeutically effective amount of the compound according to claim 3.

24. The method of claim 23, wherein the subject is suffering from chronic kidney disease.

25. The method according to claim 23, wherein the administering is intravenous.

26. The compound of claim 2, wherein the peptide comprises the amino acid sequence $X_1$-$X_2$-$X_3$-$X_4$-$X_5$-$X_6$-$X_7$, wherein:

$X_2$ is D-alanine,
$X_3$ is D-arginine,
$X_4$ is D-arginine,
$X_5$ is D-arginine,
$X_6$ is D-alanine, and
$X_7$ is D-arginine.

27. The compound of claim 1, wherein the peptide comprises the amino acid sequence $X_1$-$X_2$-$X_3$-$X_4$-$X_5$-$X_6$-$X_7$, wherein:

$X_2$ is D-arginine,
$X_3$ is D-arginine,
$X_4$ is D-alanine,
$X_5$ is D-arginine,
$X_6$ is D-alanine, and
$X_7$ is D-arginine.

28. The compound of claim 2, wherein the peptide comprises the amino acid sequence $X_1$-$X_2$-$X_3$-$X_4$-$X_5$-$X_6$-$X_7$, wherein:

$X_2$ is D-arginine,
$X_3$ is D-arginine,
$X_4$ is D-alanine,
$X_5$ is D-arginine,
$X_6$ is D-alanine, and
$X_7$ is D-arginine.

\* \* \* \* \*

UNITED STATES PATENT AND TRADEMARK OFFICE
CERTIFICATE OF CORRECTION

PATENT NO. : 9,567,370 B2
APPLICATION NO. : 14/639020
DATED : February 14, 2017
INVENTOR(S) : Felix Karim et al.

Page 1 of 1

It is certified that error appears in the above-identified patent and that said Letters Patent is hereby corrected as shown below:

In the Specification

Column 14, Line 55: change "..potency of the compound, as the peptides Ac-carrrar-NH (SEQ ID NO:26)..." to --potency of the compound, as the peptides Ac-carrrar-$NH_2$ (SEQ ID NO:26)--

Column 18, Line 34: change "...because Ac-crrrrrrrr-$NH_2$ (SEQ ID NO:6441) is expected to be taken up into cells by virtue of its cell-penetrating characteristic..." to --because Ac-crrrrrrrr-$NH_2$ (SEQ ID NO:41) is expected to be taken up into cells by virtue of its cell-penetrating characteristic--

Column 19, Line 13: change "Tested analogs included Ac-cGrrrGr-$NH_2$ (SEQ ID NO:42)..." to --Tested analogs included (i) Ac-cGrrrGr-$NH_2$ (SEQ ID NO:42)--

Column 19, Line 25: change "..D-amino acid residues (D-arginine residues), the change in..." to --D-amino acid residues (D-alanine residues), the change in--

Column 24, Line 59: change "...$NH_2$ (SEQ ID NO:273 where the L-Cys residue linked to the..." to --$NH_2$ (SEQ ID NO:3) where the L-Cys residue linked to the--

Signed and Sealed this
Second Day of July, 2019

Andrei Iancu
*Director of the United States Patent and Trademark Office*

```
                       SEQUENCE LISTING

<160> NUMBER OF SEQ ID NOS: 183

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(7)
<223> OTHER INFORMATION: Xaa = any amino acid as defined in the
      specification filed herewith

<400> SEQUENCE: 1

Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg

<400> SEQUENCE: 2

Xaa Xaa Xaa Xaa Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
```

```
<221> NAME/KEY: MOD_RES
<222> LOCATION: (7)
<223> OTHER INFORMATION: C-terminal amidation

<400> SEQUENCE: 3

Xaa Xaa Xaa Xaa Xaa Xaa Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(5)
<223> OTHER INFORMATION: Xaa = D-Arg
<220> FEATURE:
<221> NAME/KEY: MOD_RES
<222> LOCATION: (5)
<223> OTHER INFORMATION: C-terminal amidation

<400> SEQUENCE: 4

Xaa Xaa Xaa Xaa Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(6)
<223> OTHER INFORMATION: Xaa = D-Arg
<220> FEATURE:
<221> NAME/KEY: MOD_RES
<222> LOCATION: (6)
<223> OTHER INFORMATION: C-terminal amidation

<400> SEQUENCE: 5

Xaa Xaa Xaa Xaa Xaa Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
```

```
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 6

Xaa Xaa Xaa Xaa Xaa Xaa Xaa
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(8)
<223> OTHER INFORMATION: Xaa = D-Arg
<220> FEATURE:
<221> NAME/KEY: MOD_RES
<222> LOCATION: (8)
<223> OTHER INFORMATION: C-terminal amidation

<400> SEQUENCE: 7

Xaa Xaa Xaa Xaa Xaa Xaa Xaa Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(2)
<223> OTHER INFORMATION: Xaa = D-Ala
<220> FEATURE:
<221> NAME/KEY: VARIANT
<222> LOCATION: (3)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 8

Xaa Xaa Xaa Xaa Xaa Xaa Xaa
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(2)
<223> OTHER INFORMATION: Xaa = D-Arg
<220> FEATURE:
<221> NAME/KEY: VARIANT
<222> LOCATION: (3)..(3)
<223> OTHER INFORMATION: Xaa = D-Ala
<220> FEATURE:
<221> NAME/KEY: VARIANT
<222> LOCATION: (4)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 9

Xaa Xaa Xaa Xaa Xaa Xaa Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5)...(7)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 10

Xaa Xaa Xaa Xaa Xaa Xaa Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
```

```
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(4), (6)...(7)
<223> OTHER INFORMATION: Xaa = D-Arg
<220> FEATURE:
<221> NAME/KEY: VARIANT
<222> LOCATION: (5)..(5)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 11

Xaa Xaa Xaa Xaa Xaa Xaa Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(5), (7)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 12

Xaa Xaa Xaa Xaa Xaa Xaa Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(6)
<223> OTHER INFORMATION: Xaa = D-Arg
<220> FEATURE:
<221> NAME/KEY: VARIANT
<222> LOCATION: (7)..(7)
```

```
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 13

Xaa Xaa Xaa Xaa Xaa Xaa Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (6)
<223> OTHER INFORMATION: Xaa = D-Arg
<220> FEATURE:
<221> NAME/KEY: VARIANT
<222> LOCATION: (4), (7)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 14

Xaa Xaa Xaa Xaa Xaa Xaa Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4)
<223> OTHER INFORMATION: Xaa = D-Ala
<220> FEATURE:
<221> NAME/KEY: VARIANT
<222> LOCATION: (3), (5) (6), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 15

Xaa Xaa Xaa Xaa Xaa Xaa Xaa
1               5

<210> SEQ ID NO 16
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (5)
<223> OTHER INFORMATION: Xaa = D-Ala
<220> FEATURE:
<221> NAME/KEY: VARIANT
<222> LOCATION: (3), (4), (6), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 16

Xaa Xaa Xaa Xaa Xaa Xaa Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (6), (7)
<223> OTHER INFORMATION: Xaa = D-Arg
<220> FEATURE:
<221> NAME/KEY: VARIANT
<222> LOCATION: (4), (5)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 17

Xaa Xaa Xaa Xaa Xaa Xaa Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
```

```
-continued

<220> FEATURE:
<221> NAME/KEY: VARIANT
<222> LOCATION: (2), (4), (6), (7)
<223> OTHER INFORMATION: Xaa = D-Arg
<220> FEATURE:
<221> NAME/KEY: VARIANT
<222> LOCATION: (3), (5)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 18

Xaa Xaa Xaa Xaa Xaa Xaa Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (7)
<223> OTHER INFORMATION: Xaa = D-Ala
<220> FEATURE:
<221> NAME/KEY: VARIANT
<222> LOCATION: (3)...(6)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 19

Xaa Xaa Xaa Xaa Xaa Xaa Xaa
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (5), (6)
<223> OTHER INFORMATION: Xaa = D-Arg
<220> FEATURE:
<221> NAME/KEY: VARIANT
<222> LOCATION: (3), (7)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation
```

```
<400> SEQUENCE: 20

Xaa Xaa Xaa Xaa Xaa Xaa Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (4), (7)
<223> OTHER INFORMATION: Xaa = D-Arg
<220> FEATURE:
<221> NAME/KEY: VARIANT
<222> LOCATION: (5), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 21

Xaa Xaa Xaa Xaa Xaa Xaa Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(3)
<223> OTHER INFORMATION: Xaa = D-Ala
<220> FEATURE:
<221> NAME/KEY: VARIANT
<222> LOCATION: (4)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 22

Xaa Xaa Xaa Xaa Xaa Xaa Xaa
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (5), (7)
<223> OTHER INFORMATION: Xaa = D-Arg
<220> FEATURE:
<221> NAME/KEY: VARIANT
<222> LOCATION: (3), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 23

Xaa Xaa Xaa Xaa Xaa Xaa Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (5), (6), (7)
<223> OTHER INFORMATION: Xaa = D-Arg
<220> FEATURE:
<221> NAME/KEY: VARIANT
<222> LOCATION: (3), (4)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 24

Xaa Xaa Xaa Xaa Xaa Xaa Xaa
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
```

```
<222> LOCATION: (4), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 25

Xaa Xaa Xaa Xaa Xaa Xaa Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 26

Xaa Xaa Xaa Xaa Xaa Xaa Xaa
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 27
```

```
Xaa Xaa Xaa Xaa Xaa Xaa Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 28

Xaa Xaa Xaa Xaa Xaa Xaa Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1), (5)
<223> OTHER INFORMATION: Xaa = D-Ala
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (4), (6)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 29

Xaa Xaa Xaa Xaa Xaa Xaa
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
```

```
<223> OTHER INFORMATION: Xaa = bAla
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Cys
<220> FEATURE:
<221> NAME/KEY: VARIANT
<222> LOCATION: (3)...(8)
<223> OTHER INFORMATION: Xaa = D-Arg
<220> FEATURE:
<221> NAME/KEY: MOD_RES
<222> LOCATION: (8)
<223> OTHER INFORMATION: C-terminal amidation

<400> SEQUENCE: 30

Xaa Xaa Xaa Xaa Xaa Xaa Xaa Xaa
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = 3-Mercaptopropionic acid
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 31

Xaa Xaa Xaa Xaa Xaa Xaa Xaa
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Homocysteine
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 32

Xaa Xaa Xaa Xaa Xaa Xaa Xaa
1               5

<210> SEQ ID NO 33
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-penicillamine
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 33

Xaa Xaa Xaa Xaa Xaa Xaa Xaa
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys interchain disulfide bond
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 34

Xaa Xaa Xaa Xaa Xaa Xaa Xaa
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
```

```
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 35

Cys Xaa Xaa Xaa Xaa Xaa Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 36

Xaa Xaa Arg Xaa Xaa Xaa Xaa
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
```

```
<221> NAME/KEY: VARIANT
<222> LOCATION: (3), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 37

Xaa Xaa Xaa Arg Xaa Xaa Xaa
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 38

Xaa Xaa Xaa Xaa Arg Xaa Xaa
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
```

```
<222> LOCATION: (7)
<223> OTHER INFORMATION: C-terminal amidation

<400> SEQUENCE: 39

Xaa Xaa Xaa Xaa Xaa Ala Xaa
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (6)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 40

Xaa Xaa Xaa Xaa Xaa Xaa Arg
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(9)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 41

Xaa Xaa Xaa Xaa Xaa Xaa Xaa Xaa Xaa
1               5

<210> SEQ ID NO 42
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 42

Xaa Gly Xaa Xaa Xaa Gly Xaa
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 43

Xaa Ala Xaa Xaa Xaa Ala Xaa
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (4)
<223> OTHER INFORMATION: Xaa = D-Arg
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 44
```

```
Cys Xaa Arg Xaa Arg Xaa Arg
1               5
```

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

```
Cys His Asp Ala Pro Ile Gly Tyr Asp
1               5
```

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

```
Cys Pro Asp Tyr His Asp Ala Gly Ile
1               5
```

<210> SEQ ID NO 47
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: MOD_RES
<222> LOCATION: (12)..(12)
<223> OTHER INFORMATION: C-terminal amidation

<400> SEQUENCE: 47

```
Cys Tyr Gly Arg Lys Lys Arg Arg Gln Arg Arg
1               5                   10
```

<210> SEQ ID NO 48
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: MOD_RES
<222> LOCATION: (11)..(11)
<223> OTHER INFORMATION: C-terminal amidation

<400> SEQUENCE: 48

```
Tyr Gly Arg Lys Lys Arg Arg Gln Arg Arg
1               5                   10
```

<210> SEQ ID NO 49
<211> LENGTH: 8
<212> TYPE: PRT
<213> ORGANISM: Artificial Sequence
<220> FEATURE:
<223> OTHER INFORMATION: Synthetic peptide
<220> FEATURE:

```
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (5)
<223> OTHER INFORMATION: Xaa = D-Ala
<220> FEATURE:
<221> NAME/KEY: VARIANT
<222> LOCATION: (3), (6), (7), (8)
<223> OTHER INFORMATION: Xaa = D-Arg
<220> FEATURE:
<221> NAME/KEY: MOD_RES
<222> LOCATION: (8)
<223> OTHER INFORMATION: C-terminal amidation

<400> SEQUENCE: 49

Xaa Xaa Xaa Xaa Xaa Xaa Xaa Xaa
1               5

<210> SEQ ID NO 50
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Tyr
<220> FEATURE:
<221> NAME/KEY: VARIANT
<222> LOCATION: (3)
<223> OTHER INFORMATION: Xaa = D-Gly
<220> FEATURE:
<221> NAME/KEY: VARIANT
<222> LOCATION: (4), (7), (8), (10), (11), (12)
<223> OTHER INFORMATION: Xaa = D-Arg
<220> FEATURE:
<221> NAME/KEY: VARIANT
<222> LOCATION: (5), (6)
<223> OTHER INFORMATION: Xaa = D-Lys
<220> FEATURE:
<221> NAME/KEY: VARIANT
<222> LOCATION: (9)
<223> OTHER INFORMATION: Xaa = D-Gln
<220> FEATURE:
<221> NAME/KEY: MOD_RES
<222> LOCATION: (12)
<223> OTHER INFORMATION: C-terminal amidation

<400> SEQUENCE: 50

Xaa Xaa Xaa Xaa Xaa Xaa Xaa Xaa Xaa Xaa Xaa Xaa
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
```

```
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 51

Xaa Xaa Xaa Xaa Xaa Xaa Xaa
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 52

Xaa Xaa Xaa Xaa Xaa Xaa Xaa
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Glutathione
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
```

```
<223> OTHER INFORMATION: C-terminal amidation

<400> SEQUENCE: 53

Xaa Xaa Xaa Xaa Xaa Xaa Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: DISULFID
<222> LOCATION: (1)..(1)
<223> OTHER INFORMATION: Cys-Cys disulfide bonded to Glutathione
<220> FEATURE:
<221> NAME/KEY: VARIANT
<222> LOCATION: (2)...(7)
<223> OTHER INFORMATION: Xaa = D-Arg

<400> SEQUENCE: 54

Xaa Xaa Xaa Xaa Xaa Xaa Xaa
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to acetylated
      Glutathione
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 55

Xaa Xaa Xaa Xaa Xaa Xaa Xaa
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
```

```
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to
      3-Mercaptopropionic acid
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 56

Xaa Xaa Xaa Xaa Xaa Xaa Xaa
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Polyethylene glycol
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 57

Xaa Xaa Xaa Xaa Xaa Xaa Xaa
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
```

```
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Polyethylene glycol
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 58

Xaa Xaa Xaa Xaa Xaa Xaa Xaa
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Polyethylene glycol
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 59

Xaa Xaa Xaa Xaa Xaa Xaa Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Cys
<220> FEATURE:
<221> NAME/KEY: VARIANT
<222> LOCATION: (2), (6)
```

```
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 60

Xaa Xaa Xaa Xaa Xaa Xaa Xaa
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = bAla
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Cys
<220> FEATURE:
<221> NAME/KEY: DISULFID
<222> LOCATION: (2)..(2)
<223> OTHER INFORMATION: Cys-Cys disulfide bonded to Cys
<220> FEATURE:
<221> NAME/KEY: VARIANT
<222> LOCATION: (3), (7)
<223> OTHER INFORMATION: Xaa = D-Ala
<220> FEATURE:
<221> NAME/KEY: VARIANT
<222> LOCATION: (4), (5), (6), (8)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 61

Xaa Xaa Xaa Xaa Xaa Xaa Xaa Xaa
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = bAla
<220> FEATURE:
<221> NAME/KEY: VARIANT
<222> LOCATION: (2)
<223> OTHER INFORMATION: Xaa = D-Cys
<220> FEATURE:
<221> NAME/KEY: DISULFID
<222> LOCATION: (2)..(2)
<223> OTHER INFORMATION: Cys-Cys disulfide bonded to Cys
<220> FEATURE:
<221> NAME/KEY: VARIANT
<222> LOCATION: (3), (7)
<223> OTHER INFORMATION: Xaa = D-Ala
```

```
<220> FEATURE:
<221> NAME/KEY: VARIANT
<222> LOCATION: (4), (5), (6), (8)
<223> OTHER INFORMATION: Xaa = D-Arg

<400> SEQUENCE: 62

Xaa Xaa Xaa Xaa Xaa Xaa Xaa Xaa
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg

<400> SEQUENCE: 63

Xaa Gly Xaa Xaa Xaa Gly Xaa
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg

<400> SEQUENCE: 64

Xaa Ala Xaa Xaa Xaa Ala Xaa
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Val
```

```
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 65

Xaa Xaa Xaa Xaa Xaa Xaa Xaa
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Val
<220> FEATURE:
<221> NAME/KEY: VARIANT
<222> LOCATION: (3), (4), (5), (7)
<223> OTHER INFORMATION: Xaa = D-Arg

<400> SEQUENCE: 66

Xaa Xaa Xaa Xaa Xaa Xaa Xaa
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 67

Xaa Xaa Xaa Xaa Xaa Xaa Xaa
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic peptide
```

-continued

```
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Glu
<220> FEATURE:
<221> NAME/KEY: MOD_RES
<222> LOCATION: (7)
<223> OTHER INFORMATION: C-terminal amidation

<400> SEQUENCE: 68

Xaa Xaa Xaa Xaa Xaa Xaa Xaa
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Glu
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 69

Xaa Xaa Xaa Xaa Xaa Xaa Xaa
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
```

```
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), 6)
<223> OTHER INFORMATION: Xaa = D-Ala
<220> FEATURE:
<221> NAME/KEY: VARIANT
<222> LOCATION: (3), (4), (5)
<223> OTHER INFORMATION: Xaa = D-Arg
<220> FEATURE:
<221> NAME/KEY: VARIANT
<222> LOCATION: (7)
<223> OTHER INFORMATION: Xaa = D-Lys
<220> FEATURE:
<221> NAME/KEY: MOD_RES
<222> LOCATION: (7)
<223> OTHER INFORMATION: C-terminal amidation

<400> SEQUENCE: 70

Xaa Xaa Xaa Xaa Xaa Xaa Xaa
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Glu
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 71

Xaa Xaa Xaa Xaa Xaa Xaa Xaa
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
```

```
<222> LOCATION: (2), (6)
<223> OTHER INFORMATION: Xaa = D-Ala
<220> FEATURE:
<221> NAME/KEY: VARIANT
<222> LOCATION: (3)
<223> OTHER INFORMATION: Xaa = D-Lys
<220> FEATURE:
<221> NAME/KEY: VARIANT
<222> LOCATION: (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 72

Xaa Xaa Xaa Xaa Xaa Xaa Xaa
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (4)
<223> OTHER INFORMATION: Xaa = D-Lys
<220> FEATURE:
<221> NAME/KEY: VARIANT
<222> LOCATION: (3), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 73

Xaa Xaa Xaa Xaa Xaa Xaa Xaa
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
```

```
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 74

Xaa Xaa Xaa Xaa Xaa Xaa Xaa
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: MOD_RES
<222> LOCATION: (7)
<223> OTHER INFORMATION: C-terminal amidation

<400> SEQUENCE: 75

Cys Ala Arg Arg Arg Ala Arg
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3)
<223> OTHER INFORMATION: Xaa = D-Ala
<220> FEATURE:
<221> NAME/KEY: VARIANT
<222> LOCATION: (4)...(9)
<223> OTHER INFORMATION: Xaa = D-Arg
<220> FEATURE:
<221> NAME/KEY: MOD_RES
<222> LOCATION: (9)
<223> OTHER INFORMATION: C-terminal amidation

<400> SEQUENCE: 76

Xaa Xaa Xaa Xaa Xaa Xaa Xaa Xaa Xaa
1               5

<210> SEQ ID NO 77
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
```

```
<223> OTHER INFORMATION: N-terminal acetylation
<220> FEATURE:
<221> NAME/KEY: VARIANT
<222> LOCATION: (2), (3), (4)
<223> OTHER INFORMATION: Xaa = D-Ala
<220> FEATURE:
<221> NAME/KEY: VARIANT
<222> LOCATION: (5)...(10)
<223> OTHER INFORMATION: Xaa = D-Arg
<220> FEATURE:
<221> NAME/KEY: MOD_RES
<222> LOCATION: (10)
<223> OTHER INFORMATION: C-terminal amidation

<400> SEQUENCE: 77

Xaa Xaa Xaa Xaa Xaa Xaa Xaa Xaa Xaa Xaa
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (6), (8)
<223> OTHER INFORMATION: Xaa = D-Ala
<220> FEATURE:
<221> NAME/KEY: VARIANT
<222> LOCATION: (3), (5), (7), (9)
<223> OTHER INFORMATION: Xaa = D-Arg
<220> FEATURE:
<221> NAME/KEY: MOD_RES
<222> LOCATION: (9)
<223> OTHER INFORMATION: C-terminal amidation

<400> SEQUENCE: 78

Xaa Xaa Xaa Xaa Xaa Xaa Xaa Xaa Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6), (8)
<223> OTHER INFORMATION: Xaa = D-Ala
<220> FEATURE:
<221> NAME/KEY: VARIANT
<222> LOCATION: (3), (4), (5), (7), (9)
<223> OTHER INFORMATION: Xaa = D-Arg
<220> FEATURE:
<221> NAME/KEY: MOD_RES
<222> LOCATION: (9)
<223> OTHER INFORMATION: C-terminal amidation
```

<400> SEQUENCE: 79

Xaa Xaa Xaa Xaa Xaa Xaa Xaa Xaa Xaa
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 80

Xaa Xaa Xaa Xaa Xaa Xaa Xaa
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys interchain bond with benzoyl
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 81

Xaa Xaa Xaa Xaa Xaa Xaa Xaa
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation

```
<220> FEATURE:
<221> NAME/KEY: DISULFID
<222> LOCATION: (1)..(1)
<223> OTHER INFORMATION: Cys-Cys interchain bond with acetyl
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 82

Xaa Xaa Xaa Xaa Xaa Xaa Xaa
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Phe
<220> FEATURE:
<221> NAME/KEY: MOD_RES
<222> LOCATION: (7)
<223> OTHER INFORMATION: C-terminal amidation

<400> SEQUENCE: 83

Xaa Xaa Xaa Xaa Xaa Xaa Xaa
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
```

```
<221> NAME/KEY: VARIANT
<222> LOCATION: (6)
<223> OTHER INFORMATION: Xaa = D-Ile
<220> FEATURE:
<221> NAME/KEY: MOD_RES
<222> LOCATION: (7)
<223> OTHER INFORMATION: C-terminal amidation

<400> SEQUENCE: 84

Xaa Xaa Xaa Xaa Xaa Xaa Xaa
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Leu
<220> FEATURE:
<221> NAME/KEY: MOD_RES
<222> LOCATION: (7)
<223> OTHER INFORMATION: C-terminal amidation

<400> SEQUENCE: 85

Xaa Xaa Xaa Xaa Xaa Xaa Xaa
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (7)
<223> OTHER INFORMATION: Xaa = D-Arg
<220> FEATURE:
<221> NAME/KEY: VARIANT
<222> LOCATION: (5)
<223> OTHER INFORMATION: Xaa = D-Lys
<220> FEATURE:
<221> NAME/KEY: MOD_RES
```

```
<222> LOCATION: (7)
<223> OTHER INFORMATION: C-terminal amidation

<400> SEQUENCE: 86

Xaa Xaa Xaa Xaa Xaa Xaa Xaa
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Val
<220> FEATURE:
<221> NAME/KEY: MOD_RES
<222> LOCATION: (7)
<223> OTHER INFORMATION: C-terminal amidation

<400> SEQUENCE: 87

Xaa Xaa Xaa Xaa Xaa Xaa Xaa
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Pro
<220> FEATURE:
<221> NAME/KEY: MOD_RES
<222> LOCATION: (7)
<223> OTHER INFORMATION: C-terminal amidation

<400> SEQUENCE: 88
```

```
Xaa Xaa Xaa Xaa Xaa Xaa Xaa
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-His
<220> FEATURE:
<221> NAME/KEY: MOD_RES
<222> LOCATION: (7)
<223> OTHER INFORMATION: C-terminal amidation

<400> SEQUENCE: 89

Xaa Xaa Xaa Xaa Xaa Xaa Xaa
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Gln
<220> FEATURE:
<221> NAME/KEY: MOD_RES
<222> LOCATION: (7)
<223> OTHER INFORMATION: C-terminal amidation

<400> SEQUENCE: 90

Xaa Xaa Xaa Xaa Xaa Xaa Xaa
1               5

<210> SEQ ID NO 91
```

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Thr
<220> FEATURE:
<221> NAME/KEY: MOD_RES
<222> LOCATION: (7)
<223> OTHER INFORMATION: C-terminal amidation

<400> SEQUENCE: 91

Xaa Xaa Xaa Xaa Xaa Xaa Xaa
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ser
<220> FEATURE:
<221> NAME/KEY: MOD_RES
<222> LOCATION: (7)
<223> OTHER INFORMATION: C-terminal amidation

<400> SEQUENCE: 92

Xaa Xaa Xaa Xaa Xaa Xaa Xaa
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 93

Xaa Xaa Xaa Xaa Xaa Gly Xaa
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Gle
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 94

Xaa Xaa Xaa Xaa Xaa Xaa Xaa
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
```

```
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 95

Xaa Gly Xaa Xaa Xaa Xaa Xaa
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ile
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 96

Xaa Xaa Xaa Xaa Xaa Xaa Xaa
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Pro
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
```

```
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 97

Xaa Xaa Xaa Xaa Xaa Xaa Xaa
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Leu
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 98

Xaa Xaa Xaa Xaa Xaa Xaa Xaa
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Gln
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
```

<223> OTHER INFORMATION: C-terminal amidation

<400> SEQUENCE: 99

Xaa Xaa Xaa Xaa Xaa Xaa Xaa
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Thr
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 100

Xaa Xaa Xaa Xaa Xaa Xaa Xaa
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Val
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 101

Xaa Xaa Xaa Xaa Xaa Xaa Xaa

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ser
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 102

Xaa Xaa Xaa Xaa Xaa Xaa Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-His
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 103

Xaa Xaa Xaa Xaa Xaa Xaa Xaa
1               5

<210> SEQ ID NO 104
<211> LENGTH: 7

```
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Phe
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 104

Xaa Xaa Xaa Xaa Xaa Xaa Xaa
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 105

Xaa Xaa Xaa Gly Xaa Xaa Xaa
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
```

```
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Pro
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 106

Xaa Xaa Xaa Xaa Xaa Xaa Xaa
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Glu
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 107

Xaa Xaa Xaa Xaa Xaa Xaa Xaa
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
```

```
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Thr
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 108

Xaa Xaa Xaa Xaa Xaa Xaa Xaa
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-His
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 109

Xaa Xaa Xaa Xaa Xaa Xaa Xaa
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
```

```
<223> OTHER INFORMATION: Xaa = D-Phe
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 110

Xaa Xaa Xaa Xaa Xaa Xaa Xaa
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ser
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 111

Xaa Xaa Xaa Xaa Xaa Xaa Xaa
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Gln
<220> FEATURE:
<221> NAME/KEY: VARIANT
<222> LOCATION: (6)
<223> OTHER INFORMATION: Xaa = D-Ala
```

```
<220> FEATURE:
<221> NAME/KEY: MOD_RES
<222> LOCATION: (7)
<223> OTHER INFORMATION: C-terminal amidation

<400> SEQUENCE: 112

Xaa Xaa Xaa Xaa Xaa Xaa Xaa
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Val
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 113

Xaa Xaa Xaa Xaa Xaa Xaa Xaa
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Leu
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation
```

```
<400> SEQUENCE: 114

Xaa Xaa Xaa Xaa Xaa Xaa Xaa
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ile
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 115

Xaa Xaa Xaa Xaa Xaa Xaa Xaa
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = N-methylglycine (sarcosine)
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 116

Xaa Xaa Xaa Xaa Xaa Xaa Xaa
1               5
```

```
<210> SEQ ID NO 117
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = N-methylglycine (sarcosine)
<220> FEATURE:
<221> NAME/KEY: MOD_RES
<222> LOCATION: (7)
<223> OTHER INFORMATION: C-terminal amidation

<400> SEQUENCE: 117

Xaa Xaa Xaa Xaa Xaa Xaa Xaa
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = N-methylalanine (Nma)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 118

Xaa Xaa Xaa Xaa Xaa Xaa Xaa
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
```

```
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = N-methylalanine (Nma)
<220> FEATURE:
<221> NAME/KEY: MOD_RES
<222> LOCATION: (7)
<223> OTHER INFORMATION: C-terminal amidation

<400> SEQUENCE: 119

Xaa Xaa Xaa Xaa Xaa Xaa Xaa
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = 2-aminoisobutyric acid (Aib)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 120

Xaa Xaa Xaa Xaa Xaa Xaa Xaa
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
```

```
<223> OTHER INFORMATION: Xaa = D-Arg
<220> FEATURE:
<221> NAME/KEY: VARIANT
<222> LOCATION: (4)
<223> OTHER INFORMATION: Xaa = N-methylalanine (Nma)
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 121

Xaa Xaa Xaa Xaa Xaa Xaa Xaa
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = N-methylalanine (Nma)
<220> FEATURE:
<221> NAME/KEY: MOD_RES
<222> LOCATION: (7)
<223> OTHER INFORMATION: C-terminal amidation

<400> SEQUENCE: 122

Xaa Xaa Xaa Xaa Xaa Xaa Xaa
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = 2-aminoisobutyric acid (Aib)
<220> FEATURE:
<221> NAME/KEY: VARIANT
<222> LOCATION: (3), (4), (5), (7)
<223> OTHER INFORMATION: Xaa = D-Arg
```

```
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 123

Xaa Xaa Xaa Xaa Xaa Xaa Xaa
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = 2-aminoisobutyric acid (Aib)
<220> FEATURE:
<221> NAME/KEY: MOD_RES
<222> LOCATION: (7)
<223> OTHER INFORMATION: C-terminal amidation

<400> SEQUENCE: 124

Xaa Xaa Xaa Xaa Xaa Xaa Xaa
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = N-methylglycine (sarcosine)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation
```

```
<400> SEQUENCE: 125

Xaa Xaa Xaa Xaa Xaa Xaa Xaa
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = N-methylglycine (sarcosine)
<220> FEATURE:
<221> NAME/KEY: MOD_RES
<222> LOCATION: (7)
<223> OTHER INFORMATION: C-terminal amidation

<400> SEQUENCE: 126

Xaa Xaa Xaa Xaa Xaa Xaa Xaa
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = N-methylalanine (Nma)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 127

Xaa Xaa Xaa Xaa Xaa Xaa Xaa
1               5
```

```
<210> SEQ ID NO 128
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = N-methylglycine (sarcosine)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 128

Xaa Xaa Xaa Xaa Xaa Xaa Xaa
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = Norleucine (NLeu)
<220> FEATURE:
<221> NAME/KEY: MOD_RES
<222> LOCATION: (7)
<223> OTHER INFORMATION: C-terminal amidation

<400> SEQUENCE: 129

Xaa Xaa Xaa Xaa Xaa Xaa Xaa
1               5

<210> SEQ ID NO 130
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Norleucine (dNLeu)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 130

Xaa Xaa Xaa Xaa Xaa Xaa Xaa
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Norvaline (dNval)
<220> FEATURE:
<221> NAME/KEY: MOD_RES
<222> LOCATION: (7)
<223> OTHER INFORMATION: C-terminal amidation

<400> SEQUENCE: 131

Xaa Xaa Xaa Xaa Xaa Xaa Xaa
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
```

```
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Norvaline (dNval)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 132

Xaa Xaa Xaa Xaa Xaa Xaa Xaa
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Norleucine (dNLeu)
<220> FEATURE:
<221> NAME/KEY: MOD_RES
<222> LOCATION: (7)
<223> OTHER INFORMATION: C-terminal amidation

<400> SEQUENCE: 133

Xaa Xaa Xaa Xaa Xaa Xaa Xaa
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Norleucine (dNLeu)
<220> FEATURE:
<221> NAME/KEY: VARIANT
<222> LOCATION: (3), (4), (5), (7)
<223> OTHER INFORMATION: Xaa = D-Arg
```

```
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 134

Xaa Xaa Xaa Xaa Xaa Xaa Xaa
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = D-Norvaline (dNVal)
<220> FEATURE:
<221> NAME/KEY: MOD_RES
<222> LOCATION: (7)
<223> OTHER INFORMATION: C-terminal amidation

<400> SEQUENCE: 135

Xaa Xaa Xaa Xaa Xaa Xaa Xaa
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Norvaline (dNVal)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
```

```
<221> NAME/KEY: MOD_RES
<222> LOCATION: (7)
<223> OTHER INFORMATION: C-terminal amidation

<400> SEQUENCE: 136

Xaa Xaa Xaa Xaa Xaa Xaa Xaa
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Norvaline (dNVal)
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 137

Xaa Xaa Xaa Xaa Xaa Xaa Xaa
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Norleucine (dNLeu)
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 138
```

```
Xaa Xaa Xaa Xaa Xaa Xaa Xaa
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with D-homocysteine (dHcy)
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 139

Xaa Xaa Xaa Xaa Xaa Xaa Xaa
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with 3-mercaptopropionic acid (Mpa)
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 140

Xaa Xaa Xaa Xaa Xaa Xaa Xaa
1               5
```

```
<210> SEQ ID NO 141
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with acetylated L-Cysteine
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 141

Xaa Xaa Xaa Xaa Xaa Xaa Xaa
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with D-Cysteine
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 142

Xaa Xaa Xaa Xaa Xaa Xaa Xaa
1               5

<210> SEQ ID NO 143
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with Polyethylene glycol
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 143

Xaa Xaa Xaa Xaa Xaa Xaa Xaa
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with Polyethylene glycol
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 144

Xaa Xaa Xaa Xaa Xaa Xaa Xaa
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic peptide

<400> SEQUENCE: 145

Cys Glu Glu Glu Glu Glu Glu
1               5

<210> SEQ ID NO 146
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(5)
<223> OTHER INFORMATION: Xaa = D-Arg
<220> FEATURE:
<221> NAME/KEY: VARIANT
<222> LOCATION: (6), (7)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 146

Xaa Xaa Xaa Xaa Xaa Xaa Xaa
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Lys
<220> FEATURE:
<221> NAME/KEY: MOD_RES
<222> LOCATION: (7)
<223> OTHER INFORMATION: C-terminal amidation

<400> SEQUENCE: 147

Xaa Xaa Xaa Xaa Xaa Xaa Xaa
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (6)
<223> OTHER INFORMATION: Xaa = D-Ala
```

```
<220> FEATURE:
<221> NAME/KEY: VARIANT
<222> LOCATION: (3), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 148

Xaa Xaa Xaa Xaa Xaa Xaa Xaa
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 149

Xaa Xaa Xaa Xaa Xaa Gly Xaa
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = D-Gln
<220> FEATURE:
<221> NAME/KEY: MOD_RES
<222> LOCATION: (7)
<223> OTHER INFORMATION: C-terminal amidation
```

```
<400> SEQUENCE: 150

Xaa Xaa Xaa Xaa Xaa Xaa Xaa
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = D-His
<220> FEATURE:
<221> NAME/KEY: MOD_RES
<222> LOCATION: (7)
<223> OTHER INFORMATION: C-terminal amidation

<400> SEQUENCE: 151

Xaa Xaa Xaa Xaa Xaa Xaa Xaa
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = D-Ile
<220> FEATURE:
<221> NAME/KEY: MOD_RES
<222> LOCATION: (7)
<223> OTHER INFORMATION: C-terminal amidation

<400> SEQUENCE: 152

Xaa Xaa Xaa Xaa Xaa Xaa Xaa
1               5
```

```
<210> SEQ ID NO 153
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (5)
<223> OTHER INFORMATION: Xaa = D-Ala
<220> FEATURE:
<221> NAME/KEY: DISULFID
<222> LOCATION: (2)..(2)
<223> OTHER INFORMATION: Bond with 1,3-diaminopropionic acid (DAP)
<220> FEATURE:
<221> NAME/KEY: VARIANT
<222> LOCATION: (3), (4), (6)
<223> OTHER INFORMATION: Xaa = D-Arg
<220> FEATURE:
<221> NAME/KEY: MOD_RES
<222> LOCATION: (6)
<223> OTHER INFORMATION: C-terminal amidation

<400> SEQUENCE: 153

Xaa Xaa Xaa Xaa Xaa Xaa
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5)
<223> OTHER INFORMATION: Xaa = D-Homoarginine
<220> FEATURE:
<221> NAME/KEY: VARIANT
<222> LOCATION: (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 154

Xaa Xaa Xaa Xaa Xaa Xaa Xaa
1               5

<210> SEQ ID NO 155
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = a thiol-containing amino acid residue
<220> FEATURE:
<221> NAME/KEY: VARIANT
<222> LOCATION: (2)
<223> OTHER INFORMATION: Xaa = a non-cationic amino acid residue
<220> FEATURE:
<221> NAME/KEY: VARIANT
<222> LOCATION: (3), (4), (7)
<223> OTHER INFORMATION: Xaa = any amino acid residue
<220> FEATURE:
<221> NAME/KEY: VARIANT
<222> LOCATION: (5)
<223> OTHER INFORMATION: Xaa = a cationic amino acid residue
<220> FEATURE:
<221> NAME/KEY: VARIANT
<222> LOCATION: (6)
<223> OTHER INFORMATION: Xaa = a non-cationic amino acid residue

<400> SEQUENCE: 155

Xaa Xaa Xaa Xaa Xaa Xaa Xaa
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2)
<223> OTHER INFORMATION: Xaa = a non-cationic amino acid residue
<220> FEATURE:
<221> NAME/KEY: VARIANT
<222> LOCATION: (3), (4), (7)
<223> OTHER INFORMATION: Xaa = any amino acid residue
<220> FEATURE:
<221> NAME/KEY: VARIANT
<222> LOCATION: (5)
<223> OTHER INFORMATION: Xaa = D-Arg, L-Arg, D-Lys or L-Lys
<220> FEATURE:
<221> NAME/KEY: VARIANT
<222> LOCATION: (6)
<223> OTHER INFORMATION: Xaa = a non-cationic amino acid residue

<400> SEQUENCE: 156

Xaa Xaa Xaa Xaa Xaa Xaa Xaa
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2), (3), (4)
<223> OTHER INFORMATION: Xaa = any amino acid residue
<220> FEATURE:
<221> NAME/KEY: VARIANT
<222> LOCATION: (5), (7)
```

```
<223> OTHER INFORMATION: Xaa = any cationic amino acid residue
<220> FEATURE:
<221> NAME/KEY: VARIANT
<222> LOCATION: (6)
<223> OTHER INFORMATION: Xaa = a non-cationic amino acid residue

<400> SEQUENCE: 157

Xaa Xaa Xaa Xaa Xaa Xaa Xaa
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2), (6)
<223> OTHER INFORMATION: Xaa = a non-cationic amino acid residue
<220> FEATURE:
<221> NAME/KEY: VARIANT
<222> LOCATION: (3), (4), (7)
<223> OTHER INFORMATION: Xaa = any amino acid residue
<220> FEATURE:
<221> NAME/KEY: VARIANT
<222> LOCATION: (5)
<223> OTHER INFORMATION: Xaa = D-Arg, L-Arg, D-Lys or L-Lys

<400> SEQUENCE: 158

Xaa Xaa Xaa Xaa Xaa Xaa Xaa
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (7)
<223> OTHER INFORMATION: Xaa = any cationic amino acid residue
<220> FEATURE:
<221> NAME/KEY: VARIANT
<222> LOCATION: (5)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala

<400> SEQUENCE: 159

Xaa Xaa Xaa Xaa Xaa Xaa Xaa
1               5

<210> SEQ ID NO 160
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2), (3), (7)
<223> OTHER INFORMATION: Xaa = any cationic amino acid residue
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (5)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala

<400> SEQUENCE: 160

Xaa Xaa Xaa Xaa Xaa Xaa Xaa
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (7)
<223> OTHER INFORMATION: Xaa = any amino acid
<220> FEATURE:
<221> NAME/KEY: VARIANT
<222> LOCATION: (5)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala

<400> SEQUENCE: 161

Xaa Xaa Xaa Xaa Xaa Xaa Xaa
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic peptide

<400> SEQUENCE: 162

His Asp Ala Pro Ile Gly Tyr Asp
1               5

<210> SEQ ID NO 163
<211> LENGTH: 9
<212> TYPE: PRT
<213> ORGANISM: Artificial Sequence
<220> FEATURE:
```

<223> OTHER INFORMATION: Synthetic peptide

<400> SEQUENCE: 163

Cys His Asp Ala Pro Ile Gly Tyr Asp
1               5

<210> SEQ ID NO 164
<211> LENGTH: 11
<212> TYPE: PRT
<213> ORGANISM: Artificial Sequence
<220> FEATURE:
<223> OTHER INFORMATION: Synthetic peptide

<400> SEQUENCE: 164

Tyr Gly Arg Lys Lys Arg Arg Gln Arg Arg Arg
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic peptide

<400> SEQUENCE: 165

Cys Tyr Gly Arg Lys Lys Arg Arg Gln Arg Arg Arg
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Synthetic peptide

<400> SEQUENCE: 166

Cys Ser Phe Asn Ser Tyr Glu Leu Gly Ser Leu
1               5                   10

<210> SEQ ID NO 167
<211> LENGTH: 9
<212> TYPE: PRT
<213> ORGANISM: Artificial Sequence
<220> FEATURE:
<223> OTHER INFORMATION: Synthetic peptide

<400> SEQUENCE: 167

Cys Pro Asp Tyr His Asp Ala Gly Ile
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic peptide

<400> SEQUENCE: 168

Cys Glu Ala Val Ser Leu Lys Pro Thr
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 169

Glu Ser Val Ser Leu Lys Pro Thr
1               5

<210> SEQ ID NO 170
<211> LENGTH: 14
<212> TYPE: PRT
<213> ORGANISM: Artificial Sequence
<220> FEATURE:
<223> OTHER INFORMATION: Synthetic peptide

<400> SEQUENCE: 170

Cys Arg Phe Ala Arg Lys Gly Ala Leu Arg Gln Lys Asn Val
1               5                   10

<210> SEQ ID NO 171
<211> LENGTH: 6
<212> TYPE: PRT
<213> ORGANISM: Artificial Sequence
<220> FEATURE:
<223> OTHER INFORMATION: Synthetic peptide

<400> SEQUENCE: 171

Tyr Gly Arg Lys Lys Arg
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic peptide

<400> SEQUENCE: 172

Cys Tyr Gly Arg Lys Lys Arg
1               5

<210> SEQ ID NO 173
<211> LENGTH: 11
<212> TYPE: PRT
<213> ORGANISM: Artificial Sequence
<220> FEATURE:
<223> OTHER INFORMATION: Synthetic peptide

<400> SEQUENCE: 173

Tyr Gly Arg Arg Ala Arg Arg Ala Arg Arg
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Synthetic peptide

<400> SEQUENCE: 174

Cys Tyr Gly Arg Arg Ala Arg Arg Ala Arg Arg
1               5                   10

<210> SEQ ID NO 175
<211> LENGTH: 4
<212> TYPE: PRT
<213> ORGANISM: Artificial Sequence
<220> FEATURE:
<223> OTHER INFORMATION: Synthetic peptide
```

```
<400> SEQUENCE: 175

Cys Arg Arg Arg
1

<210> SEQ ID NO 176
<211> LENGTH: 5
<212> TYPE: PRT
<213> ORGANISM: Artificial Sequence
<220> FEATURE:
<223> OTHER INFORMATION: Synthetic peptide

<400> SEQUENCE: 176

Cys Arg Arg Arg Arg
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic peptide

<400> SEQUENCE: 177

Cys Arg Arg Arg Arg Arg Arg Arg
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic peptide

<400> SEQUENCE: 178

Cys Arg Arg Arg Arg Arg Arg Arg Arg
1               5

<210> SEQ ID NO 179
<211> LENGTH: 10
<212> TYPE: PRT
<213> ORGANISM: Artificial Sequence
<220> FEATURE:
<223> OTHER INFORMATION: Synthetic peptide

<400> SEQUENCE: 179

Cys Arg Arg Arg Arg Arg Arg Arg Arg Arg
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic peptide

<400> SEQUENCE: 180

Cys Arg Arg Arg Arg Arg Arg Arg Arg Arg Arg
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Synthetic peptide

<400> SEQUENCE: 181
```

```
Cys Arg Arg Arg Arg Arg Arg Arg Arg Arg Arg
1               5                   10

<210> SEQ ID NO 182
<211> LENGTH: 13
<212> TYPE: PRT
<213> ORGANISM: Artificial Sequence
<220> FEATURE:
<223> OTHER INFORMATION: Synthetic peptide

<400> SEQUENCE: 182

Cys Arg Arg Arg Arg Arg Arg Arg Arg Arg Arg Arg
1               5                   10

<210> SEQ ID NO 183
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = L-Cys
<220> FEATURE:
<221> NAME/KEY: VARIANT
<222> LOCATION: (2), (6)
<223> OTHER INFORMATION: Xaa = a non-cationic amino acid residue
<220> FEATURE:
<221> NAME/KEY: VARIANT
<222> LOCATION: (3), (4), (7)
<223> OTHER INFORMATION: Xaa = any amino acid residue
<220> FEATURE:
<221> NAME/KEY: VARIANT
<222> LOCATION: (5)
<223> OTHER INFORMATION: Xaa = D-Arg, L-Arg, D-Lys or L-Lys

<400> SEQUENCE: 183

Xaa Xaa Xaa Xaa Xaa Xaa Xaa
1               5
```